United States Patent
Vogelstein et al.

(10) Patent No.: US 12,252,743 B2
(45) Date of Patent: *Mar. 18, 2025

(54) SAFE SEQUENCING SYSTEM

(71) Applicant: The Johns Hopkins University, Baltimore, MD (US)

(72) Inventors: Bert Vogelstein, Baltimore, MD (US); Kenneth W. Kinzler, Frankford, DE (US); Nickolas Papadopoulos, Towson, MD (US); Isaac A. Kinde, Beaumont, CA (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/507,776

(22) Filed: Nov. 13, 2023

(65) Prior Publication Data
US 2024/0084381 A1 Mar. 14, 2024

Related U.S. Application Data

(60) Continuation of application No. 17/837,591, filed on Jun. 10, 2022, which is a continuation of application No. 17/324,380, filed on May 19, 2021, now Pat. No. 11,453,913, which is a continuation of application No. 15/240,034, filed on Aug. 18, 2016, now Pat. No. 11,180,803, which is a division of application No. 15/090,773, filed on Apr. 5, 2016, now abandoned, which is a division of application No. 14/814,030, filed on Jul. 30, 2015, now Pat. No. 9,487,829, which is a division of application No. 14/111,715, filed as application No. PCT/US2012/033207 on Apr. 12, 2012, now Pat. No. 9,476,095.

(60) Provisional application No. 61/484,482, filed on May 10, 2011, provisional application No. 61/476,150, filed on Apr. 15, 2011.

(51) Int. Cl.
*C12Q 1/6869* (2018.01)
*C12Q 1/6806* (2018.01)
*C12Q 1/6874* (2018.01)
*C12Q 1/6876* (2018.01)

(52) U.S. Cl.
CPC ......... *C12Q 1/6874* (2013.01); *C12Q 1/6806* (2013.01); *C12Q 1/6869* (2013.01); *C12Q 1/6876* (2013.01); *C12Q 2525/179* (2013.01); *C12Q 2525/191* (2013.01); *C12Q 2563/179* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,308,751 A * | 5/1994 | Ohkawa | C12Q 1/6869 |
| | | | 435/6.1 |
| 5,750,341 A | 5/1998 | Macevicz | |
| 6,090,935 A | 7/2000 | Breivik et al. | |
| 6,156,504 A | 12/2000 | Gocke et al. | |
| 6,248,521 B1 | 6/2001 | Once | |
| 6,306,597 B1 | 10/2001 | Macevicz | |
| 6,361,940 B1 | 3/2002 | Van Ness et al. | |
| 6,514,736 B1 | 2/2003 | Erich et al. | |
| 6,576,420 B1 | 6/2003 | Carson et al. | |
| 6,686,157 B2 | 2/2004 | Ward et al. | |
| 6,746,845 B2 | 6/2004 | Kinzler et al. | |
| 6,815,212 B2 | 11/2004 | Ness et al. | |
| 6,890,764 B2 | 5/2005 | Chee et al. | |
| 6,942,968 B1 | 9/2005 | Dickinson et al. | |
| 6,977,153 B2 | 12/2005 | Kumar et al. | |

(Continued)

FOREIGN PATENT DOCUMENTS

| | | |
|---|---|---|
| CN | 1360059 | 7/2002 |
| CN | 102241772 | 11/2011 |

(Continued)

OTHER PUBLICATIONS

Abbosh et al., "Phylogenetic ctDNA analysis depicts early-stage lung cancer evolution", Nature 545: 446-451, 2017.

(Continued)

*Primary Examiner* — Angela M. Bertagna
*Assistant Examiner* — Carolyn L Greene
(74) *Attorney, Agent, or Firm* — Fish & Richardson P.C.

(57) ABSTRACT

The identification of mutations that are present in a small fraction of DNA templates is essential for progress in several areas of biomedical research. Though massively parallel sequencing instruments are in principle well-suited to this task, the error rates in such instruments are generally too high to allow confident identification of rare variants. We here describe an approach that can substantially increase the sensitivity of massively parallel sequencing instruments for this purpose. One example of this approach, called "Safe-SeqS" for (Safe-Sequencing System) includes (i) assignment of a unique identifier (UID) to each template molecule; (ii) amplification of each uniquely tagged template molecule to create UID-families; and (iii) redundant sequencing of the amplification products. PCR fragments with the same UID are truly mutant ("super-mutants") if ≥95% of them contain the identical mutation. We illustrate the utility of this approach for determining the fidelity of a polymerase, the accuracy of oligonucleotides synthesized in vitro, and the prevalence of mutations in the nuclear and mitochondrial genomes of normal cells.

8 Claims, 7 Drawing Sheets
Specification includes a Sequence Listing.

(56) References Cited

U.S. PATENT DOCUMENTS

| | | |
|---|---|---|
| 7,056,660 B1 | 6/2006 | Diehl et al. |
| 7,060,431 B2 | 6/2006 | Chee et al. |
| 7,115,400 B1 | 10/2006 | Adessi et al. |
| 7,211,390 B2 | 5/2007 | Rothberg et al. |
| 7,232,656 B2 | 6/2007 | Balsubramanian et al. |
| 7,264,929 B2 | 9/2007 | Rothberg et al. |
| 7,323,305 B2 | 1/2008 | Leamon et al. |
| 7,323,310 B2 | 1/2008 | Peters et al. |
| 7,499,806 B2 | 3/2009 | Kermani et al. |
| 7,601,499 B2 * | 10/2009 | Berka ............... C12Q 1/6806 536/23.1 |
| 7,682,790 B2 | 3/2010 | Hollander et al. |
| 7,683,035 B1 | 3/2010 | Erbacher et al. |
| 7,700,286 B2 | 4/2010 | Stroun et al. |
| 7,702,468 B2 | 4/2010 | Chinitz et al. |
| 7,704,687 B2 | 4/2010 | Wang et al. |
| 7,745,125 B2 | 6/2010 | Gelfand et al. |
| 7,754,429 B2 | 7/2010 | Rigatti et al. |
| 7,776,531 B1 | 8/2010 | Black et al. |
| 7,811,759 B2 | 10/2010 | Han |
| 7,899,626 B2 | 3/2011 | Kruglyak et al. |
| 7,901,897 B2 | 3/2011 | Stuelpnagel et al. |
| 7,948,015 B2 | 5/2011 | Rothberg et al. |
| 7,957,913 B2 | 6/2011 | Chinitz et al. |
| 7,977,108 B2 | 7/2011 | Newhouse et al. |
| 8,021,888 B2 | 9/2011 | Mohammed et al. |
| 8,026,053 B2 | 9/2011 | Samuels et al. |
| 8,043,834 B2 | 10/2011 | Abarzua et al. |
| 8,076,074 B2 | 12/2011 | Mohammed |
| 8,093,063 B2 | 1/2012 | Albitar |
| 8,150,626 B2 | 4/2012 | Fan et al. |
| 8,182,989 B2 | 5/2012 | Bignell et al. |
| 8,190,373 B2 | 5/2012 | Huang et al. |
| 8,288,103 B2 | 10/2012 | Oliphant et al. |
| 8,298,767 B2 | 10/2012 | Brenner et al. |
| 8,343,718 B2 | 1/2013 | Van Der Werf et al. |
| 8,372,637 B2 | 2/2013 | Hollander |
| 8,383,345 B2 | 2/2013 | Shendure et al. |
| 8,481,292 B2 | 7/2013 | Casbon et al. |
| 8,492,089 B2 | 7/2013 | Owen et al. |
| 8,658,572 B2 | 2/2014 | Albert et al. |
| 8,728,732 B2 | 5/2014 | Guerrero Preston et al. |
| 8,741,630 B2 | 6/2014 | Dickinson et al. |
| 8,741,811 B2 | 6/2014 | Lo et al. |
| 8,765,419 B2 | 7/2014 | Hirschbein et al. |
| 8,822,158 B2 | 9/2014 | Froehlich et al. |
| 8,835,358 B2 | 9/2014 | Fodor et al. |
| 8,865,410 B2 | 10/2014 | Shendure et al. |
| 8,871,687 B2 | 10/2014 | Strom |
| 8,877,436 B2 | 11/2014 | Eder et al. |
| 8,911,942 B2 | 12/2014 | Mohammed et al. |
| 8,962,250 B2 | 2/2015 | Stanley |
| 9,012,149 B2 | 4/2015 | Kim et al. |
| 9,029,103 B2 | 5/2015 | Rigatti et al. |
| 9,045,796 B2 | 6/2015 | Gunderson et al. |
| 9,051,606 B2 | 6/2015 | Liu et al. |
| 9,074,206 B2 | 7/2015 | Wu et al. |
| 9,085,798 B2 | 7/2015 | Chee |
| 9,115,410 B2 | 8/2015 | Nazarenko et al. |
| 9,128,861 B2 | 9/2015 | Bartha et al. |
| 9,163,283 B2 | 10/2015 | Chee et al. |
| 9,222,134 B2 | 12/2015 | Mann |
| 9,228,234 B2 | 1/2016 | Rabinowitz et al. |
| 9,233,125 B2 | 1/2016 | Davila et al. |
| 9,238,832 B2 | 1/2016 | Will et al. |
| 9,279,146 B2 | 3/2016 | Gupta et al. |
| 9,340,830 B2 | 5/2016 | Lipson et al. |
| 9,382,581 B2 | 7/2016 | Froehner et al. |
| 9,389,234 B2 | 7/2016 | Von Hoff et al. |
| 9,399,794 B2 | 7/2016 | Liu |
| 9,404,156 B2 | 8/2016 | Hicks et al. |
| 9,410,206 B2 | 8/2016 | Hoon et al. |
| 9,410,956 B1 | 8/2016 | Cheng |
| 9,422,593 B2 | 8/2016 | Rothmann et al. |
| 9,424,392 B2 | 8/2016 | Rabinowitz et al. |
| 9,441,267 B2 | 9/2016 | Gunderson et al. |
| 9,453,258 B2 | 9/2016 | Kain et al. |
| 9,476,095 B2 | 10/2016 | Vogelstein et al. |
| 9,487,823 B2 | 11/2016 | Lasken et al. |
| 9,487,829 B2 | 11/2016 | Vogelstein et al. |
| 9,546,399 B2 | 1/2017 | Amorese et al. |
| 9,546,404 B2 | 1/2017 | Sanders et al. |
| 9,556,491 B2 | 1/2017 | Hoon |
| 9,567,640 B2 | 2/2017 | Hoon |
| 9,574,234 B2 | 2/2017 | Straus et al. |
| 9,587,273 B2 | 3/2017 | Stuelpnagel et al. |
| 9,593,366 B2 | 3/2017 | Nazarenko et al. |
| 9,598,731 B2 | 3/2017 | Talasaz |
| 9,670,530 B2 | 6/2017 | Kostem et al. |
| 9,689,047 B2 | 6/2017 | O'Neil et al. |
| 9,702,004 B2 | 7/2017 | Van Eijk et al. |
| 9,708,655 B2 | 7/2017 | Mandell et al. |
| 9,745,632 B2 | 8/2017 | Parr et al. |
| 9,752,188 B2 | 9/2017 | Schmitt et al. |
| 9,760,530 B2 | 9/2017 | Harsha et al. |
| 9,783,847 B2 | 10/2017 | Chee |
| 9,783,854 B2 | 10/2017 | Sanders et al. |
| 9,792,403 B2 | 10/2017 | Sun et al. |
| 9,797,000 B2 | 10/2017 | Lowe et al. |
| 9,816,139 B2 | 11/2017 | Breen |
| 9,828,672 B2 | 11/2017 | Varadarajan et al. |
| 9,834,822 B2 | 12/2017 | Talasaz et al. |
| 9,873,908 B2 | 1/2018 | Gupta et al. |
| 9,879,312 B2 | 1/2018 | Steemers et al. |
| 9,902,992 B2 | 2/2018 | Talasaz et al. |
| 9,914,973 B2 | 3/2018 | Cheng |
| 9,920,366 B2 | 3/2018 | Eltoukhy et al. |
| 9,944,924 B2 | 4/2018 | Rigatti et al. |
| 9,957,570 B2 | 5/2018 | Mori et al. |
| 9,965,585 B2 | 5/2018 | Lo et al. |
| 9,992,598 B2 | 6/2018 | Reiche |
| 10,011,826 B2 | 7/2018 | Hollander et al. |
| 10,011,870 B2 | 7/2018 | Zimmermann et al. |
| 10,017,759 B2 | 7/2018 | Kaper et al. |
| 10,023,904 B2 | 7/2018 | Villahermosa Jaen et al. |
| 10,023,917 B2 | 7/2018 | Buettner et al. |
| 10,041,127 B2 | 8/2018 | Talasaz |
| 10,102,337 B2 | 10/2018 | Scolnick et al. |
| 10,113,196 B2 | 10/2018 | Ryan et al. |
| 10,113,199 B2 | 10/2018 | Morin et al. |
| 10,125,399 B2 | 11/2018 | West |
| 10,208,338 B2 | 2/2019 | Makarov et al. |
| 10,227,652 B2 | 3/2019 | Rabinowitz et al. |
| 10,240,202 B2 | 3/2019 | Rabinowitz et al. |
| 10,266,893 B2 | 4/2019 | Rabinowitz et al. |
| 10,388,403 B2 | 8/2019 | Rava et al. |
| 10,422,006 B2 | 9/2019 | Samuels et al. |
| 10,450,611 B2 | 10/2019 | West et al. |
| 10,457,995 B2 | 10/2019 | Talasaz |
| 10,494,678 B2 | 12/2019 | Talasaz |
| 10,501,793 B2 | 12/2019 | Chee et al. |
| 10,501,810 B2 | 12/2019 | Talasaz |
| 10,522,242 B2 | 12/2019 | Rabinowitz et al. |
| 10,526,658 B2 | 1/2020 | Babiarz et al. |
| 10,538,759 B2 | 1/2020 | Stuelpnage et al. |
| 10,538,814 B2 | 1/2020 | Babiarz et al. |
| 10,557,172 B2 | 2/2020 | Babiarz et al. |
| 10,577,601 B2 | 3/2020 | Shendure et al. |
| 10,590,482 B2 | 3/2020 | Ryan et al. |
| 10,597,653 B2 | 3/2020 | Sabot et al. |
| 10,619,214 B2 | 4/2020 | Lo et al. |
| 10,655,180 B2 | 5/2020 | Babiarz et al. |
| 10,704,085 B2 | 7/2020 | Talasaz et al. |
| 10,704,086 B2 | 7/2020 | Talasaz et al. |
| 10,704,105 B2 | 7/2020 | Samuels et al. |
| 10,704,108 B2 | 7/2020 | Vogelstein et al. |
| 10,731,220 B2 | 8/2020 | Babiarz et al. |
| 10,732,220 B2 | 8/2020 | Tamura et al. |
| 10,783,364 B2 | 9/2020 | Gao |
| 10,787,713 B2 | 9/2020 | Samuels et al. |
| 10,801,063 B2 | 10/2020 | Eltoukhy et al. |
| 10,822,663 B2 | 11/2020 | Talasaz |
| 11,180,803 B2 | 11/2021 | Vogelstein et al. |
| 11,299,783 B2 | 4/2022 | West et al. |

(56) References Cited

U.S. PATENT DOCUMENTS

| | | |
|---|---|---|
| 11,408,037 B2 | 8/2022 | Babiarz et al. |
| 11,453,913 B2 | 9/2022 | Vogelstein et al. |
| 11,479,807 B2 | 10/2022 | Kennedy et al. |
| 2002/0119448 A1 | 8/2002 | Sorge et al. |
| 2002/0160404 A1 | 10/2002 | Dietmaier et al. |
| 2003/0148335 A1 | 8/2003 | Shen et al. |
| 2004/0209299 A1 | 10/2004 | Pinter et al. |
| 2004/0259105 A1 | 12/2004 | Fan et al. |
| 2005/0136405 A1 | 6/2005 | Linder et al. |
| 2005/0153313 A1 | 7/2005 | Endege et al. |
| 2005/0244847 A1 | 11/2005 | Domanico et al. |
| 2006/0127918 A1 | 6/2006 | Mohammed et al. |
| 2006/0263789 A1 | 11/2006 | Kincaid |
| 2006/0292576 A1 | 12/2006 | Albitar et al. |
| 2007/0020640 A1 | 1/2007 | McCloskey et al. |
| 2007/0077570 A1 | 4/2007 | Lao et al. |
| 2007/0269805 A1 | 11/2007 | Hogers |
| 2008/0160580 A1 | 7/2008 | Adessi et al. |
| 2008/0286795 A1 | 11/2008 | Kawashima et al. |
| 2009/0088328 A1 | 4/2009 | Mohammed et al. |
| 2009/0105081 A1 | 4/2009 | Rodesch et al. |
| 2009/0105959 A1 | 4/2009 | Braverman et al. |
| 2009/0215062 A1 | 8/2009 | Lee |
| 2009/0233802 A1 | 9/2009 | Bignell et al. |
| 2009/0298187 A1 | 12/2009 | Nazarenko et al. |
| 2010/0041048 A1 | 2/2010 | Diehl et al. |
| 2010/0069263 A1 | 3/2010 | Shendure et al. |
| 2010/0113758 A1 | 5/2010 | Wilmer et al. |
| 2010/0127186 A1 | 5/2010 | Bykanov et al. |
| 2010/0129874 A1 | 5/2010 | Mitra et al. |
| 2010/0248991 A1 | 9/2010 | Roesler et al. |
| 2010/0273219 A1 | 10/2010 | May et al. |
| 2011/0152111 A1 | 6/2011 | Fan et al. |
| 2011/0217309 A1 | 9/2011 | Buck et al. |
| 2011/0319415 A1 | 12/2011 | Thomas et al. |
| 2012/0010091 A1 | 1/2012 | Linnarson |
| 2012/0065081 A1 | 3/2012 | Chee |
| 2012/0156753 A1 | 6/2012 | Jendrisak et al. |
| 2012/0225428 A1 | 9/2012 | Beck et al. |
| 2013/0059741 A1 | 3/2013 | Weiner |
| 2013/0266938 A1 | 10/2013 | Will |
| 2014/0011199 A1 | 1/2014 | Speiser et al. |
| 2014/0038837 A1 | 2/2014 | Fung et al. |
| 2014/0050788 A1 | 2/2014 | Daniel et al. |
| 2014/0066317 A1 | 3/2014 | Talasaz |
| 2014/0128270 A1 | 5/2014 | Nakao |
| 2014/0271635 A1 | 9/2014 | Brogdon et al. |
| 2014/0336996 A1 | 11/2014 | Sun et al. |
| 2014/0364323 A1 | 12/2014 | Fan et al. |
| 2015/0011416 A1 | 1/2015 | Lei et al. |
| 2015/0024948 A1 | 1/2015 | Dugas et al. |
| 2015/0051085 A1 | 2/2015 | Vogelstein et al. |
| 2015/0087535 A1 | 3/2015 | Patel |
| 2015/0093756 A1 | 4/2015 | Wolff et al. |
| 2015/0176071 A1 | 6/2015 | Fisher et al. |
| 2015/0197787 A1 | 7/2015 | Welder et al. |
| 2015/0225775 A1 | 8/2015 | Satya |
| 2015/0252415 A1 | 9/2015 | Vogelstein et al. |
| 2015/0275267 A1 | 10/2015 | O'Neil et al. |
| 2015/0307947 A1 | 10/2015 | Basu et al. |
| 2015/0324519 A1 | 11/2015 | Liu |
| 2015/0360193 A1 | 12/2015 | Fan et al. |
| 2016/0017320 A1 | 1/2016 | Wang et al. |
| 2016/0026758 A1 | 1/2016 | Jabara et al. |
| 2016/0048564 A1 | 2/2016 | Bassett, Jr. et al. |
| 2016/0092630 A1 | 3/2016 | Chen et al. |
| 2016/0194404 A1 | 7/2016 | June et al. |
| 2016/0251704 A1 | 9/2016 | Talasaz et al. |
| 2016/0273049 A1 | 9/2016 | Velculescu et al. |
| 2016/0281154 A1 | 9/2016 | So et al. |
| 2016/0319345 A1 | 11/2016 | Gnerre et al. |
| 2016/0374330 A1 | 12/2016 | Grolz |
| 2017/0009287 A1 | 1/2017 | Brastaad et al. |
| 2017/0039328 A1 | 2/2017 | Kathleen et al. |
| 2017/0058332 A1 | 3/2017 | Kermani et al. |
| 2017/0061072 A1 | 3/2017 | Kermani et al. |
| 2017/0101676 A1 | 4/2017 | Teng et al. |
| 2017/0137876 A1 | 5/2017 | Rigatti et al. |
| 2017/0141793 A1 | 5/2017 | Strauss et al. |
| 2017/0165289 A1 | 6/2017 | Minomi et al. |
| 2017/0175197 A1 | 6/2017 | Gatalica et al. |
| 2017/0183742 A1 | 6/2017 | Thierry et al. |
| 2017/0240972 A1 | 8/2017 | Mokhtari et al. |
| 2017/0240973 A1 | 8/2017 | Eltoukhy et al. |
| 2017/0260590 A1 | 9/2017 | Eltoukhy et al. |
| 2017/0314081 A1 | 11/2017 | Gutin et al. |
| 2017/0316149 A1 | 11/2017 | Maston |
| 2017/0356030 A1 | 12/2017 | Boyanov et al. |
| 2017/0356053 A1 | 12/2017 | Otto et al. |
| 2018/0002738 A1 | 1/2018 | Wang et al. |
| 2018/0002749 A1 | 1/2018 | Larson et al. |
| 2018/0016640 A1 | 1/2018 | Xu et al. |
| 2018/0023119 A1 | 1/2018 | Adey et al. |
| 2018/0037950 A1 | 2/2018 | Gunderson et al. |
| 2018/0051329 A1 | 2/2018 | Elzinga |
| 2018/0087105 A1 | 3/2018 | Larson et al. |
| 2018/0095969 A1 | 4/2018 | Jung et al. |
| 2018/0100859 A1 | 4/2018 | Cardone et al. |
| 2018/0119216 A1 | 5/2018 | Jamshidi et al. |
| 2018/0120291 A1 | 5/2018 | Eltoukhy et al. |
| 2018/0135044 A1 | 5/2018 | Sausen et al. |
| 2018/0135103 A1 | 5/2018 | Furlan et al. |
| 2018/0141020 A1 | 5/2018 | Gunderson et al. |
| 2018/0142304 A1 | 5/2018 | Sanders et al. |
| 2018/0148716 A1 | 5/2018 | Heitz et al. |
| 2018/0155705 A1 | 6/2018 | Wolf et al. |
| 2018/0155774 A1 | 6/2018 | Gunderson et al. |
| 2018/0163201 A1 | 6/2018 | Larson |
| 2018/0171337 A1 | 6/2018 | O'Neil et al. |
| 2018/0195131 A1 | 7/2018 | Mortimer |
| 2018/0201974 A1 | 7/2018 | Fraser |
| 2018/0201992 A1 | 7/2018 | Wu et al. |
| 2018/0203974 A1 | 7/2018 | Venn |
| 2018/0208999 A1 | 7/2018 | Lo et al. |
| 2018/0258490 A1 | 9/2018 | Wang et al. |
| 2019/0206510 A1 | 7/2019 | Jiang et al. |
| 2019/0256924 A1 | 8/2019 | Vogelstein et al. |
| 2019/0287654 A1 | 9/2019 | Curtis et al. |
| 2020/0013482 A1 | 1/2020 | Sikora |
| 2020/0131568 A1 | 4/2020 | Talasaz et al. |
| 2020/0157636 A1 | 5/2020 | Velculescu et al. |
| 2020/0377956 A1 | 12/2020 | Vogelstein et al. |

FOREIGN PATENT DOCUMENTS

| | | | |
|---|---|---|---|
| EP | 1910560 | 12/2010 | |
| EP | 3443119 | 2/2019 | |
| EP | 3177740 | 1/2021 | |
| WO | WO 2001023618 | 4/2001 | |
| WO | WO 2002012897 | 2/2002 | |
| WO | WO 2002016649 | 2/2002 | |
| WO | WO 2002059355 | 8/2002 | |
| WO | WO 2002099982 | 12/2002 | |
| WO | WO 2004070007 | 8/2004 | |
| WO | WO-2007073165 A1 * | 6/2007 | ........... C12Q 1/6827 |
| WO | WO 2008030186 | 3/2008 | |
| WO | WO 2008118877 | 10/2008 | |
| WO | WO 2009152928 | 12/2009 | |
| WO | WO 2010028098 | 3/2010 | |
| WO | WO 2010126614 | 11/2010 | |
| WO | WO 2010127186 | 11/2010 | |
| WO | WO 2010141955 | 12/2010 | |
| WO | WO 2012038839 | 3/2012 | |
| WO | WO 2012092336 | 7/2012 | |
| WO | WO 2012142213 | 10/2012 | |
| WO | WO 2013113816 | 8/2013 | |
| WO | WO 2013148496 | 10/2013 | |
| WO | WO 2014183078 | 11/2014 | |
| WO | WO 2015198074 | 12/2015 | |
| WO | WO 2016130704 | 8/2016 | |
| WO | WO 2016135300 | 9/2016 | |
| WO | WO 2016140974 | 9/2016 | |
| WO | WO 2016141169 | 9/2016 | |
| WO | WO 2016170147 | 10/2016 | |

(56) References Cited

FOREIGN PATENT DOCUMENTS

| | | |
|---|---|---|
| WO | WO 2016134136 | 11/2016 |
| WO | WO 2016193490 | 12/2016 |
| WO | WO 2017019456 | 2/2017 |
| WO | WO 2017032808 | 3/2017 |
| WO | WO 2017053915 | 3/2017 |
| WO | WO 2017085321 | 5/2017 |
| WO | WO 2017123316 | 7/2017 |
| WO | WO 2017127741 | 7/2017 |
| WO | WO 2017132276 | 8/2017 |
| WO | WO 2017132438 | 8/2017 |
| WO | WO 2017136603 | 8/2017 |
| WO | WO 2017151524 | 9/2017 |
| WO | WO 2017181134 | 10/2017 |
| WO | WO 2017181146 | 10/2017 |
| WO | WO 2017181202 | 10/2017 |
| WO | WO 2017197027 | 11/2017 |
| WO | WO 2017201315 | 11/2017 |
| WO | WO 2017205686 | 11/2017 |
| WO | WO 2017218512 | 12/2017 |
| WO | WO 2018009723 | 1/2018 |
| WO | WO 2018013598 | 1/2018 |
| WO | WO 2018057770 | 3/2018 |
| WO | WO 2018064229 | 4/2018 |
| WO | WO 2018064629 | 4/2018 |
| WO | WO 2018068014 | 4/2018 |
| WO | WO 2018077847 | 5/2018 |
| WO | WO 2018081130 | 5/2018 |
| WO | WO 2018085862 | 5/2018 |
| WO | WO 2018093780 | 5/2018 |
| WO | WO 2018111872 | 6/2018 |
| WO | WO 2018119399 | 6/2018 |
| WO | WO 2018119438 | 6/2018 |
| WO | WO 2018119452 | 6/2018 |
| WO | WO 2018125892 | 7/2018 |
| WO | WO 2018136416 | 7/2018 |
| WO | WO 2018093744 | 8/2018 |
| WO | WO 2018137826 | 8/2018 |
| WO | WO 2018177847 | 10/2018 |
| WO | WO 2018204657 | 11/2018 |
| WO | WO 2018218113 | 11/2018 |
| WO | WO 2020021119 | 1/2020 |

OTHER PUBLICATIONS

Abdel-Rahman, "Denosumab versus zoledronic acid to prevent aromatase inhibitors-associated fractures in postmenopausal early breast cancer; a mixed treatment meta-analysis.", Expert Rev Anticancer Ther 16(8): 885-91, 2016.

ACOG Practice Bulletin. Clinical Management Guidelines for Obstetrician-Gynecologists. No. 60, Mar. 2005. "Pregestational diabetes mellitus.", Obstet Gynecol 105. 675-685. 2005.

Affymetrix Human Genome U133 Plus 2.0 Array, Public on Nov. 7, 2003, Gene Expression Omnibus URL: https://www.ncbi.nlm.nih.gov/geo/query/acc.cgi?aco=GPL570> [Retrieved from the internet Jun. 7, 2018].

Agus et al., "Targeting ligand-activated ErbB2 signaling inhibits breast and prostate tumor growth", Cancer Cell 2: 127-137, 2002.

Albert et al., "Direct selection of human genomic loci by microarray hybridization", Nat. Methods 4: 903-905, 2007.

Albertini et al., "In vivo somatic mutations in humans: measurement and analysis.", Annu Rev Genet 24: 305-326, 1990.

AlHilli et al., "Incidence and factors associated with synchronous ovarian and endometrial cancer: a population-based case-control study.", Gynecologie oncology 125: 109-113, 2012.

Alizadeh et al., "The Lymphochip: A Specialized cDNA Microarray for the Genomic-scale Analysis of Gene Expression in Normal and Malignant Lymphocytes," Cold Spring Harbor Symposia on Quantitative Biology, 1999, vol. LXIV:71-78.

Allegra et al., "American Society of Clinical Oncology provisional clinical opinion: testing for KRAS gene mutations in patients with metastatic colorectal carcinoma to predict response to anti-epidermal growth factor receptor monoclonal antibody therapy.", J. Clin. Oncol. 27: 2091-2096, 2009.

Allen et al., "Multi-institutional Validation Study of the American Joint Commission on Cancer (8th Edition) Changes for T and N Staging in Patients With Pancreatic Adenocarcinoma.", Ann Surg 265(1): 185-191, 2017.

Allory et al., "Telomerase Reverse Transcriptase Promoter Mutations in Bladder Cancer: High Frequency Across Stages, Detection in Urine, and Lack of Association with Outcome", Eur Urol., 2014, 65:360-366.

Al-Shannsi et al., "Molecular spectrum of KRAS, NRAS, BRAF, PIK3CA, TP53, and APC somatic gene mutations In Arab patients with colorectal cancer: determination of frequency and distribution pattern," Journal of Gastrointestinal Oncology, 2016, 7(6):882-902.

Alvarez et al., "Widespread Hypomethylation Occurs Early and Synergizes with Gene Amplification during Esophageal Carcinogenesis", PLOS Genetics, vol. 7, issue 3, e1001356, 1-14 pages, 2011.

Alvarez-Chaver et al., "Proteomics for discovery of candidate colorectal cancer biomarkers", World J. Gastroenterol, 20(14): 3804-3824, 2014.

American Cancer Society, "Can ovarian cancer be found early?", (Available at http://www.cancer.org/Cancer/OvarianCancer/DetailedGuide/ovariancancer-detection), 4 pages, 2017.

American College of Obstetricians and Gynecologists, ACOG Committee Opinion: No. 280, Dec. 2002. "The role of the generalist obstetrician-gynecologist in the early detection of ovarian cancer.", Obstet Gynecol 100, 1413-1416, 2002.

Andre et al., "Improved overall survival with oxaliplatin, fluorouracil, and leucovorin as adjuvant treatment in stage II or III colon cancer in the MOSAIC trial.", J Clin Oncol., 2009, 27(19):3109-3116.

Anglesio et al., "Cancer-Associated Mutations in Endometriosis without Cancer", N Engl J Med 376: 1835-1848, 2017.

Ansari et al., "Relationship between tumour size and outcome in pancreatic ductal adenocarcinoma", Br J Surg., 2017, 104(5): 600-607.

Antoni et al., "Bladder Cancer Incidence and Mortality: A Global Overview and Recent Trends,", Eur Urol, 2017, 71(1):96-108.

Araten et al., A quantitative measurement of the human somatic mutation rate., Cancer Res 65: 8111-8117, 2005.

Arbyn et al., "European Guidelines for Quality Assurance in Cervical Cancer Screening. Second edition—summary document.", Ann Oncol 21, 448-458 2010.

Arnold et al., "Global burden of cancer attributable to high body-mass index in 2012: a population-based study.", The Lancet. Oncology 16, 36-46, 2015.

Audeh et al., "Oral poly(ADP-ribose) polymerase inhibitor olaparib in patients with BRCA1 or BRCA2 mutations and recurrent ovarian cancer: a proof-of-concept trial.", Lancet 376: 245-251, 2010.

Australian Office Action in Australian Application No. 2017203206, dated Jan. 23, 2018.

Awada et al., "An open-label, dose-escalation study to evaluate the safety and pharmacokinetics of CEP-9722 (a PARP-I and PARP-2 inhibitor) in combination with gemcitabine and cisplatin in patients with advanced solid tumors", Anticancer Drugs 27(4): 342-8, 2016.

Baard et al., Diagnostic dilemmas in patients with upper tract urothelial carcinoma., Nat Rev Urol, 14(3), 181-191, 2017.

Baehner, "The analytical validation of the Oncotype DX Recurrence Score assay", Ecancermedicalscience 10: 675. 2016.

Bahuva et al., "Morphologic abnormalities are poorly predictive of visceral pain in chronic pancreatitis.", Pancreas 42(1): 6-10, 2013.

Bainbridge et al., "Whole exome capture in solution with 3 Gbp of data" Genome Biology, 11(6): R62, 2010.

Balmain et al., "A model for RAS mutation patterns in cancers: finding the sweet spot.," Nature Reviews, 2018, 18:767-777.

Bandiera et al., "Cancer antigen 125, human epididymis 4, kallikrein 6, osteopontin and soluble mesothelin-related peptide immunocomplexed with immunoglobulin Min epithelial ovarian cancer diagnosis.", Clinical chemistry and laboratory medicine: CCLM I FESCC 51, 1815-1824, 2013.

Bang et al., "Trastuzumab in combination with chemotherapy versus chemotherapy alone for treatment of HER2-positive advanced

(56) References Cited

OTHER PUBLICATIONS gastric or gastro-oesophageal junction cancer (ToGA): a phase 3, open-label, randomised controlled trial", Lancet 376: 687-697,2010.
Bansal et al., "Low- and high-grade bladder cancer appraisal via serum-based proteomics approach.", Clin Chim Acta 436: 97-103, 2014.
Bardelli et al., "Liquid Biopsies, What We Do Not Know (Yet)", Cell Press, 31, 172-179,2017.
Baretton et al., "Inerphase Cytogenetic Analysis of Prostatic Carcinomas by Use of Nonisotopic in Situ Hybridization", Cancer Research 54, 4472-4480, 1994.
Barkan et al., "The Paris System for Reporting Urinary Cytology: The Quest to Develop a Standardized Terminology.", Adv AnatPathol 23:193-201, 2016.
Barnes, "The fidelity of Taq polymerase catalyzing PCR is improved by an N-terminal deletion", Gene 112:29-35, 1992.
Barollo et al., "Prevalence, tumorigenic role, and biochemical implications of rare BRAF alterations", Thyroid: offical journal of the american thyroid association 24, 809-819.2014.
Barroso-Sousa et al., "Clinical Development of the CDK4/6 Inhibitors Ribociclib and Abemaciclib in Breast Cancer", Breast Care 11(3): 167-173, 2016.
Barrow et al., "Cumulative lifetime incidence of extracolonic cancers in Lynch syndrome: a report of 121 families with proven mutations.", Clin. Genet. 75, 141-149, 2009.
Baselga et al., "Pertuzumab plus Trastuzumab plus Docetaxel for Metastatic Breast Cancer", N Engl J Med 366: 109-119, 2012.
Bashashati et al., "Distinct evolutionary trajectories of primary high-grade serous ovarian cancers revealed through spatial mutational profiling.", The Journal of pathology, 231: 21-34, 2013.
Bast et al., "A radioimmunoassay using a monoclonal antibody to monitor the course of epithelial ovarian cancer", The New England journal of medicine 309, 883-887, 1983.
Beddowes et al., "Predicting treatment resistance and relapse through circulating DNA." Breast 34(Suppl 1): S31-S35, 2017.
Beers et al., "Array-CGH and breast cancer," Breast Cancer Res., 2006, 8(3):210, 10 pages.
Bell et al., "A simple way to treat PCR products prior to sequencing using ExoSAP-IT" BioTechniques, 2008.
Bell et al., "Integrated genomic analyses of ovarian carcinoma.", Nature 474, 609-615, 2011.
Benson et al., "Colon Cancer, Version 1.2017" NCCN, vol. 15, No. 3, 370-398, 2017.
Beroukhim et al., "Assessing the significance of chromosomal aberrations in cancer; Methodology and application to glioma", Proceedings of the National Academy of Sciences, 104: 20007-20012, 2007.
Bertone et al., "Design optimization methods for genomic DNA tiling arrays", Genome Res 16(2); 271-281, 2006.
Bertotti et al., "The genomic landscape of response to EGFR blockade in colorectal cancer.", Nature, 526: 263-7, 2015.
Bettegowda et al. "Detection of circulating tumor DNA in early- and late-stage human malignancies," Sci Transl Med, 2014, 6(224):1-25.
Bettegowda et al., "Detection of Circulating Tumor DNA in Early- and Late-Stage Human Malignancies", Science translational medicine 6(224): 224ra224, 2014.
Biankin et al., "Pancreatic cancer genomes reveal aberrations in axon guidance pathway genes.", Nature 491(7424): 399-405, 2012.
Bielas et al., "Quantification of random genomic mutations.", Nat. Methods, 2: 285-290, 2005.
Binladen et al., "The Use of Coded PCR Primers Enables High-Throughput Sequencing of Multiple Homolog Amplification Products by 454 Parallel Sequencing" PLoS One, 9 pages, Feb. 14, 2007.
Boland et al., "Clinical next generation sequencing to identify actionable aberrations in a phase I program," Oncotarget, 2015, 6(24):20099-20110.

Bowtell et al., "Rethinking ovarian cancer II: reducing mortality from high-grade serous ovarian cancer.", Nature reviews Cancer, 15: 668-79, 2015.
Boyd et al., "Measurement and clinical monitoring of human lymphocyte clonality by massively parallel VDJ pyrosequencing.", Science Trans lat. Med., vol. 1, 12ra23, Supplementary material, pp. 1-30, 2009.
Bozic et al., "Evolutionary dynamics of cancer in response to targeted combination therapy", Elife 2: e00747, 2013.
Brahmer et al., "Safety and activity of anti-PD-L1 antibody in patients with advanced cancer.", N Engl J Med, 366(26): 2455-65, 2012.
Bray et al., "Global estimates of cancer prevalence for 27sites in the adult population in 2008.", Int. J. Cancer, 2012.
Bristow et al., "Survival effect of maximal cytoreductive surgery for advanced ovarian carcinoma during the platinum era: a meta-analysis." J. Clin. Oncol. 20, 1248-1259, 2002.
Burris et al., "Phase I trial of novel kinesin spindle protein (KSP) inhibitor SB-715992 IV days 1, 8, 15 q 28 days", J Clin Oncol. 22: 128, 2004.
Buys et al., "Ovarian cancer screening in the Prostate, Lung, Colorectal and Ovarian (PLCO) cancer screening trial: findings from the initial screen of a randomized trial", American journal of obstetrics and gynecology 193, 1630-1639, 2005.
Buys et al., Effect of screening on ovarian cancer mortality: the Prostate, Lung, Colorectal and Ovarian (PLCO) Cancer Screening Randomized Controlled Trial. JAMA 305, 2295-2303, 2011.
Byron et al., "FGFR2 mutations are rare across histologic subtypes of ovarian cancer," Gynecologic Oncology 117, 125-129, 2010.
Calvez-Kelm et al., "KRAS mutations in blood circulating cell-free DNA: a pancreatic cancer case-control", ONCOTARGET, vol. 7, No. 48, 2016.
Camidge et al., "A phase I safety, tolerability, and pharmacokinetic study of enzastaurin combined with capecitabine in patients with advanced solid tumors", Anticancer Drugs 19: 77-84, 2008.
Campbell et al., "No difference in stem cell somatic mutation between the background mucosa of right- and left-sided sporadic colorectal carcinomas.", J Pathol 186: 31-35, 1998.
Cancer Genome Atlas Research Network, "Comprehensive molecular characterization of urothelial bladder carcinoma.", Nature 507: 315-322, 2014.
Cancer Genome Atlas Research, "Integrated genomic analyses of ovarian carcinoma.", Nature 474: 609-615, 2011.
Cancer.gov [online], "NCI Dictionary of Cancer Terms, Definition of Biomarker," available on or before Apr. 5, 2018, [retrieved on Feb. 26, 2020], retrieved from: URL<https://www.cancer.gov/publications/dictionaries/cancer-terms/def/biomarker>, 1 page.
Capello et al., "Sequential Validation of Blood-Based Protein Biomarker Candidates for Early-Stage Pancreatic Cancer.", J Natl Cancer Inst 109(4), 2017.
Carlson et al., "Screening for ovarian cancer.", Ann. Intern. Afrd. 121, 124-132, 1994.
Casbon et al., "A method for counting PCR template molecules with application to next-generation sequencing." Nucleic Acids Research, 1-8. 2011.
Cass et al., BRCA-mutation-associated fallopian tube carcinoma: a distinct clinical phenotype? Obstetrics and Gynecology 106: 1327-34, 2005.
Castelo-Branco et al., "Methylation of the TERT promoter and risk stratification of childhood brain tumours; an integrative genomic and molecular study," Lancet Oncol., 2013, 14(6):534-542.
Chai et al., Field effect in cancer-an update. Ann Clin Lab Sci 39: 331-337, 2009.
Chan et al., "Size Distributions of Maternal and Fetal DNA in Maternal Plasma", Clinical chemistry 50: 88-92, 2004.
Chan, "Consolidated guidelines on the use of antiretroviral drugs for treating and preventing HIV infection Recommendations for a public health approach", Second Edition, BOOK, 2016.
Chang et al., "CARs: Synthetic Immunoreceptors for Cancer Therapy and Beyond", Trends Mol Med 23(5): 430-450, 2017.
Chang et al., "The clinical utility of endoscopic ultrasound-guided fine-needle aspiration in the diagnosis and staging of pancreatic carcinoma.", Gastrointestinal endoscopy 45, 387-393, 1997.

(56) References Cited

OTHER PUBLICATIONS

Chari et al., "Probability of pancreatic cancer following diabetes: a population based study". Gastroenterology 129(2): 504-511, 2005.
Chen et al., "Aristolochic acid-associated urothelial cancer in Taiwan", Proc Natl Acad Sci US A, 109(21): 8241-8246, 2012.
Chen et al., "CAR T-cell intrinsic PD-1 checkpoint blockade; A two-in-one approach for solid tumor immunotherapy", Oncoimmunology 6(2): e1273302, 2016.
Chen, "Immune checkpoint inhibitors for nonsmall cell lung cancer treatment", J. Chin Med Assoc 80(1): 7-14, 2017.
Cheng et al., "Molecular genetic analysis of ovarian serous cystadenomas", Laboratory investigation; a journal of technical methods and pathology 84, 778-784, 2004.
Cheng et al., "TERT Promoter Mutations Occur Frequently in Urothelial Papilloma and Papillary Urothelial Neoplasm of Low Malignant Potential.", Eur Urol 71 :497-498.2017.
Chetverina et al., "Molecular colony diagnostics; detection and quantitation of viral nucleic acids by in-gel PCR.", Biotechniques 33: 150-152, 154, 156, 2002.
Cheung et al., "High frequency of PIK3RI and PIK3R2 mutations in endometrial cancer elucidates a novel mechanism for regulation of PTEN protein stability.", Cancer Discov 1, 170-185, 2011.
Chinese Office Action issued Mar. 3, 2017 in related Chinese Application No. 201380068411.8.
Chiu et al., "Noninvasive prenatal diagnosis of fetal chromosomal aneuploidy by massively parallel genomic sequencing of DNA in maternal plasma", Proc Natl Acad Sci US A 105: 20458-20463, 2008.
Christensen et al., "Functional ovarian cysts in premenopausal and gynecologically healthy women", Contraception 66, 153-157, 2002.
Chu et al. J. Clin. Oncol. 22:14S, abstr 2078, 2004.
Chung et al., "A whole-genome mouse BAC microarray with 1-Mb resolution for analysis of DNA copy number changes by array comparative genomic hybridization.", Genome Res. 14(1): 188-196, 2004.
Clarke-Pearson, "Clinical Practice, Screening for ovarian cancer.", N Engl J Med., 361(2): 170-177, 2009.
Cobb et al., "Adenocarcinoma of Mullerian origin: review of pathogenesis, molecular biology, and emerging treatment paradigms" Gynecologic Oncology Research and Practice, May 12, 2015 (online), vol. 5, pp. 1-16.
Cohen et al., "Combined circulating tumor DNA and protein biomarker-based liquid biopsy for the earlier detection of pancreatic cancers", PNAS, vol. 114, No. 38, 10202-10207, 2017.
Cohen et al., "Detection and localization of surgically resectable cancers with a multi-analyte blood test", Science, 359(6378): 926-930, 2018.
Cole et al., "Working paper No. 3 Somatic mutant frequency, mutation rates and mutational spectra in the human population in vivo", Mutat Res 304: 33-105, 1994.
Color Hereditary Cancer Test, "A pathogenic mutation was identified in the BRCA1 gene," tm Clinical Grade testing (www.color.com), 2015, 1-12.
Conner et al., "Outcome of unexpected adnexal neoplasia discovered during risk reduction salpingo-oophorectomy in women with germ-line BRCAI or BRCA2 mutations.", Gynecol Oncol 132: 280-6, 2014.
Coombs et al., "Therapy-Related Clonal Hematopoiesis in Patients with Non-hematologic Cancers Is Common and Associated with Adverse Clinical Outcomes" Cell Stem Cell 21(3): 374-382, 2017.
Cooper et al., "Endometrial sampling techniques in the diagnosis of abnormal uterine bleeding.", Obstet Gynecol Clin North Am 27, 235-244, 2000.
Corona et al., "CDK4/6 inhibitors in HER2-positive breast cancer", Cri Rev Oncol Hematol 112: 208-214, 2017.
Cortes et al., "Support-Vector Networks", Machine learning 20: 273-297, 1995.
Costello et al., "Discovery and characterization of artifactual mutations in deep coverage targeted capture sequencing data due to oxidative DNA damage during sample preparation.", Nucleic acids research 41: e67, 2013.
Cowan et al., "Detection of TERT promoter mutations in primary adenocarcinoma of the urinary bladder.", Hum Pathol, 53: 8-13, 2016.
Craig et al., "Identification of genetic variants using bar-coded multiplexed sequencing.", Nat Methods 5; 887-893, 2008.
Cree et al., "The evidence base for circulating tumour DNA blood-based biomarkers for the early detection of cancer: a systematic mapping review", BMC Cancer, 17: 697, 1-17, 2017.
Cruz et al., "Absence of BRAF and NRAS mutations in uveal melanoma", Cancer research 63, 5761-5766, 2003.
Cunningham et al., Cetuximab Monotherapy and Cetuximab plus Irinotecan in Irinotecan-Refractory Metastatic Colorectal Cancer, N. Engl. J. Med., 2004, 351(4):337-345.
D'Souza et al., "Tumor characterization by ultrasound-release of multiple protein and microRNA biomarkers, preclinical and clinical evidence", PLOS ONE, 1-17 pages, 2018.
Dalma-Weiszhausz et al., "The affymetrix GeneChip platform; an overview.", Methods Enzymol. 410; 3-28, 2006.
Darragh et al., "Tumor Detection by Imaging Proteolytic Activity", Cancer Res 70: 1505-12, 2010.
Davies et al., "Mutations of the BRAF gene in human cancer", Nature 417, 949-954, 2002.
Davis et al., "Diagnosis, evaluation and follow-up of asymptomatic microhematuria (AMH) in adults: AUA guideline.", J Urol 188: 2473-2481, 2012.
Dawson et al., "Analysis of Circulating Tumor DNA to Monitor Metastatic Breast Cancer", N Engl J Med 368(13): 1199-1209, 2013.
De Boer et al., "An in vitro assay for frameshift mutations: hotspots for deletions of 1 bp by Klenow-fragment polymerase share a consensus DNA sequence.", Genetics 118: 181-191, 1988.
De Vos et al., "Novel PMS2 Pseudogenes Can Conceal Recessive Mutations Causing a Distinctive Childhood Cancer Syndrome", American journal of human genetic, 74: 954-964, 2004.
Demeure et al., "Whole-genome Sequencing of an Aggressive BRAF Wild-type Papillary Thyroid Cancer Identified EML4-ALK Translocation as a Therapeutic Target", World J Surg., 38: 1296-305, 2014.
Demirol et al., "Effect of endometrioma cystectomy on IVF outcome: a prospective randomized study", Reproductive biomedicine online 12, 639-643, 2006.
DeRisi et al., "Use of a cDNA microarray to analyse gene expression patterns in human cancer.", Nat. Genet. 14: 457-460, 1996.
DeSimone et al., "Rate of pathology from atypical glandular cell Pap tests classified by the Bethesda 2001 nomenclature,", Obstet Gynecol 107, 1285-1291, 2006.
Di Renzo et al., "Expression of the MetfHepatocyte Growth Factor Receptor in Human Pancreatic Cancer", Cancer Res 55(5): 1129-1138, 1995.
Di Renzo et al., "Overexpression and amplification of the met/HGF receptor gene during the progression of colorectal cancer.", Clin Cancer Res 1(2): 147-154, 1995.
Diehl et al., "Analysis of mutations in DNA isolated from plasma and stool of colorectal cancer patients," Gastroenterology 135: 489-498, 2008.
Diehl et al., "Detection and quantification of mutations in the plasma of patients with colorectal tumors", Proceedings of the National Academy of Sciences of the United States of America, 102: 16368-16373, 2005.
Dimashkieh et al., "Evaluation of UroVysion and Cytology for Bladder Cancer Detection", Cancer Cytopathol 121: 591-597, 2013.
Dinkelspiel et al., "Long-term mortality among women with epithelial ovarian cancer.", Gynecologic oncology 138: 421-8, 2015.
Dizon et al., "A Phase II Evaluation of Belinostat and Carboplatin in the Treatment of Recurrent or Persistent Platinum-Resistant Ovarian, Fallopian Tube, or Primary Peritoneal Carcinoma: A Gynecologio Oncology Group Study", Gynecol. Oncol. 125(2): 367-371, 2012.

(56) References Cited

OTHER PUBLICATIONS

Dizon et al., "Phase II Activity of Belinostat (PXD-101), Carboplatin, and Paclitaxel in Women With Previously Treated Ovarian Cancer", Int J. Gynecol. Cancer 23(3): 533-539, 2012.
Dohm et al., "Substantial biases in ultrashort read data sets from high-throughput DNA sequencing.", Nucleic Acids Res 36:e105, 2008.
Dokianakis et al., "Ras gene activation in malignant cells of human ovarian carcinoma peritoneal fluida," Clin & Exp. Metastasis, 1999, 17(4):293-297.
Dong et al., "Combining markers with and without the limit of detection.", Stat Med 33(8): 1307-1320, 2014.
Douville et al., "Detection of aneuploidy in patients with cancer through amplification of long interspersed nucleotide elements (LINEs)", PNAS, vol. 115, No. 8, 1871-1876, 2018.
Dressman et al., Transforming single DNA molecules into fluorescent magnetic particles for detection and enumeration of genetic variations. Proc Natl Acad Sci USA 100(15): 8817-8822, 2003.
Drevis et al., "Phase I Clinical Study of AZD2171, an Oral Vascular Endothelial Growth Factor Signaling Inhibitor, in Patients With Advanced Solid Tumors", 25: 3045-2054, 2007.
Druley et al., "Quantification of rare allelic variants from pooled genomic DNA."; Nat Methods 6: 263-265, 2009.
Duke et al., "Transvaginal aspiration of ovarian cysts: long-term follow-up", Cardiovascular and interventional radiology 29, 401-405, 2006.
Durbin et al., "A map of human genome variation from population-scale sequencing.", Nature 467:1061-1073, 2010.
Dy et al., "Long-Term Survivors of Metastatic Colorectal Cancer Treated with Systemic Chemotherapy Alone: A North Central Cancer Treatment Group Review of 3811 Patients, N0144", Clin Colorectal Cancer 8(2): 88-93, 2009.
Eastman et al., "Maternal viral genotypic zidovudine resistance and infrequent failure of zidovudine therapy to prevent perinatal transmission of human immunodeficiency virus type 1 in pediatric AIDS Clinical Trials Group Protocol 076.", J Infect Dis 177:557-564, 1998.
Easton et al., "Breast and Ovarian Cancer Incidence in BRCA I-Mutation Carriers", Am. J. Hum. Genet. 56: 265-271, 1995.
Eberle et al., "Immunoguided laser assisted microdissection techniques for DNA methylation analysis of archival tissue specimens.", The Journal of molecular diagnostics: JMD 12; 394-401, 2010.
Eckert et al., "Genomics of Ovarian Cancer Progression Reveals Diverse Metastatic Trajectories Including Intraepithelial Metastasis to the Fallopian Tube," Cancer Discov., 2016, 6(12):1342-1351.
Eckert et al., "High fidelity DNA synthesis by the Thermus aquaticus DNA polymerase.", Nucleic Acids Res 18: 3739-3744, 1990.
Egawa et al., "Clinicopathological aspects of small pancreatic cancer. Pancreas", 28(3): 235-240, 2004.
Ehab et al., "Profile of palbociclib in the treatment of metastatic breast cancer", Breast Cancer 8: 83-91, 2016.
Eid et al., "Real-time DNA sequencing from single polymerase molecules", Science 323: 133-138, 2009.
Eliassen et al., "Urinary Estrogens and Estrogen Metabolites and Subsequent Risk of Breast Cancer among Premenopausal Women", Cancer Research, vol. 72, issue 3, 696-706, 2012.
Ellinger et al., "Epigenetic biomarkers in the blood of patients with urological malignancies", Expert Rev Mal Diagn 15: 505-516, 2015.
Ellis et al., "Immune Checkpoint Inhibitors for Patients With Advanced NoneSmall-Cell Lung Cancer: A Systematic Review", Clin Lung Cancer pii: SI525-7304(17)30043-8, 2017.
Elmasry et al., "Genetic mutations in gynaecological cancers," Reviews in Gynaecological and Preinatal Practice, vol. 6, No. 3-4, pp. 115-125, 2006.
Eloubeidi et al., "Endoscopic ultrasound-guided fine needle aspiration biopsy of patients with suspected pancreatic cancer: diagnostic accuracy and acute and 30-day complications.", The American journal of gastroenterology 98, 2663-2668, 2003.

El-Tanani et al., "The regulation and role of osteopontin in malignant transformation and cancer.", Cytokine Growth Factor Rev 17(6): 463-474, 2006.
Elzek et al., "Proteomics of ovarian cancer; functional insights and clinical applications", Cancer Metastasis Rev., 34(1): 83-96, 2015.
Erickson et al., "Detection of somatic TP53 mutations in tampons of patients with highgrade serous ovarian cancer.", Obstetrics and gynecology 124, 881-885, 2014.
Erlich et al., "Alta-Cyclic: a self-optimizing base caller for next-generation sequencing.", Nat Methods 5: 679-682, 2008.
Ernani et al., "Agilent's SureSelect Target Enrichment System: Brining Cost and Process Efficiency to Next-Generation Sequencing," Agilent Technologies—Product Notes, pp. 1-8, 2009.
Ethier et al., "Bone Modifier Use as Adjuvant Therapy for Early Breast Cancer", Curr Oncol Rep 19(3): 15, 2017.
European Office Action issued in related European Application No. 13851273.6, dated Apr. 19, 2017, 8 pages.
European Search Report issued in European Application No. 21173115. 3, dated Oct. 12, 2021, 9 pages.
Extended European Search Report in Application No. 18193794.7, dated Dec. 19, 2018.
Extended European Search Report issued in related European Application No. 12772013.4, dated Sep. 17, 2014, 6 pages.
Extended European Search Report issued in related European Application No. 13851273.6, dated Jun. 1, 2016, 14 pages.
Extended European Search Report issued in related European Application No. 17154750.8, dated Aug. 17, 2017, 16 pages.
Faias et al., "Clinical Impact of KRAS and GNAS Analysis Added to CEA and Cytology in Pancreatic Cystic Fluid Obtained by EUS-FNA", Digestive Diseases and Sciences, vol. 63, No. 9, pp. 2351-2361, 2018.
Falchook et al., "Methylation and histone deacetylase inhibition in combination with platinum treatment in patients with advanced malignancies", Investig, New Drugs 31(5): 1192-1200, 2013.
Falconer et al., "Ovarian cancer risk after salpingectomy: a nationwide population-based study.", J. Natl. Cancer Inst., 107,vol. 2, 2015.
Falzoi et al., "Multiplex genotyping of CYP3A4, CYP3A5, CYP2C9 and CYP2C19 SNPs using MALDI-TOF mass spectrometry", Pharmacogenomics 11: 559-571, 2010.
Fan et al., "Noninvasive diagnosis of fetal aneuploidy by shotgun sequencing DNA from maternal blood.", Proc Natl Acad Sci US A 105: 16266-16271, 2008.
Ferlay et al., "Cancer incidence and mortality patterns in Europe: estimates for: 40 countries in 2012.", European Journal of cancer 49: 1374-403, 2013.
Finn et al., "Palbociclib and Letrozole in Advanced Breast Cancer", N Eng J Med 375: 1925-1936, 2016.
Fishman et al., "The role of ultrasound evaluation in the detection of early-stage epithelial ovarian cancer.", Am J Obstet Gynecol 192, 1214-1221; discussion 1221-1212,2005.
Fong et al., "Inhibition of poly(ADP-ribose) polymerase in tumors from BRCA mutation carriers.", N Engl J Med 361: 123-134, 2009.
Forbes et al., "COSMIC: mining complete cancer genomes in the Catalogue of Somatic Mutations in Cancer.", Nucleic Acids Res 39, D945-950, 2011.
Forbes et al., "COSMIC: somatic cancer genetics at high-resolution", Nucleic Acids Res 45: D777-D783, 2017.
Forshew et al., "Noninvasive identification and monitoring of cancer mutations by targeted deep sequencing of plasma DNA", Sci Transl Med; 4: 136ra68, 2012.
Fradet et al., "Performance characteristics of a new monoclonal antibody test for bladder cancer: ImmunoCyt trade mark.", Can J Urol 4: 400-405, 1997 Abstract.
Friedman et al., "Regularization Paths for Generalized Linear Models via Coordinate Descent", Journal of Statistical Software 33 :74862, 22 pages, 2010.
Frokjaer et al., "Fibrosis, atrophy, and ductal pathology in chronic pancreatitis are associated with pancreatic function but independent of symptoms.", Pancreas 42(7): 1182-1187, 2013.
Frossard et al., "Performance of endosonography-guided fine needle aspiration and biopsy in the diagnosis of pancreatic cystic lesions", The american journal of gastroenterology 98, 1516-1524, 2003.

(56) References Cited

OTHER PUBLICATIONS

Fu et al., "Phase 1b-2a study to reverse platinum resistance through use of a hypomethylating agent, azacitidine, in patients with platinum-resistant or platinum-refractory epithelial ovarian cancer.", Cancer 117(8): 1661-1669, 2011.
Fujiwara et al., "Evaluation of Matrix Metalloproteinase-2 (MMP-2) Activity with Film in situ Zymography for Improved Cytological Diagnosis of Breast Tumors", Breast cancer 13: 272-8, 2006.
Fukagawa et al., "MicroRNA-135a-3p as a promising biomarker and nucleic acid therapeutic agent for ovarian cancer", Cancer Science, 108, 886-896, 2017.
Fallwood et al., "Next-generation DNA sequencing of paired-end tags (PET) for transcriptome and genome analyses" Genome Research, 19: 521-532, 2009.
Gam, "Breast cancer and protein biomarkers", World J. Exp. Med. 2(5): 86-91, 2012.
Gangi et al., "Metabolomio profile in pancreatic cancer patients: a consensusbased approach to identify highly discriminating metabolites", Oncotarget, 7(5):5815-5829, 2016.
Gardner et al., "Evaluation of a 27-gene inherited cancer panel across 630 consecutive patients referred for testing in a clinical diagnostic laboratory," Hereditary Cancer in Clinical Practice, 2018, 16(I):1-10.
Gasi et al., "Overexpression of Full-Length ETVI Transcripts in Clinical Prostate Cancer Due to Gene Translocation", PLOS ONE, vol. 6, issue 1, e16332, 7 pages, 2011.
Gaspari et al. "Fetal ovarian cysts: an early manifestation of McCune-Albright syndrome?, "Prenatal Diagnosis, 2012, 32;859-863.
Geier et al., "Clinical evaluation of atypical glandular cells of undetermined significance.", Am. J. Obstet Gynecol, 184, 64-69, 2001.
Geldenhuys et al., "Sensitivity and specificity of the Pap smear for glandular lesions of the cervix and endometrium.", Acta cytologica 51, 4 7-50, 2007.
Gelmon et al., "Olaparib in patients with recurrent high-grade serous or poorly differentiated ovarian carcinoma or triple-negative breast cancer: a phase 2, multicentre, open-label, non-randomised study", Lancet Oncol. 12: 852-61, 2011.
GenBank Accession No. NM_006218, "*Homo sapiens* phosphatidylinositol-4,5-bisphosphate 3-kinase catalytic subunit alpha (PIK3CA), mRNA," Feb. 16, 2020, 7 pages.
GenBank Accession No. NM_058197, "*Homo sapiens* cyclin dependent kinase inhibitor 2A (CDKN2A), transcript variant 3, mRNA," Dec. 29, 2019, 5 pages.
GenBank Accession No. NM_000546, "*Homo sapiens* tumor protein p53 (TP53), transcript variant 1, mRNA," Feb. 13, 2020, 11 pages.
GenBank Accession No. NM_001126112, "*Homo sapiens* tumor protein p53 (TP53), transcript variant 2, mRNA," Dec. 28, 2019, 11 pages.
GenBank Accession No. NM_001126113, "*Homo sapiens* tumor protein p53 (TP53), transcript variant 4, mRNA," Dec. 8, 2019, 6 pages.
GenBank Accession No. NM_001126114, "*Homo sapiens* tumor protein p53 (TP53), transcript variant 3, mRNA," Dec. 29, 2019, 9 pages.
GenBank Accession No. NM_001276761, "*Homo sapiens* tumor protein p53 (TP53); transcript variant 2, mRNA." Dec. 23, 2019, 5 pages.
GenBank Accession No. NM000077, "*Homo sapiens* cyclin dependent kinase inhibitor 2A (CDKN2A), transcript variant 1, mRNA", dated Oct. 21, 2018, 7 pages.
GenBank Accession No. NM000142, "*Homo sapiens* fibroblast growth factor receptor 3 (FGFR3), transcript variant 1, mRNA", dated Dec. 23, 2018, 8 pages.
GenBank Accession No. NM000245, "*Homo sapiens* MET proto-oncogene, receptor tyrosine kinase (MET), transcript variant 2, mRNA", dated Jan. 13, 2019, 7 pages.
GenBank Accession No. NM000551, "*Homo sapiens* von Hippel-Lindau tumor suppressor (VHL), transcript variant 1, mRNA", dated Dec. 23, 2018, 7 pages.
GenBank Accession No. NM001005862, "*Homo sapiens* erb-b2 receptor tyrosine kinase 2 (ERBB2), transcript variant 2, mRNA", dated Jan. 13, 2019, 8 pages.
GenBank Accession No. NM001127500, "*Homo sapiens* MET proto-oncogene, receptor tyrosine kinase (MET), transcript variant 1, mRNA",dated Jan. 13, 2019, 7 pages.
GenBank Accession No. NM001130442, "*Homo sapiens* HRas proto-oncogene, GTPase (HRAS), transcript variant 3, mRNA", dated Dec. 23, 2018, 5 pages.
GenBank Accession No. NM001163213, "*Homo sapiens* fibroblast growth factor receptor 3 (FGFR3), transcript variant 3, mRNA", dated Dec. 23, 2018, 7 pages.
GenBank Accession No. NM001195132, "*Homo sapiens* cyclin dependent kinase inhibitor 2A (CDKN2A), transcript variant 5, mRNA", dated Oct. 21, 2018, 7 pages.
GenBank Accession No. NM001289936, "*Homo sapiens* erb-b2 receptor tyrosine kinase 2 (ERBB2), transcript variant 3, mRNA", dated Jan. 13, 2019, 8 pages.
GenBank Accession No. NM001289937, "*Homo sapiens* erb-b2 receptor tyrosine kinase 2 (ERBB2), transcript variant 4, mRNA", dated Jan. 13, 2019, 8 pages.
GenBank Accession No. NM001289938, "*Homo sapiens* erb-b2 receptor tyrosine kinase 2 (ERBB2), transcript variant 5, mRNA", dated Jan. 13, 2019, 6 pages.
GenBank Accession No. NM001318054, "*Homo sapiens* HRas proto-oncogene, GTPase (HRAS), transcript variant 4, mRNA", dated Dec. 23, 2018, 5 pages.
GenBank Accession No. NM001324401, "*Homo sapiens* MET proto-oncogene, receptor tyrosine kinase (MET), transcript variant 3, mRNA", dated Jan. 13, 2019, 5 pages.
GenBank Accession No. NM001324402, "*Homo sapiens* MET proto-oncogene, receptor tyrosine kinase (MET), transcript variant 4, mRNA", dated Jan. 13, 2019, 6 pages.
GenBank Accession No. NM001354723, "*Homo sapiens* von Hippel-Lindau tumor suppressor (VHL), transcript variant 3, mRNA", dated Dec. 23, 2018, 4 pages.
GenBank Accession No. NM001354809, "*Homo sapiens* fibroblast growth factor receptor 3 (FGFR3), transcript variant 4, mRNA", dated Dec. 23, 2018, 6 pages.
GenBank Accession No. NM001354810, "*Homo sapiens* fibroblast growth factor receptor 3 (FGFR3), transcript variant 5, mRNA", dated Dec. 23, 2018, 6 pages.
GenBank Accession No. NM003482, "*Homo sapiens* lysine methyltransferase 2D (KMT2D), mRNA", dated Jan. 13, 2019, 21 pages.
GenBank Accession No. NM004448, "*Homo sapiens* erb-b2 receptor tyrosine kinase 2 (ERBB2), transcript variant 1, mRNA", dated Jan. 13, 2019, 10 pages.
GenBank Accession No. NM004985, "*Homo sapiens* KRAS proto-oncogene, GTPase (KRAS), transcript variant b, mRNA", dated Jan. 13, 2019, 7 pages.
GenBank Accession No. NM005343, "*Homo sapiens* HRas proto-oncogene, GTPase (HRAS), transcript variant 1, mRNA", dated Dec. 29, 2018, 5 pages.
GenBank Accession No. NM022965, "*Homo sapiens* fibroblast growth factor receptor 3 (FGFR3), transcript variant 2, mRNA", dated Dec. 23, 2018, 6 pages.
GenBank Accession No. NM033360, "*Homo sapiens* KRAS proto-oncogene, GTPase (KRAS), transcript variant a, mRNA", dated Jan. 13, 2019, 8 pages.
GenBank Accession No. NM058195, "*Homo sapiens* cyclin dependent kinase inhibitor 2A (CDKN2A), transcript variant 4, mRNA", dated Aug. 4, 2018, 6 pages.
GenBank Accession No. NM058196, "*Homo sapiens* cyclin-dependent kinase inhibitor 2A (melanoma, p16, inhibits CDK4) (CDKN2A), transcript variant 2, mRNA", dated Dec. 21, 2003, 19 pages.
GenBank Accession No. NM176795, "*Homo sapiens* HRas proto-oncogene, GTPase (HRAS), transcript variant 2, mRNA", dated Dec. 23, 2018, 5 pages.

(56) References Cited

OTHER PUBLICATIONS

GenBank Accession No. NM198156, "*Homo sapiens* von Hippel-Lindau tumor suppressor (VHL), transcript variant 2, mRNA", dated Dec. 23, 2018, 7 pages.
GenBank Release Note v. 220, p. 1 (Jun. 2017).
Geng et al., "Function and clinical significance of cireRNAs in solid tumors", Journal of Hematology and Oncology, 11; 98, 20 pages, 2018.
Genovese et al., "Clonal hematopoiesis and blood-cancer risk inferred from blood DNA sequence.", N Engl J Med 371(26): 2477-2487, 2014.
Gerlinger et al., "Intratumor heterogeneity and branched evolution revealed by multiregion sequencing.", N Engl J Med 366, 883-892, 2012.
Ghosh et al., "Quantifying the sensitivities of EGF receptor (EGFR) tyrosine kinase inhibitors in drug resistant non-small cell lung cancer (NSCLC) cells using hydrogel-based peptide array.", Biosensors & Bioelectronics 26: 424-31, 2010.
Giacona et al., " Cell-free DNA in human blood plasma: length measurements in patients with pancreatic cancer and healthy controls.", Pancreas 17: 89-97, 1998.
Gilbert et al., "Assessment of symptomatic women for early diagnosis of ovarian cancer: results from the prospective DOvE pilot project.", The Lancet. Oncology 13, 285-291, 2012.
Giligan et al., "American Society of Clinical Oncology Clinical Practice Guideline on uses of serum tumor markers in adult males with germ cell tumors.", J. Clin. Oncol. 28: 3388-3404, 2010.
Giraldez et al., "Droplet Digital PCR for Absolute Quantification of Extracellular MicroRNAs in Plasma and Serum: Quantification of the Cancer Biomarker hsa-miR-141.", Methods Mol. Biol., 1768: 459-74, 2018.
Gomez et al., "Efficacy and safety of lapatinib as first-line therapy for ErbB2-amplified locally advanced or metastatic breast cancer.", J Clin Oncol 26: 2999-3005, 2008.
Gong et al., "Efficacy and safety of everolimus in Chinese metastatic HR positive, HER2 negative breast cancer patients: a real-world retrospective study", Oncotarget, 8(35): 59810-59822, 2017.
Gonzalez-Pons "Colorectal Cancer Biomarkers: Where Are We Now?", Biomed. Res. Int. 2015: 149014, 2015.
Goodison et al., "A multi-analyte assay for the non-invasive detection of bladder cancer.", PLoS One, 7: e47469, 2012.
Gopalakrishna et al., "Anticipatory Positive Urine Tests for Bladder Cancer.", Ann Surg Oncol., 24: 1747-1753, 2017.
Gore et al., "Somatic coding mutations in human induced pluripotent stem cells.", Nature 471: 63-67, 2011.
Grisham et al., "BRAF mutation is associated with early stage disease and improved outcome in patients with low-grade serous ovarian cancer", Cancer 119, 548-554, 2013.
Grist et al., "In vivo human somatic mutation: frequency and spectrum with age.", Mutat Res 266: 189-196, 1992.
Grollman et al., "Aristolochic acid nephropathy: Harbinger of a global iatrogenic disease.", Environ Mal Mutagen, 54(1): 1-7, 2013.
Gruenberger et al., "Bevacizumab, Capecitabine, and Oxaliplatin As Neoadjuvant Therapy for Patients With Potentially Curable Metastatic Colorectal Cancer", J. Clin. Oncol. 26: 1830-1835, 2008.
Gudmundsson et al. "Genome-Wide Association and Replication Studies Identify Four Variants Associated with Prostate Cancer Susceptibility," Nat. Genet. 2009 41:1122-6.
Guetschow et al., "Detection of prolactin inducible protein mRNA, a biomarker for breast cancer metastasis, using a molecular beacon-based assay.", Anal. Bioanaly. Chem., 404: 399-406, 2012.
Gunderson et al., "Oncologic and reproductive outcomes with progestin therapy in women with endometrial hyperplasia and grade 1 adenocarcinoma: a systematic review," Gynecol Oncol 125, 477-482, 2012.
Haber et al. "Blood-based analyses of cancer: circulating tumor cells and circulating tumor DNA," Cancer Discov, 2014, 4(6):650-661.
Hajdinjak, "Uro Vysion FISH test for detecting urothelial cancers: meta-analysis of diagnostic accuracy and comparison with urinary cytology testing.", Urol Oncol 26: 646-651, 2008.
Halama et al., "Nesting of colon and ovarian cancer cells in the endothelial niche is associated with alterations in glycan and lipid metabolism", Scientific Reports, 7:39999, 10 pages, 2017.
Hall et al., "Linkage of Early-Onset Familial Breast Cancer to Chromosome 17q21", Science 250: 1684-1689, 1990.
Hamanishi et al., "Safety and Antitumor Activity of Anti-PD-1 Antibody, Nivolumab, in Patients With Platinum-Resistant Ovarian Cancer.", J. Clin. Oncol. 33(34): 4015-4022, 2015.
Hamilton et al., "The Molecular Basis of Turcot's Syndrome", The New England Journal of Medicine 332: 839-847, 1995.
Hamilton et al., "Uterine papillary serous and clear cell carcinomas predict for poorer survival compared to grade 3 endometrioid corpus cancers", British journal of cancer 94: 642-646, 2006.
Hannady et al., "Error-correcting barcoded primers for pyrosequencing hundreds of samples in multiplex," Nature Meth., 2007, 5:1-36.
Hannady et al., "Error-correcting barcoded primers for pyrosequencing hundreds of samples in multiplex," Nature Meth., 2007, 5:235-237.
Hare et al.,"mTOR function and therapeutic targeting in breast cancer", Am J Cancer Res 7(3): 383-404, 2017.
Harris et al., "American Society of Clinical Oncology 2007 Update of Recommendations for the Use of Tumor Markers in Breast Cancer", J. Clin. Oncol. 25: 5287-5312, 2007.
Havrilesky et al., "Predictors of clinical outcomes in the laparoscopic management of adnexal masses.", Obstetrics and gynecology 102, 243-251, 2003.
He et al., "Heteroplasmic mitochondrial DNA mutations in normal and tumour cells.", Nature 464; 610-614, 2010.
He et al., "IgH gene rearrangements as plasma biomarkers in Non-Hodgkin's lymphoma patients.", Oncotarget 2, 178-185, 2011.
Hecht et al., "A randomized, double-blind, placebo-controlled, phase III study in patients (Pts) with metastatic adenocarcinoma of the colon or rectum receiving fifirst-line chemotherapy with oxaliplatin/ 5-flfluorouracil/leucovorin and PTK787/ZK 222584 or placebo (CON-FIRM-1)", ASCO Annual Meeting Proceedings J. Clin. Oncol. 23; 16S, abstr. LBA3, 2005.
Heitzer et al., "Current and future perspectives of liquid bipsies in genomics-driven oncology", Nature Reviews Genetics, 2018, 20(2):71-88.
Hellmann et al., "Nivolumab plus ipilimumab as first-line treatment for advanced non-small-cell lung cancer (CheckMate 012): results of an open-label, phase 1, multicohort study", Lancet Oncol. 18(1): 31-41, 2017.
Hellstrom et al., "The HE4 (WFDC2) protein is a biomarker for ovarian carcinoma", Cancer research 63, 3695-3700, 2003.
Hennessy et al., "Ovarian cancer," Lancet, vol. 374, Oct. 17, 2009, 1373-82.
Henrique et al., "DNA hypomethylation in plasma as a cancer biomarker: when less is more?", Expert Rev. Mol. Diagn., 14: 419-22, 2014.
Henry et al., "Cancer biomarkers", Mol. Oncol. 6: 140-146, 2012.
Herbst et al., "Lung cancer.", N Engl J Med, 359(13): 1367-1380, 2008.
Herman et al., "Filter-based hybridization capture of subgenomes enables resequencing and copy-number detection.", Nat Methods 6: 507-510, 2009.
Hiatt et al., "Parallel, tag-directed assembly of locallt dreived short sequence reads.", Nat Methods, (7) 119-122, 2010.
Hiatt et al., "Single molecule molecular inversion probes for targeted, high-accuracy detection of low-frequency variation.", Genome research 23, 843-854, 2013.
Hilger et al., "Laparoscopic management of the adnexal mass.", Clinical obstetrics and gynecology 49, 535-548, 2006.
Hoang et al., "Mutational Signature of Aristolochic Acid Exposure as Revealed by Whole-Exome Sequencing", 2013 Science translational medicine 5: 197ra102, 2013.
Hodges et al., "High definition profiling of mammalian DNA methylation by array capture and single molecule bisulfite sequencing," Genome Research, 19: 1593-1605, 2009.

(56) References Cited

OTHER PUBLICATIONS

Hogenbirk et al., "Defining chromosomal translocation risks in cancer", PNAS, E3649-E3656, 2016.
Hoque et al., "High-throughput molecular analysis of urine sediment for the detection of bladder cancer by high-density single-nucleotide polymorphism array.", Cancer Res 63: 5723-5726, 2003.
Horn et al., "TERT promoter mutations in familial and sporadic melanoma." Science 339: 959-961, 2013.
Hosein et al., "Evaluating the repair of DNA derived from formalin-fixed paraffin-embedded tissues prior to genomic profiling by SNP-CGH analysis", Lab. Invest., 93, 701-710, 2013.
Hosgood et al., "Mitochondrial DNA copy number and lung cancer risk in a prospective cohort study", Carcinogen., 31: 847-9, 2010.
Howlader et al., SEER Cancer Statistics Review, 1975-2009, National Cancer Institute Bethesda. MD, 2012.
Hsieh et al., "Prescription profile of potentially aristolochic acid containing Chinese herbal products: an analysis of National Health Insurance data in Taiwan between 1997 and 2003", Chin Med, 3: 13, 6 pages, 2008.
Huang et al., "Comparison of Central HER2 Testing With Quantitative Total HER2 Expression and HER2 Homodimer Measurements Using a Novel Proximity-Based Assay", Am. J. Clin. Pathol. 134: 303-11, 2010.
Huang et al., "Highly recurrent TERT promoter mutations in human melanoma.", Science 339: 957-959, 2013.
Huang et al., "T-cell invigoration to tumour burden ratio associated with antiPD-1 response.", Nature 545(7652): 60-65, 2017.
Huber et al., "High-Resolution Liquid Chromatography of DNA Fragments on Non-Porous Poly(Styrene-Divinylbenzene) Particles," Nucleic Acids Res., 1993, 21:1061-6.
Hug et al.," Measurement of the No. of molecules of a single mRNA species in a complex mRNA preparation," J. theor. Biol., 2003,221:615-624.
Hughes et al., "Expression profiling using microarrays fabricated by an ink-jet oligonucleotide synthesizer.", Nat. Biotechnol. 19(4): 342-347, 2001.
Hui et al., "Pembrolizumab as first-line therapy for patients with PD-LI-positive advanced non-small cell lung cancer: a phase 1 trial", Ann Oncol 28(4): 874-881, 2017.
Hun et al., "Systems approach to characterize the metabolism of liver cancer stem cells expressing CD133", Sci. Rep. 7: 45557, 2017.
Huntsman et al. "MLL2, the second human homolog of the *Drosophila trithorax* gene, maps to 19q13.1 and is amplified in solid tumor cell lines," Oncogene, 18, 7975-7984, 1999.
Hurst et al., "Comprehensive mutation analysis of the TERT promoter in bladder cancer and detection of mutations in voided urine.", Eur Urol 65: 367-369, 2014.
Hurwitz et al., "Bevacizumab plus Irinotecan, Fluorouracil, and Leucovorin for Metastatic Colorectal Cancer", N. Engl. J. Med. 350: 2335-2342, 2004.
Ikediobi et al., "Mutation analysis of 24 known cancer genes in the NCI-60 cell line set,", Molecular Cancer Therapeutics, 5(11), 2006.
Ikematsu et al., "Serum midkine levels are increased in patients with various types of carcinomas", Br J Cancer 83(6): 701-706, 2000.
Ingvarsson et al., "Detection of pancreatic cancer using antibody microarray-based serum protein profiling.", Proteomics 8: 2211-9, 2008.
Innis et al., "Protocols for functional genomics" PCR application, (1999).
Insinga et al., "Diagnoses and outcomes in cervical cancer screening: a population-based study.", Am. J. Obstet. Gynecol. 191, 105-113, 2004.
International Preliminary Report on Patentability in PCT Appln. No. PCT/US2018/045669, dated Feb. 11, 2020, 7 pages.
International Preliminary Report on Patentability issued in PCT/US2013/065342, issued May 5, 2015, 7 pages.
International Search Report and Written Opinion for PCT/US2013/065342, mailed Apr. 1, 2014, 11 pages.
International Search Report and Written Opinion in International Application No. PCT/US2012/033207, dated Nov. 28, 2012.
International Search Report and Written Opinion in International Application No. PCT/US2016/046453, dated Nov. 1, 2016, 11 pages.
International Search Report and Written Opinion in International Application No. PCT/US2017/061447, Feb. 19, 2018, 10 pages.
International Search Report and Written Opinion in International Application No. PCT/US2018/030905, dated Oct. 2, 2018, 23 pages.
International Search Report and Written Opinion in International Application No. PCT/US2018/045669, dated Nov. 28, 2018, 15 pages.
International Search Report and Written Opinion in International Application No. PCT/US2019/017973, dated May 17, 2019, 7 pages.
International Search Report and Written Opinion in International Application No. PCT/US2020/014172, dated Apr. 30, 2020, 18 pages.
Irizarry et al., "Summaries of Affymetrix GeneChip probe level data", Nucleic Acids Res 31, 4 :e15, 2003.
Isakoff et al., "P3-16-05: A Phase II Trial Expansion Cohort of the PARP Inhibitor Veliparib (ABT888) and Temozolomide in BRCA1/2 Associated Metastatic Breast Cancer.", Cancer Res 71: P3-16-05, 2011.
Ishikawa et al., "Minute carcinoma of the pancreas measuring 1 cm or less in diameter—collective review of Japanese case reports.", Hepatogastroenterology 46(25): 8-15, 1999.
Jabara et al., "Accurate sampling and deep sequencing of the HIV-I protease gene using a Primer ID.", Proceedings of the National Academy of Sciences of the United States of America 108, 20166-20171, 2011.
Jacobs et al., "Ovarian cancer screening and mortality in the UK Collaborative Trial of Ovarian Cancer Screening UKCTOCS): a randomised controlled trial.", Lancet 387: 945-956, 2016.
Jacobs et al., Sensitivity of transvaginal ultrasound screening for endometrial cancer in postmenopausal women: a case-control study within the UKCTOCS cohort. The Lancet. Oncology 12, 38-48, 2011.
Jahr et al., "DNA Fragments in the Blood Plasma of Cancer Patients; Quantitations and Evidence for Their Origin from Apoptotic and Necrotic Cells", Cancer Research 61: 1659-1665, 2001.
Jain et al., "Personalized Therapy of Cancer," Textbook of Personalized Medicine, 2015, Chapter 10, pp. 199-381.
Jaiswal et al., "Age-related clonal hematopoiesis associated with adverse outcomes.", N Engl J Med 371(26): 2488-2498, 2014.
Jasmine et al., "A Genome-Wide Study of Cytogenetic Changes in Colorectal Cancer Using SNP Microarrays: Opportunities for Future Personalized Treatment", PLoS One 7(2): e31968, 18 pages, 2012.
Jelakovic et al., "Aristolactam-DNA adducts are a biomarker of environmental exposure to aristolochic acid", Kidney Int. 81(6): 559-67, 2012.
Jiao et al., "DAXX/ATRX, MEN1, and mTOR Pathway Genes Are Frequently Altered in Pancreatic Neuroendocrine Tumors", Science 331: 1199-1203, 2011.
Jones et al., "Comparative lesion sequencing provides insights into tumor evolution.", Proceedings of the National Academy of Sciences of the United States of America 105: 4283-4288, 2008.
Jones et al., "Core signaling pathways in human pancreatic cancers revealed by global genomic analyses.", Science 321(5897): 1801-1806, 2008.
Jones et al., "Frequent mutations of chromatin remodeling gene ARIDIA in ovarian clear cell carcinoma.", Science 330, 228-231, 2010.
Jones et al., "Low-grade serous carcinomas of the ovary contain very few point mutations", The Journal of pathology 226, 413-420, 2012.
Jones et al., "Personalized genomic analyses for cancer mutation discovery and interpretation.", Science translational medicine, 7: 283ra53, 2015.
Jones et al., "The epigenomics of cancer.", Cell 128: 683-692, 2007.
Ju et al., "Origins and functional consequences of somatic mitochondrial DNA mutations in human cancer", eLife 3, 28 pages, 2014.

(56) References Cited

OTHER PUBLICATIONS

Jung et al., "Intron retention is a widespread mechanism of tumor-suppressor inactivation.", Nat Genet 47, 1242-1248, 2015.
Jung KW, et al. (2007) Clinicopathological aspects of 542 cases of pancreatic cancer: a special emphasis on small pancreatic cancer. J Korean Med Sci 22 Suppl:S79-85.
Kalinich et al., "An RNA-based signature enables high specificity detection of circulating tumor cells in hepatocellular carcinoma.", Proc Natl Acad Sci USA, 114(S): 1123-1128, 2017.
Kandoth et al., "Integrated genomic characterization of endometrial carcinoma.", Nature 497, 67-73, 2013.
Kandoth et al., "Mutational landscape and significance across 12 major cancer types", Nature 502: 333-339, 2013.
Kang et al., "Inverse correlation between RASSF1A hypermethylation, KRAS and BRAF mutations in cervical adenocarcinoma," Gynecology Oncology, 105, 662-666, 2007.
Karow, "Hopkins Team Develops method to Improve Rare Mutation Detection for Early Cancer Dx," Genomeweb, 3 pages, Jun. 1, 2011.
Karst et al., "Modeling high-grade serous ovarian carcinogenesis from the fallopian tube", Proc. Natl Acad Sci USA 108, 7547-7552, 2011.
Karst et al., "Ovarian cancer pathogenesis: a model in evolution.", Journal of oncology 932371, 13 pages, 2010.
Kato et al., "A new Packing for Separation of DNA Restriction Fragments by High Performance Liquid Chromatography," J. Biochem, 1984, 95:83-86.
Kauff et al., "Risk-reducing salpingooophorectomy in women with a BRCA1 or BRCA2 mutation.", The New England journal of medicine, 346: 1609-15, 2002.
Kaufman et al., "Olaparib monotherapy in patients with advanced cancer and a germline BRCA1/2 mutation.", J Clin. Oncol. 33: 244-250, 2015.
Kawauchi et al., "9p21 index as estimated by dual-color fluorescence in situ hybridization is useful to predict urothelial carcinoma recurrence in bladder washing cytology:", Hum Pathol 40: 1783-1789, 2009.
Kennedy et al., "Detecting ultralow-frequency mutations by Duplex Sequencing.", Nature protocols 9, 2586-2606, 2014.
Kennedy et al., "Somatic mutations in aging, cancer and neurodegeneration", MechAgeing Dey 133: 118-126, 2012.
Keohavong et al., "Fidelity of DNA polymerases in DNA amplification.", Proc Natl Acad Sci US A 86: 9253-9257, 1989.
Kesmodel et al., "Gastrointestinal Cancers Symposium: Multidisciplinary Approaches to the Prevention, Diagnosis, and Therapy of GI Cancers", 2007, abstr 234, 4 pages.
Keys et al., "Primer ID Informs Next-Generation Sequencing Platforms and Reveals Preexisting Drug Resistance Mutations in the HIV-I Reverse Transcriptase Coding Domain.", AIDS Res Hum Retroviruses 31, 658-668, 2015.
Khadra et al., "A prospective analysis of 1,930 patients with hematuria to evaluate current diagnostic practice.", J Urol 163: 524-527, 2000.
Khalid et al., "Pancreatic cyst fluid DNA analysis in evaluating pancreatic cysts: a report of the PANDA study," Gastrointestinal Endoscopy, 2009, 69(6):1095-1102.
Kidd et al., "Developing a SNP panel for forensic identification of individuals", Forensic science international 164: 20-32, 2006.
Killela et al., "TERT promoter mutations occur frequently in gliomas and a subset of tumors derived from cells with low rates of self-renewal.", Proc Natl Acad Sci USA 110:6021-6026, 2013.
Kim et al., "Clinical usefulness of carbohydrate antigen 19-9 as a screening test for pancreatic cancer in an asymptomatic population.", J Gastroenterol Hepatol 19(2): 182-186, 2004.
Kim et al., "Impact of intraoperative rupture of the ovarian capsule on prognosis in patients with early-stage epithelial ovarian cancer: a meta-analysis.", European journal of surgical oncology : the journal of the European Society of Surgical Oncology and the British Association of Surgical Oncology 39, 279-289, 2013.
Kim et al., "Oligonucleotide microarray analysis of distinct gene expression patterns in colorectal cancer tissues harboring BRAF and K-ras mutations.", Carcinogenesis 27(3): 392-404, 2006.
Kinde et al., "Detection and quantification of rare mutations with massively parallel sequencing", Proceedings of the National Academy of Sciences of the United States of America 108, 9530-9535, 2011.
Kinde et al., "FAST-SeqS: a simple and efficient method for the detection of aneuploidy by massively parallel sequencing.", PloS ONE 7:e41162, 2012.
Kinde et al., "TERT promoter mutations occur early in urothelial neoplasia and are biomarkers of early disease and disease recurrence in urine.", Cancer Res 73 :7162-7167, 2013.
Kinde et al., 'Detection and quantification of rare mutations with massively parallel sequencing', PNAS, 2011, 108(23):9530-9535.
Kinde et al., 'Evaluation of DNA from the Papanicolaou test to detect ovarian and endometrial cancers' Science Translational Medicine. vol. 5, Issue 167, Article No. 164ra164, pp. 1-10, 2013.
Kindelberger et al., "Intraepithelial carcinoma of the fimbria and pelvic serous carcinoma: Evidence for a causal relationship.", The American journal of surgical pathology 31: 161-9, 2007.
Kivioja et al., "Counting absolute numbers of molecules using unique molecular identifiers," Nature Methods, vol. 9, No. 1, pp. 72-74, 2011.
Kobayashi et al., "A randomized study of screening for ovarian cancer: a multi center study in Japan.", Int J Gynecol Cancer 18, 414-420, 2008.
Kodaz et al., Frequency of RAS Mutations (KRAS, NRAS, HRAS) in Human Solid Cancer, EJMO, 2017, 1(1):1-7.
Konecny et al., "Activity of the Dual Kinase Inhibitor Lapatinib (GW572016) against HER-2-Overexpressing and Trastuzumab-Treated Breast Cancer Cells", Cancer Res 66: 1630-1639, 2006.
Koopmann et al., "Evaluation of Osteopontin as Biomarker for Pancreatic Adenocarcinoma", Cancer Epidemiol Biomarkers Prev 13(3): 487-491, 2004.
Korpanty et al., "Biomarkers that currently affect clinical practice in lung cancer: EGFR, ALK, MET, ROS-1, and KRAS", Front Oncol. 4: 204, 2014.
Kosuri et al., "Scalable gene synthesis by selective amplification of DNA pools from high-fidelity microchips.", Nat Biotechnol 28: 1295-1299, 2010.
Kou et al., "Benefits and Challenges with Applying Unique Molecular Identifiers in Next Generation Sequencing to Detect Low Frequency Mutations", PLOS ONE., vol. 11, No. 1, p. e0146638, 2016.
Kozarewa et al., "Amplification-free Illumina sequencing-library preparation facilitates improved mapping and assembly of (G+C)-biased genomes", Nature Methods, vol. 6, No. 4, pp. 291-295, 2009.
Kozarewa et al., "Amplification-free library preparation for paired-end illumina sequencing", chapter 18, pp. 257-266, 2011.
Kraystberg et al., "Single- molecuke PCR: an artifact-free PCR approach for the analysis of somatic mutations" Expert Rev. Mol. Diagn. 5(5), 809-815, 2005.
Krystberg et al.,"Single molecule PCR in mtDNA mutational analysis: genuine mutations vs. damage bypass-derived artifacts" NIH Public Access Methods, 46(4): 269-273, 2008.
Krimmel et al., "Ultra-deep sequencing detects ovarian cancer cells in peritoneal fluid and reveals somatic TP53 mutations in noncancerous tissues.", Proc Natl Acad Sci USA 113, 6005-6010, 2016.
Kristjansdottir et al., "Ovarian cyst fluid is a rich proteome resource for detection of new tumor biomarkers", Clinical Proteomics, vol. 9, internal pp. 1-9, 2012.
Kristjansdottir et al., "Potential tumor biomarkers identified in ovarian cyst fluid by quantitative proteomic analysis, iTRAQ.", Clinical proteomics 10, 4, 2013.
Kruger et al., "Numerical aberrations of chromosome 17 and the 9p2 1 locus are independent predictors of tumor recurrence in noninvasive transitional cell carcinoma of the urinary bladder.", Int J Oncol 23 :41-48, 2003.
Kuhn et al., "Identification of Molecular Pathway Aberrations in Uterine Serous Carcinoma by Genome-wide Analyses," Journal of the National Cancer Institute, vol. 104, No. 19, pp. 1503-1513, 2012.

(56) References Cited

OTHER PUBLICATIONS

Kuhn et al., "TP53 mutations in serous tubal intraepithelial carcinoma and concurrent pelvic high grade serous carcinoma-evidence supporting the clonal relationship of the two lesions.", The Journal of pathology, 226: 421-6, 2012.
Kumar et al., "Application of microarray in breast cancer: An overview", J. Pharm. Bioallied Sci. 4(1): 21-26, 2012.
Kumar et al., "Association of mitochondrial copy No. variation and T16189C polymorphism with colorectal cancer in North Indian population.", Tumor Biol, 39: 1010428317740296, 2017.
Kumar et al., "Cell-free mitochondrial DNA copy No. variation in head and neck squamous cell carcinoma: A study of non-invasive biomarker from Northeast India." Tumour Biol. 39: 1010428317736643, 2017.
Kumar et al., "Deep sequencing of multiple regions of glial tumors reveals spatial heterogeneity for mutations in clinically relevant genes.", Genome biology 15, 530, 2014.
Kumar et al., "Serum and Plasma Metabolomic Biomarkers for Lung Cancer", Bioinformation, 13(6); 202-208, 2017.
Kunkel, "The mutational specificity of DNA polymerase-beta during in vitro DNA synthesis.", J Biol Chem 260: 5787-5796, 1985.
Kuppusamy et al., "Proteins are potent biomarkers to detect colon cancer progression", Saudi Journal of Biological Sciences, 24, 1212-1221, 2017.
Kurman et al., "Molecular pathogenesis and extraovarian origin of epithelial ovarian cancer-Shilling the paradigm," Human Pathology, 42, 918-931, 2011.
Kurman et al., "The Dualistic Model of Ovarian Carcinogenesis: Revisited, Revised, and Expanded.", Am J Pathol 186, 733-747, 2016.
Kurman et al., "The origin and pathogenesis of epithelial ovarian cancer; a proposed unifying theory", The American journal of surgical pathology 34, 433-443, 2010.
Kwon et al., "Prophylactic salpingectomy and delayed pophorectomy as an alternative for BRCA mutation carriers.", Obstetrics and gynecology, 121:14-24, 2013.
Laddha et al., "Mutational Landscape of the Essential Autophagy Gene BECN1 in Human Cancers", Molecular cancer research 12: 485-490, 2014.
Laere et al., "cDNA Microarray Analysis of Inflammatory Breast Cancer Signatures", Methods Mol. Biol. 512; 71-98, 2009.
Lai et al., "Population-Based Case-Control Study of Chinese Herbal Products Containing Aristolochic Acid and Urinary Tract Cancer Risk", J Natl Cancer Inst, 102(3): 179-186, 2010.
Lalkhen et al., "Clinical tests; sensitivity and specificity", Continuing Education in Anaesthesia, Critical Care & Pain, vol. 8, No. 6, 221-223, 2008.
Langmead et al., "Fast gapped-read alignment with Bowtie 2", Nature Methods 9: 357-359, 2012.
Leary et al. "Detection of chromosomal alterations in the circulation of cancer patients with whole-genome sequencing," Sci Transl Med, 2012, 4(162):1-21.
Lee et al., "A candidate precursor to serous carcinoma that originates in the distal fallopian tube", The journal of pathology 211, 26-35, 2007.
Lee et al., "Quantification of kinase activity in cell lysates via photopatterned macroporous poly(ethylene glycol) hydrogel arrays in microfluidic channels", Biomed. Microdevices 14: 247-57, 2012.
Lennon et al., "Diagnostic and Therapeutic Response Markers.", Pancreatic Cancer, (Springer New York, New York, NY), pp. 675-701, 2010.
Lennon et al., "The Early Detection of Pancreatic Cancer: What Will It Take to Diagnose and Treat Curable Pancreatic Neoplasia?", Cancer Res 74(13): 3381-3389, 2014.
Levanon et al., "New insights into the pathogenesis of serous ovarian cancer and its clinical impact.", Journal of clinical oncology : official journal of the American Society of Clinical Oncology, 26: 5284-93, 2008.
Levey et al., "Definition and classification of chronic kidney disease: a position statement from Kidney Disease: Improving Global Outcomes (KDIGO).", Kidney Int. 67(6): 2089-100, 2005.
Levey et al., "Using Standardized Serum Creatinine Values in the Modification of Diet in Renal Disease Study Equation for Estimating Glomerular Filtration Rate", Ann Intern Med. 145(4): 247-54, 2006.
Levina et al., "Biological significance of prolactin in gynecologic cancers.", Cancer Res 69(12): 5226-5233, 2009.
Levine et al., "Management of asymptomatic ovarian and other adnexal cysts imaged at US: Society of Radiologists in Ultrasound Consensus Conference Statement", Radiology 256, 943-954, 2010.
Li et al., "DNA Methylation in Peripheral Blood: A Potential Biomarker for Cancer Molecular Epidemiology", J. Epidemoil, 22(5): 384-394, 2012.
Li et al., "Replacing PCR with COLD-PCR enriches variant DNA sequences and redefines the sensitivity of genetic testing", Nat Med 14: 579-584, 2008.
Li et al., "Significant Predictive Factors for Prognosis of Primary Upper Urinary Tract Cancer after Radical Nephroureterectomy in Taiwanese Patients", Eur Ural. 54(5): 1127-1134, 2008.
Li et al., "Toward better understanding of artifacts in variant calling from high-coverage samples.", Bioinformatics 30: 2843-2851, 2014.
Liaw et al., "Classification and Regression by random Forest", R news 2: 18-22, 2001.
Lin et al., "A molecular inversion probe assay for detecting alternative splicing", BMC Genomics 11: 712, 2010.
Lin et al., "Benefits and harms of prostate-specific antigen screening for prostate cancer; an evidence update for the U.S. Preventive Services Task Force.", Ann. Intern. Med. 149: 192-199, 2008.
Lin et al., "Increase sensitivity in detecting superficial, low grade bladder cancer by combination analysis of hypermethylation of E-cadherin, p16, p14, RASSF1A genes in urine.", Ural Oncol 28: 597-602, 2010.
Lin et al., "Thyroid cancer in the thyroid nodules evaluated by ultrasonography and fine-needle aspiration cytology", Thyroid: official journal of the american thyroid association 15, 708-717, 2005.
Lindor et al., Press, "Recommendations for the care of individuals with an inherited predisposition to Lynch syndrome: a systematic review.", JA,HA 296, 1507-1517, 2006.
Linnarsson et al., "Recent advances in DNA sequencing methods— general principles of sample preparation", Experimental cell research., 316, 1339-1343, 2010.
Liotta et al., "The promise of proteomics.", Clin Ady Hematol Oncol 1(8): 460-462, 2003.
Liscia et al., "Prognostic significance of loss of heterozygosity at loci on chromosome 17p13.3-ter in sporadic breast cancer is evidence for a putative tumour suppressor gene", British Journal of Cancer, 80 (5/6) 821-826, 1999.
Liu et al., "Comparison of Next-Generation Sequencing Systems," Journal of Biomedicine and Biotechnology, 2012, 2012(251364) 11 pages.
Liu et al., "Detection of extremely rare alleles by bidirectional pyrophosphorolysis-activated polymerization allele-specific amplification (Bi-PAP-A): measurement of mutation load in mammalian tissues.", Biotechniques 36: 156-166, 2004.
Liu et al., "Digital quantification of gene methylation in stool DNA by emulsion-PCR coupled with hydrogel immobilized bead-array.", Biosens Bioelectron 92: 596-601, 2017.
Livrahi et al., "PARP inhibitors in the management of breast cancer: current data and future prospects.", BMC Medicine 13: 188, 2015.
Locker et al., "ASCO 2006 Update of Recommendations for the Use of Tumor Markers in Gastrointestinal Cancer", J. Clin. Oncol. 24: 5313-5327, 2006.
Lodato et al., "Somatic mutation in single human neurons tracks developmental and transcriptional history.", Science 350, 94-98, 2015.
Lodes et al., "Detection of Cancer with Serum miRNAs on an Oligonucleotide Microarray", PLoS One 4(7): e6229, 2009.
Loh et al., "Ovarian response after laparoscopic ovarian cystectomy for endometriotic cysts in 132 monitored cycles", Fertility and sterility 72, 316-321, 1999.

(56) References Cited

OTHER PUBLICATIONS

Longacre et al., "Recommendations for the reporting of fallopian tube neoplasms.", Hum Pathol., 38: 1160-3, 2007.
Lotan et al., "Sensitivity and Specificity of Commonly Available Bladder Tumor Markers Versus Cytology: Results of a Comprehensive Literature Review and Meta-Analyses", Urology 61: 109-18, 2003.
Lou et al., "Biomarkers for Hepatocellular Carcinoma", Biomark Cancer, 9: 1-9, 2017.
Louseberg et al., "Safety, Efficacy, and Patient Acceptability of Everolimus in the Treatment of Breast Cancer.", Breast Cancer 10: 239-252, 2017.
Lowe et al., "Multiplex Sensing of Protease and Kinase Enzyme Activity via Orthogonal Coupling of Quantum Dot-Peptide Conjugates", ACS nano. 6: 851-7, 2012.
Luria et al., "Mutations of Bacteria from Virus Sensitivity to Virus Resistance." Genetics 28: 491-511, 1943.
Mackay et al., "cDNA microarray analysis of genes associated with ERBB2 (HER2/neu) overexpression in human mammary luminal epithelial cells", Oncogene 22: 2680-2688, 2003.
Mackay et al., "Phase II trial of the histone deacetylase inhibitor belinostat in women with platinum resistant epithelial ovarian cancer and micropapillary (LMP) ovarian tumours.", Eur. J. Cancer 46(9): 1573-1579, 2010.
Madabhushi et al., "DNA damage and its links to neurodegeneration.", Neuron 83, 266-282, 2014.
Makohon-Moore et al., "Limited heterogeneity of known driver gene mutations among the metastases of individual patients with pancreatic cancer", Nat Genet., 49(3): 358-366, 2017.
Malpica et al., "Grading ovarian serous carcinoma using a two-tier system," Am. J. Surg. Pathol. 28, 496-504, 2004.
Mao et al., "The Application of Single Nucleotide Polymorphism Microarrays in Cancer Research", Curr. Genomics 8(4): 219-228, 2007.
Mao, "Recent advances in the molecular diagnosis of lung cancer.", Oncogene 21: 45, 6960-6969, 2002.
Maragh et al., "Evaluation of two mitochondrial DNA biomarkers for prostate cancer detection.", Cancer Biomark., 15: 763-73, 2015.
Marengo et al., "Biomarkers for pancreatic cancer: Recent achievements in proteomics and genomics through classical and multivariate statistical methods," World J. Gastroenterol, 20(37): 13325-13342, Oct. 7, 2014) (Year: 2014).
Marques et al., "A typical glandular cells and cervical cancer: systematic review.", Rev Assoc Af ed Bras 57, 234-238, 2011.
Martinez et al., "Computational optimisation of targeted DNA sequencing for cancer detection," Sci. Rep., 2013, 3(3309):sertp03309 1-8.
Martinez-Onsurbe et al., "Aspiration cytology of 147 adnexal cysts with histologic correlation", Acta. Cytologica 45, 941-947, 2001.
Matei et al., "Epigenetic Resensitization to Platinum in Ovarian Cancer", Cancer Res. 72(9): 2197-2205, 2012.
Matzas et al., "High-fidelity gene synthesis by retrieval of sequence-verified DNA identified using high-throughput pyrosequencing.", Nat Biotechnol 28: 1291-1294, 2010.
Mayr et al., "KRAS and BRAF mutations in ovarian tumors: a comprehensive study of invasive carcinomas, borderline tumors and extraovarian implants", Gyencologie oncology 103, 883-887, 2006.
Mayrand et al., "Human papillomavirus DNA versus Papanicolaou screening tests for cervical cancer.", N. Engl. J. Med. 357, 1579-1588, 2007.
McAlpine et al., "Opportunistic salpingectomy: uptake, risks, and complications of a regional initiative for ovarian cancer prevention.", American journal of obstetrics and gynecology 210: 471 e1-11, 2014.
McCloskey et al., "Encoding PCR products with batch-stamps and barcodes", Biochem Genet 45: 761-767, 2007.
McConechy et al., "Use of mutation profiles to refine the classification of endometrial carcinomas," J. Path, 2012, 228:20-30 and supplementary table, pp. 1-11.

Mcdaniel et al., "Next-Generation Sequencing of Tubal Intraepithelial Carcinomas." JAMA oncology 1: 1128-32, 2015.
McMahon et al., "The HBV drug entecavir—effects on HIV-1 replication and resistance.", N Engl J Med 356: 2614-2621, 2007.
Medeiros et al., "The tubal fimbria is a preferred site for early adenocarcinoma in women with familial ovarian cancer syndrome.", The American journal, vol. 30, issue 2, pp. 230-236, 2006.
Meden et al., "CA 125 in benign gynecological conditions.", Int J Biol A1arkers 13, 231-237, 1998.
Meldrum et al., "Next-Generation Sequencing for Cancer Diagnostics: a Practical Perspective", Clin. Biochem. Rev. 32(4): 177-195, 2011.
Mendivil et al., "Increased incidence of severe gastrointestinal events with first-line paclitaxel, carboplatin, and vorinostat chemotherapy for advanced-stage epithelial ovarian, primary peritoneal, and fallopian tube cancer.", Int. J. Gynecol. Cancer 23(3): 533-539, 2013.
Menon et al., "Ovarian cancer screening-current status, future directions.", Gynecologic oncology 132: 490-5, 2014.
Menon et al., "Risk Algorithm Using Serial Biomarker Measurements Doubles the Number of Screen-Detected Cancers Compared With a Single-Threshold Rule in the United Kingdom Collaborative Trial of Ovarian Cancer Screening.", J Clin Oncol 33, 2062-2071, 2015.
Mermel et al., "GISTIC2.0 facilitates sensitive and confident localization of the targets of focal somatic copy-number alteration in human cancers", Genome biolog 12: R41, 2011.
Metzker et al., "Sequencing technologies—the next generation" Nature reviews, 2010.
Michels et al., "Detection of DNA copy number alterations in cancer by array comparative genomic hybridization.", Genet. Med. 9: 574-584, 2007.
Miller et al., "Phase I trial of alvespimycin (KOS-1022; 17-DMAG) and trastuzumab (T)", J. Clin. Oncol. 25; s1115, 2007.
Miner et al., "Molecular barcodes detect redundancy and contamination in hairpin-bisulfite PCR.", Nucleic Acids Res 32:e135, 2004.
Mirus et al., "Cross-Species Antibody Microarray Interrogation Identifies a 3-Protein Panel of Plasma Biomarkers for Early Diagnosis of Pancreas Cancer", Clin. Cancer Res. 21(7): 1764-1771, 2015.
Misek et al., "Protein Biomarkers for the Early Detection of Breast Cancer", International Journal of Proteomics, vol. 2011, article ID 343582, 9 pages, 2011.
Mishriki et al., "Diagnosis of urologic malignancies in patients with asymptomatic dipstick hematuria; prospective study with 13 years' follow-up.", Urology 71: 13-16, 2008.
Mitchell et al., "Accuracy and survival benefit of cytological prediction of endometrial carcinoma on routine cervical smears.", Int J Gynecol Pathol 12, 34-40, 1993.
Mitra et al., "Digital genotyping and haplotyping with polymerase colonies.", Proc Nadl Acad Sci USA 100: 5926-5931, 2008.
Mizutani et al., "A Novel FRET-Based Biosensor for the Measurement of BCR-ABL Activity and Its Response to Drugs in Living Cells", Clin. Cancer Res. 16: 3964-75, 2010.
Mo et al., "Hyperactivation of Haras oncogene, but not Ink4a/Arf deficiency, triggers bladder tumorigenesis.", J Clin Invest 117: 314-325, 2007.
Moch et al., "The 2016 WHO Classification of Tumours of the Urinary System and Male Genital Organs—Part A: Renal, Penile, and Testicular Tumours", EAU, 70, 93-105, 2016.
Mockler et al., "Applications of DNA tiling arrays for whole-genome analysis", Genomics, 85(1): 1-15, 2005.
Modesitt et al., "A phase II study of vorinostat in the treatment of persistent or recurrent epithelial ovarian or primary peritoneal carcinoma: a Gynecologie Oncology Group study.", 109(2): 182-186, 2008.
Modi et al., "Phase II trial of the Hsp90 inhibitor tanespimycin (Tan) + trastuzumab (T) in patients (pts) with HER2-positive metastatic breast cancer (MBC)", J. Clin Oncol. 26; s1027, 2008.
Moertel et al., "Fluorouracil plus levamisole as effective adjuvant therapy after resection of stage III colon carcinoma: a final report.", Ann Intern Med 122(5): 321-326, 1995.

(56) References Cited

OTHER PUBLICATIONS

Monnat et al., "Nucleotide sequence preservation of human mitochondrial DNA", Proc Natl Acad Sci USA 82: 2895-2899, 1985.
Moonen et al., "UroVysion compared with cytology and quantitative cytology in the surveillance of non-muscle-invasive bladder cancer.", Eur Urol 51: 1275-80, 2007.
Moore et al., "The use of multiple novel tumor biomarkers for the detection of ovarian carcinoma in patients with a pelvic mass.", Gynecologie oncology 108, 402-408, 2008.
Moore et al., "Uterine Papillary Serous Carcinoma", Clin Obstet Gynecol 54: 278-291, 2011.
Moran et al., "Cytologic examination of ovarian cyst fluid for the distinction between benign and malignant tumors", Obstetrics and gynecology 82, 444-446, 1993.
Moyer et al., "Screening for ovarian cancer: U.S. Preventive Services Task Force reaffirmation recommendation statement", Annals of internal medicine 157: 900-904, 2012.
Murtaza et al., "Non-invasive analysis of acquired resistance to cancer therapy by sequencing of plasma DNA", Nature 497, 108-112, 2013.
Nair et al., "Genomic Analysis of Uterine Lavage Fluid Detects Early Endometrial Cancers and Reveals a Prevalent Landscape of Driver Mutations in Women without Histopathologic Evidence of Cancer: A Prospective Cross-Sectional Study", PLoS Med 13: e1002206, 2016.
National Toxicology Program. Aristolochic acids. Rep Carcinog, 12, 45-49, 2011.
Naucler et al., "Human papillomavirus and Papanicolaou tests to screen for cervical cancer.", N Engl J 1\fed 357, 1589-1597, 2007.
Nazarian et al., "Melanomas acquire resistance to B-RAF(V600E) inhibition by RTK or N-RAS upregulation.", Nature 468: 973-977, 2010.
Nazli et al., " The diagnostic importance of CEA and CA 19-9 for the early diagnosis of pancreatic carcinoma.", Hepatogastroenterology 47(36): 1750-1752, 2000.
Netto et al., "Emerging Bladder Cancer Biomarkers and Targets of Therapy.", Urol Clin North Am 43: 63-76, 2016.
Netto et al., "Theranostic and prognostic biomarkers: genomic applications in urological malignancies", Pathology 42: 384-394, 2010.
Netto, "Clinical applications of recent molecular advances in urologic malignancies: No. longer chasing a "mirage"?.", Adv Anat Pathol 20: 175-203, 2013.
Netto, "Molecular biomarkers in urothelial carcinoma of the bladder: are we there yet?.", Nat Rev Urol 9: 41-51, 2011.
Newman et al., "An ultrasensitive method for quantitating circulating tumor DNA with board patient coverage", Nature medicine 20, 548-554, 2014.
Newman et al., 'Integrated digital error suppression for improved detection of circulating tumor DNA', Nature Biotechnology, 2016, 34(5):547-555.
Ng et al., "Significance of endometrial cells in the detection of endometrial carcinoma and its precursors.", Acta cytologica 18, 356-361, 1974.
Ngamruengphong et al., "Preoperative endoscopic ultrasound-guided fine needle aspiration does not impair survival of patients with resected pancreatic cancer.", Gut, 64: 1105-1110, 2015.
Ngan et al., "Abnormal expression and mutation of p53 in cervical cancer—a study at protein, RNA and DNA levels", Denitourin Med, 73: 54-58, 1997.
Nguyen et al., "High prevalence of TERT promoter mutations in micropapillary urothelial carcinoma.", Virchows Arch 469: 427-434, 2016.
Nik et al., "Origin and pathogenesis of pelvic (ovarian, tubal, and primary peritoneal) serous carcinoma.", Annual review of pathology 9: 27-45, 2014.
Niknafs et al., SubClonal Hierarchy Inference from Somatic Mutations: Automatic Reconstruction of Cancer Evolutionary Trees from Multi-region Next Generation Sequencing PLoS computational biology, 11: e1004416, pp. 1-26, 2015.
Nolen et al., "Protein biomarkers of ovarian cancer: the forest and the trees", Future Oncol., 8(1): 55-71, 2012.
O'Brien et al., "Serum CA19-9 is significantly upregulated up to 2 years before diagnosis with pancreatic cancer: implications for early disease detection.", Clin Cancer Res 21(3): 622-631, 2015.
Oda et al., "High Frequency of Coexistent Mutations of PIK3CA and PTEN Genes in Endometrial Carcinoma," Cancer Research, vol. 65, No. 23, pp. 10669-10673, 2005.
Odunsi et al., "Epigenetic potentiation of NY-ESO-1 vaccine therapy in human ovarian cancer", Cancer Immunol. Res. 2(1): 37-49, 2014.
Ogiwara et al., "Unbalanced translocation, a major chromosome alteration causing loss of heterozygosity in human lung cancer.", Oncogene, 27: 4788-97, 2008.
Ottesen et al., "Microfluidic digital PCR enables multigene analysis of individual environmental bacteria.", Science 314: 1464-1467, 2006.
Out et al., "Deep Sequencing to Reveal New Variants in Pooled DNA Samples," Hum. Mutat. 2009, 30:1703-1712.
Paik et al., "A Multigene Assay to Predict Recurrence of Tamoxifen-Treated, Node-Negative Breast Cancer", N. Engl. J. Med. 351: 2817-2826, 2004.
Parameswaran et al., "A pyrosequencing-tailored nucleotide barcode design unveils opportunities for large-scale sample multiplexing.", Nucleic Acids Res 35: e130, 2007.
Pardall, "The blockade of immune checkpoints in cancer immunotherapy", Nat. Rev Cancer 12: 252-264, 2012.
Park et al., "Large-scale clinical validation of biomarkers for pancreatic cancer using a mass spectrometry-based proteomics approach", Oncotarget., 8(26): 42761-42771, 2017.
Parker et al., "Ovarian conservation at the time of hysterectomy and long-term health outcomes in the nurses' health study.", Obstetrics and gynecology, 113: 1027-37, 2009.
Parsons et al., "Mismatch repair deficiency in phenotypically normal human cells", Science 268: 738-740, 1995.
Partridge et al., "Results from four rounds of ovarian cancer screening in a randomized trial.", Obstet Gynecol 113, 775-782, 2009.
Patch et al., "Whole-genome characterization of chemoresistant ovarian cancer.", Nature, 521: 489-94, 2015.
Patel et al., "Endometrial carcinoma detected with SurePath liquid-based cervical cytology: comparison with conventional cytology", Cytopathology, vol. 20, No. 6, pp. 380-387, 2009.
Patz et al., "Panel of serum biomarkers for the diagnosis of lung cancer.", J Clin Oneal 25: 5578-5583, 2007.
Pavlik et al., "Frequency and diposition of ovarian abnormalities followed with serial transvaginal ultrasonography", Obstetrics and gynecology 122, 210-217, 2013.
Pecorelli, "Revised FIGO staging for carcinoma of the vulva, cervix, and endometrium.", Int J Gynaecol Obstet 105, 103-104, 2009.
Pemov et al., "DNA analysis with multiplex microarray-enhanced PCR," Nucleic Acids Res., 2005, 33:2:e11.
Peng et al., "Targeted Single Primer Enrichment Sequencing with Single End Duplex-UMI," Scientific Reports, 2019, 9:4810, 10 pages.
Peng et al., Reducing amplification artifacts in high multiplex amplicon sequencing by using molecular barcodes, BMC Genomics, 2015, 16(589):1-12.
Pengelly et al., "A SNP profiling panel for sample tracking in whole-exome sequencing studies", Genome medicine 5: 89, 2013.
Perets et al., "It's Totally Tubular . . . Riding The New Wave of Ovarian Cancer Research.", Cancer research, 76: 10-7, 2016.
Perets et al., "Transformation of the fallopian tube secretory epithelium leads to high-grade serous ovarian cancer in Brca,Tp53;Pten models.", Cancer cell, 24: 751-65, 2013.
Phallen et al., "Direct detection of early-stage cancers using circulating tumor DNA.", Science translational medicine 9, 2017.
Philips et al., "Targeting HER2-positive breast cancer with trastuzumab-DM1, an antibody-cytotoxic drug conjugate.", Cancer Res 68: 9280-9290, 2008.

(56) References Cited

OTHER PUBLICATIONS

Piccart-Gebhart et al., "Trastuzumab after adjuvant chemotherapy in HER2-positive breast cancer.", N. Engl. J. Med. 353: 1659-1672, 2005.
Piek et al.. "BRCA1/2-related ovarian cancers are of tubal origin: a hypothesis.", Gynecologic oncology, 90: 491, 2003.
Piek et al., "Dysplastic changes in prophylactically removed Fallopian tubes of women predisposed to developing ovarian cancer.", The Journal of pathology, 195: 451-6, 2001.
Pinkel et al., "Array comparative genomic hybridization and its applications in cancer", Nature Genetics, vol. 37, S11-S17, 2005.
Pinsky et al., "Prostate Cancer Screening—A Perspective on the Current State of the Evidence", The New England Journal of Medicine, 376; 13, 1285-1289, 2017.
Powers et al., "Protein analytical assays for diagnosing, monitoring, and choosing treatment for cancer patients.", J. Heathe Eng. 3(4): 503-534, 2015.
Proctor et al., "The promise of telomere length, telomerase activity and its regulation in the translocation-dependent cancer ESFT; clinical challenges and utility" Biochimica et Biophysica Acta, 260-274, 2009.
Qiu et al., "No evidence of clonal somatic genetic alterations in cancer-associated fibroblasts from human breast and ovarian carcinomas.", Nature Genetics, vol. 40, pp. 650-655, 2008.
Quail et al., "A large genome center's improvements to the Illumina sequencing system.", Nat Methods 5:1005-1010, 2008.
Quail et al., "Improved Protocols for the Illumina Genome Analyzer Sequencing System," Current Protocols in Humar Genetics, Supplement 62, pp. 18.2.1-18.2.27, 2009.
Rago et al., "Serial assessment of human tumor burdens in mice by the analysis of circulating DNA.", Cancer Res 67, 9364-9370, 2007.
Rahib et al., "Projecting Cancer Incidence and Deaths to 2030; The Unexpected Burden of Thyroid, Liver, and Pancreas Cancers in the United States", Cancer research 74, 2913-2921, 2014.
Ralla et al., "Nucleic acid-based biomarkers in body fluids of patients with urologie malignancies", Crit Rev Clin Lab Sci 51: 200-231, 2014.
Randerath et al., "Covalent DNA Damage in Tissues of Cigarette Smokers as Determined by 32P-Postlabeling Assay", Journal of the National Cancer Institute 81: 341-347, 1989.
Rebbeck et al., "Prophylactic oophorectomy in Carriers of BRCA 1 or BRCA2 mutations.", The New England journal of medicine, 346: 1616-22, 2002.
Resaei-Matehkolaei et al., Use of Single-enzyme PCR-restriction Digestion Bardode Targeting the Internal Transcribed Spacers (ITS rDNA) to identify Dermatophyte Species, Iranian J. Publ. Health, 2012, 41(3):82-94.
Resta et al., "Phase I study of enzastaurin (ENZ) and bevacizumab (BV) in patients with advanced cancer", J. Clin. Oncol. 26 (May 20 suppl), abstr 3529, 2008.
Ricciuti et al., "Long-Lasting Response to Nivolumab and Immune-Related Adverse Events in a Nonsquamous Metastatic Non-Small Cell Lung Cancer Patient.", J. Thorne Oncol. 12(5): e51-e55, 2017.
Ries et al., SEER Survival Afonograph: Cancer Survival Among Adults: US SEER Program, 1988-2001, Patient and Tumor Characteristics (NIH Pub. No. 07-6215. National Cancer Institute, Bethesda, MD, 2007).
Roach et al., "Analysis of Genetic Inheritance in a Family Quartet by Whole Genome Sequencing", Science 328: 636-639, 2010.
Rodriguez et al., Spectrum of genetic mutations in de novo PUNLMP of the urinary bladder. Virchows Arch, vol. 471, issue 6, pp. 761-767, 2017.
Roh et al., "High-grade fimbrial—Ovarian carcinomas are unified by altered p53, PTEN and PAX2 expression.", Modem pathology, 23: 1316-24, 2010.
Romond et al., "Trastuzumab plus Adjuvant Chemotherapy for Operable HER2-Positive Breast Cancer", N. Engl. J. Med. 353: 1673-1684, 2005.
Rosen et al., "Safety, pharmacokinetics, and efficacy of AMG 706, an oral multikinase inhibitor, in patients with advanced solid tumors.", J. Clin. Oncol. 25: 2369-76, 2007.
Rosenberg et al., "Adoptive cell transfer as personalized immunotherapy for human cancer", Science 348(6230): 62-68, 2015.
Rougemont et al., "Probabilistic base calling of Solexa sequencing data.", BMC Bioinformatics 9:431, 2008.
Roupret et al., "European Association of Urology Guidelines on Upper Urinary Tract Urothelial Cell Carcinoma: 2015 Update", Eur Ural. 68(5): 868-79, 2015.
Rozen et al., "Primer3 on the WWW for general users and for biologist programmers.", Methods Afol Biol 132, 365-386, 2000.
Ryan et al., "Pancreatic adenocarcinoma.", N Engl J Med 371(22); 2140-2141, 2014.
Saltz et al., "Phase II Trial of Sunitinib in Patients With Metastatic Colorectal Cancer After Failure of Standard Therapy", J. Clin. Oncol, 25: 4793-4799, 2007.
Sams et al., "Liquid-based Papanicolaou tests in endometrial carcinoma diagnosis. Performance, error root cause analysis, and quality improvement.", Am J Clin Pathol 137, 248-254, 2012.
Sandhu et al., "The poly(ADP-ribose) polymerase inhibitor niraparib (MK4827) in BRCA mutation carriers and patients with sporadic cancer; a phase 1 dose-escalation trial.", Lancet Oncol 14: 882-92, 2013.
Saraswat et al., "Comparative proteomic profiling of the serum differentiates pancreatic cancer from chronic pancreatitis", Cancer Med., vol. 6, issue 7, 1738-1751, 2017.
Sarkis et al., "Association of PS3 nuclear overexpression and tumor progression in carcinoma in situ of the bladder.", J Urol 152: 388-392, 1994.
Sarkis et al., "Nuclear overexpression ofp53 protein in transitional cell bladder carcinoma: a marker for disease progression,", J Natl Cancer Inst 85:53-59, 1993.
Sarkis et al., "Prognostic value of p53 nuclear overexpression in patients with invasive bladder cancer treated with neoadjuvant MVAC.", J Clin Oncol 13: 1384-1390, 1995.
Sarojini et al., "Early Detection Biomarkers for Ovarian Cancer", J, Oncol. 2012: 709049, 2012.
Sarosdy et al., "Use of a multitarget fluorescence in situ hybridization assay to diagnose bladder cancer in patients with hematuria.", J Urol 176: 44-47, 2006.
Schmeler et al., "Neoadjuvant chemotherapy for low-grade serous carcinoma of the ovary or peritoneum", Gynecologic oncology 108, 510-514, 2008.
Schmidt et al., "Pre-diagnostic metabolite concentrations and prostate cancer risk in 1077 cases and 1077 matched controls in the European Prospective Investigation into Cancer and Nutrition", BMC Med, 15: 122, 14 pages, 2012.
Schmitt et al., "Detection of ultra-rare mutations by next-generation sequencing", PNAS USA 109:14508-14513, 2012.
Schnatz et al., "Clinical significance of atypical glandular cells on cervical cytology.", Obstetrics and gynecology 107, 701-708, 2006.
Schorge et al., "ThinPrep detection of cervical and endometrial adenocarcinoma; a retrospective cohort study.", Cancer 96: 338-43, 2002.
Schroder et al., "Dual-color Proteomic Profiling of Complex Samples with a Microarray of 810 Cancer-related Antibodies",Mol. Cell. Proteomics 9: 1271-80, 2010.
Schulz et al., "Inhibiting the HSP90 chaperone destabilizes macrophage migration inhibitory factor and thereby inhibits breast tumor progression.", J Exp Med 209(2): 275-89, 2012.
Schwienbacher et al., "Abnormal RNA expression of 11p15 imprinted genes and kidney developmental genes in Wilms' tumor.", Cancer Res., 60: 1521-5, 2000.
Scott et al., "Mutations of the TERT promoter are common in basal cell carcinoma and squamous cell carcinoma.", Mod Pathol 27: 516-523, 2014.
Scott, "Niraparib: First Global Approval", Drugs, 77: 1029-1034, 2017.
Screening for ovarian cancer: recommendation statement. U.S. Preventive Services Task Force. Am Fam Physician 71, 759-762, 2005.

(56) References Cited

OTHER PUBLICATIONS

Semrad et al., "Integrating Chemotherapy into the Management of Oligometastatic Colorectal Cancer: Evidence-Based Approach Using Clinical Trial Findings.", Ann Surg Oncol 22(Suppl 3): S855-862, 2015.
Serizawa et al., "Integrated genetic and epigenetic analysis of bladder cancer reveals an additive diagnostic value of FGFR3 mutations and hypermethylation events.", Int J Cancer 129(1):78-87, 2010.
Sethi et al., "Evolving Concept of Cancer Stem Cells: Role of Micro-RNAs and their Implications in Tumor Aggressiveness", J. Carcinog. Mutag, S 1-005, 2011.
Shariat et al., "Gender differences in radical nephroureterectomy for upper tract urothelial carcinoma", World J Ural. 29(4): 481-486, 2011.
Sharma et al., "Risk of epithelial ovarian cancer in asymptomatic women with ultrasound-detected ovarian masses: a prospective cohort study within the UK collaborative trial of ovarian cancer screening (UKCTOCS)", Ultrasound Obstet Gynecol 40: 338-344, 2012.
Sharma et al., "Screening for gynaecological cancers," EJSO, 2006, 32(8):818-824.
Sharpless et al., "Dysplasia associated with atypical glandular cells on cervical cytology.", Obstet Gynecol 105, 494-500, 2005.
Shen et al., "BMN 673, a novel and highly potent PARP1/2 inhibitor for the treatment of human cancers with DNA repair deficiency.", Clin. Cancer Res. 19(18): 5003-5015, 2013.
Shen et al., "Mitochondrial copy number and risk of breast cancer: A pilot study", Mitochondrion, 10: 62-68, 2010.
Shendure et al., "Next-generation DNA sequencing," nature biotechnology, 2008, 26(10):1135-1145.
Sherman et al., "Survival among women with borderline ovarian tumors and ovarian. carcinoma: a population-based analysis" Cancer 100, 1045-1052, 2004.
Shi et al., "A Novel Proximity Assay for the Detection of Proteins and Protein Complexes: Quantitation of HER1 and HER2 Total Protein Expression and Homodimerization in Formalin-fixed, Paraffin-Embedded Cell Lines and Breast Cancer Tissue", Diagnostic molecular pathology: the American journal of surgical pathology, part B: 18: 11-21, 2009.
Shi et al., "LigAmp for sensitive detection of single-nucleotide differences.", Nat Methods 1: 141-147, 2004.
Shibata, "Mutation and epigenetic molecular clocks in cancer.", Carcinogenesis 32: 123-128, 2011.
Shih et al., "Risk factors for recurrence of ovarian boderline tumors", Gynecologie oncology 120, 480-484, 2011.
Shlien et al., "Combined hereditary and somatic mutations of replication error repair genes result in rapid onset of ultra-hypermutated cancers.", Nature genetics 47: 257-262, 2015.
Sidranksy, "Nucleic acid-based methods for the detection of cancer.", Science 278(5340): 1054-9, 1997.
Sidransky et al., Identification of p53 gene mutations in bladder cancers and urine samples. Science 252: 706-709. 1991.
Siegel et al., "Cancer Statistics, 2017.", CA Cancer J Clin 67: 7-30, 2017.
Siegel et al., Cancer statistics, 2015. CA: a cancer journal for clinicians, 65:5-29, 2015.
Singer et al., "Mutations in BRAF and KRAS characterize the development of low-grade ovarian serous carcinoma", Journal of National Cancer Institute, vol. 95, No. 6, pp. 484-486, 2003.
Siravegna et al., "Integrating liquid biopsies into the management of cancer.", Nat Rev Clin Oncol 14, 531-548, 2017.
Skacel et al., "Multitarget Fluorescence In Situ Hybridization Assay Detects Transitional Cell Carcinoma in the Majority of Patients with Bladder Cancer and Atypical or Negative Urine Cytology", J Urol 169: 2101-2105, 2003.
Smith et al., "Epigenetic therapy for the treatment of epithelial ovarian cancer: A clinical review", Gynecol. Oncol, Rep. 20: 81-86, 2017.

Smith et al.,"Transvaginal ultrasound for identifying endometrial abnormality.", Acta Obstet Gynecol Scand 70, 591-594, 1991.
soest.hawaii.edu [online], "Nextera XT DNA Sample Preparation Guide," Illumina, Oct. 1, 2012, retrieved on Sep. 19, 2010, Part# 15031942, Rev. C, retrieved from URL<http://cmore.soest.hawaii.edu/summercourse/2015/documents/Metagenomics_06-22/nextera_xt_sample_preparation_guide_15031942_c.pdf>, 48 pages.
Somlo et al., "Efficacy of the PARP inhibitor (PI) ABT-888 (veliparib [vel]) either with carboplatin (carb) or as a single agent followed by post-progression therapy in combination with carb in patients (pts) with BRCA1- or BRCA2-(BRCA)-associated metastatic breast cancer (MBC)..", J. Clin. Oncol. 31: 1024, 2013.
Song et al., "Prognostic factors in women with synchronous endometrial and ovarian cancers.", Int J Gynecol Cancer 24; 520-527, 2014.
Soria et al., "Epidemiology, diagnosis, preoperative evaluation and prognostic assessment of upper-tract urothelial carcinoma (UTUC)", World J Urol, 35(3), 379-387, 2017.
Sorscher, "Pembrolizumab in Non-Small-Cell Lung Cancer.", N Engl J Med 376, 10: 996-7, 2017.
Soung et al., "Exosomes in Cancer Diagnostics", Cancers 9(1):pii:E8, 2017.
Spalding et al., "Retrospective birth dating of cells in humans.", Cell 122, 133-143, 2005.
Springer et al., "A Combination of Molecular Markers and Clinical Features Improve the Classification of Pancreatic Cysts", Gastroenterology 149(6): 1501-1510, 2015.
Springer et al., "Non-invasive detection of urothelial cancer through the analysis of driver gene mutations and aneuploidy", eLIFE, 7; e32143, 27 pages, 2018.
Steensma et al., "Clonal hematopoiesis of indeterminate potential and its distinction from myelodysplastic syndromes.", Blood 126, 9-16, 2015.
Stem et al., "Mutation of the TERT promoter, switch to active chromatin, and monoallelic TERT expression in multiple cancers.", Genes Dev 29: 2219-2224, 2015.
Stratagene Catalog, "Gene Characterization Kits" 1988, p. 39 only.
Stratton et al., "The cancer genome.", Nature 458: 719-724, 2009.
Stromberg et al., "A high-throughput strategy for protein profiling in cell microarrays using automated image analysis.", Proteomics 7; 2142-50, 2007.
Suh et al., Major clinical research advances in gynecologic cancer in 2011, Journal of Gynecologic Oncology, vol. 23, No. 1, pp. 53-64, 2012.
Sun et al., "Elevated expression of the centromere protein-A(CENP-A)-encoding gene as a prognostic and predictive biomarker in human cancers", Int. J. Cancer, 139, 899-907, 2016.
Sun et al., "Nivolumab effectively inhibit platinum-resistant ovarian cancer cells via induction of cell apoptosis and inhibition of ADAM17 expression", Eur Rey Med Pharmacol Sci 21(6): 1198-1205, 2017.
Sundfeldt et al., "Specific mutant tumor DNA can be detected in ovarian cystic fluid of an unknown ovarian tumor cyst", In: The American Association for Cancer Research, abstract #2839, 2015.
Tabernero et al., "Dose- and Schedule-Dependent Inhibition of the Mammalian Target of Rapamycin Pathway With Everolimus: A Phase I Tumor Pharmacodynamic Study in Patients With Advanced Solid Tumors," J. Clin. Oncol., 2008, 26: 1603-1610.
Tabernero et al., "Phase I study of AZD0530, an oral potent inhibitor of Src kinase: First demonstration of inhibition of Sro activity in human cancers", J. Clin. Oncol. 25: 18S, abstr 3520, 2007.
Takahashi et al., "Clonal and chronological genetic analysis of multifocal cancers of the bladder and upper urinary tract.", Cancer Res 58: 5835-5841, 1998.
Tanase et al., "Prostate cancer proteomics: Current trends and future perspectives for biomarker discovery", Oncotarget., Mar. 14; 8(11): 18497-18512, 2017.
Tang et al., "A phase I study of vorinostat (VOR) in combination with capecitabine (CAP) in patients (pts) with advanced solid tumors", J. Clin. Oncol 26, May 20 suppl; abstr 4027, 2018.
Tao, "Direct intrauterine sampling: the IUMC Endometrial Sampler.", Diagnostic cytopathology 17, 153-159, 1997.

(56) References Cited

OTHER PUBLICATIONS

The 1000 Genomes Project Consortium, "An integrated map of genetic variation from. 1,092 human genomes.", Nature 491: 56-65, 2012.
Thomas et al., "Construction of a 2-Mb resolution BAC microarray for CGH analysis of canine tumors", Genome Res. 15(12): 1831-1837, 2005.
Thomas et al., "Evaluation of serum CEA, CYFRA21-1 and CA125 for the early detection of colorectal cancer using longitudinal preclinical samples.", Br J Cancer 113(2): 268-274, 2015.
Thompson et al., "Winnowing DNA for Rare Sequences: Highly Specific Sequence and Methylation Based Enrichment" PLoS One, 7:e31597, 2012.
Thorpe et al., "Effects of blood collection conditions on ovarian cancer serum markers.", PLoS One 2(12): e1281, 2007.
Thunnissen, "Sputum examination for early detection of lung cancer.", J Clin Pathol 56: 805-810, 2003.
Thyagarajan et al., "Mitochondrial Copy Number is Associated With Colorectal Cancer Risk", Cancer Epidemiol Biomarkers Prev, 21(9): 1574-1581, 2012.
Tindall et al., "Fidelity of DNA synthesis by the Thermus aquaticus DNA polymerase.", Biochemistry 27: 6008-6013, 1988.
Tomasetti et al., "Cancer etiology. Variation in cancer risk among tissues can be explained by the No. of stem cell divisions.", Science 347, 78-81, 2015.
Tomasetti et al., "Half or more of the somatic mutations in cancers of self-renewing tissues originate prior to tumor initiation.", Proceedings of the National Academy of Sciences of the United States of America 110, 1999-2004, 2013.
Tran et al., "Tract embolization with gelatin sponge slurry for prevention of pneumothorax after percutaneous computed tomography-guided lung biopsy.", Cardiovascular and interventional radiology 37, 1546-1553, 2014.
Traut et al., "Cancer of the Uterus: The Vaginal Smear in Its Diagnosis.", Cali. West. Med. 59, 121-122, 1943.
Troiano et al., "Sonographically guided therapeutic aspiration of benign-appearing ovarian cysts and endometriomas," AJR, 1998, 171:1601-1605.
Tsang et al., "KRAS (but not BRAF) mutations in ovarian serous borderline tumour are assocalted with recurrent low-grade serous carcinoma", The Journal of pathology 231, 449-456, 2013.
Tsang et al., "Ultrasound-guided plugged percutaneous biopsy of solid organs in patients with bleeding tendencies.", Hong Kong Medical Journal, 20, 107-112, 2014.
Tsuchiya et al., "Biomarkers for the early diagnosis of hepatocellular carcinoma", World J Gastroenterol., 21(37): 10573-10583, 2015.
Tsuchiya et al., "Collective review of small carcinomas of the pancreas.", Ann Surg 203(1): 77-81, 1986.
Turner et al., "Massively parallel exon capture and library-free resequencing across 16 genomes," Nat. Methods, 2009, 6:315-316.
Turner et al., "Palbociclib in Hormone-Receptor-Positive Advanced Breast Cancer", N Engl J Med 373: 209-219, 2015.
Tutt et al., "Oral poly(ADP-ribose) polymerase inhibitor olaparib in patients with BRCA1 or BRCA2 mutations and advanced breast cancer: a proof-of-concept trial", Lancet 376: 235-44, 2010.
Ueland et al., "Effectiveness of a multivariate index assay in the preoperative assessment of ovarian tumors.", Obstetrics and gynecology 117, 1289-1297, 2011.
Uhlen et al., "Tissue-based map of the human proteome.", Science 347(6220): 1260419, 2015.
Urick et al., "PIK3RI (p85α) Is Somatically Mutated at High Frequency in Primary Endometrial Cancer," Cancer Research, 2011, 71(12):4062-4064.
Vallania et al., High-throughput discovery of rare insertions and deletions in large cohorts. Genome Res 20; 1711-1718, 2010.
Van Beers et al., "Array-CGH and breast cancer", Breast Cancer Res. 8(3): 210, 10 pages, 2006.
Van Dijk et al., "Ten years of next-generation sequencing technology," Trends in Genetics, 2014, 30(9):418-426.
Van Dongen et al., "Analysis of immunoglobulin and T cell receptor genes. Part II: Possibilities and limitations in the diagnosis and management of lymphoproliferative diseases and related disorders.", Clin Chim Acta 198: 93-174, 1991.
Van Nagell et al., "Ovarian cancer screening with annual transvaginal sonography: findings of 25,000 women screened.", Cancer 109, 1887-1896, 2007.
Vansteenkiste et al., "Prospects and progress of atezolizumab in non-small cell lung cancer", Expert Opin Biol Ther 17(6): 781-789, 2017.
Vijg et al., "Somatic mutations, genome mosaicism, cancer and aging", Current opinion in genetics & development 26: 141-149, 2014.
Vogelstein et al., "Cancer genes and the pathways they control.", Nat. Med. 10, 789-799, 2004.
Vogelstein et al., "Cancer genome landscapes", Science 339, 1546-1558, 2013.
Vogelstein et al., "Digital PCR.", Proc NatlAcad Sci US A 96: 9236-9241, 1999.
Vogelstein et al., "The Path to Cancer—Three Strikes and You're Out", N Engl J Med 3 73: 1895-1898, 2015.
Volpe et al., "Techniques, safety and accuracy of sampling of renal tumors by fine needle aspiration and core biopsy", The journal of urology 178, 379-386, 2007.
Waddell et al., "Whole genomes redefine the mutational landscape of pancreatic cancer", Nature 518(7540):495-501, 2015.
Walsh et al., Coexisting ovarian malignancy in young women with endometrial cancer. Obstetrics and gynecology 106, 693-699, 2005.
Wang et al., "Detection of somatic mutations and HPV in the saliva and plasma of patients with head and neck squamous cell carcinomas.", Science translational medicine 7(293): 293ra104, 2015.
Wang et al., "Detection of tumor-derived DNA in cerebrospinal fluid of patients with primary tumors of the brain and spinal cord.", Proc Natl Acad Sci USA 1 12(31): 9704-9709, 2015.
Wang et al., "Diagnostic potential of tumor DNA from ovarian cyst fluid.", Elife 5, 18 pages, 2016.
Wang et al., "Diagnostic significance of urinary long non-coding PCA3 RNA in prostate cancer", Oncotarget, vol. 8, No. 35, 58577-58586, 2017.
Wang et al., "Evaluation of liquid from the Papanicolaou test and other liquid biopsies for the detection of endometrial and ovarian cancers", Sci. Transl. Med., 10, eaap8796, 9 pages, 2018.
Wang et al., "Extracellular interactions and ligand degradation shape the nodal morphogen gradient", Elife 5: 10.7554/eLife.15175, 19 pages, 2016.
Wang et al., "Molecular inversion probes: a novel microarray technology and its application in cancer research.", Cancer Genet 205(7-8): 341-55, 2012.
Wang et al., "Molecular mechanisms and clinical applications of miR-22 in regulating malignant progression in human cancer (Review)", International Journal of Oncology, 50: 345-355, 2017.
Wang et al., "PD-L1 and intratumoral immune response in breast cancer", Oncotarget, vol. 8, (No. 31), pp. 51641-51651, 2017.
Wang et al., "TERT promoter mutations are associated with distant metastases in upper tract urothelial carcinomas and serve as urinary biomarkers detected by a sensitive castPCR.", Oncotarget, 5: 12428-12439, 2014.
Wang et al., "The clinical impact of recent advances in LC-MS for cancer biomarker discovery and verification", Expert Rev Proteomics 13: 99-114, 2016.
Wang et al., "The long non-coding RNA CYTOR drives colorectal cancer progression by interacting with NCL and Sam68", Molecular Cancer, 17: 110, 16 pages, 2018.
Wei et al., "A study of the relationships between oligonucleotide properties and hybridization signal intensities from NimbleGen microarray datasets", Nucleic Acids Res 36(9): 2926-2938, 2008.
Wikipedia.org [online], "Consensus sequence" Oct. 4, 2011, retrieved from URL<https://en.wikipedia.org/w/index.php?title=Consensus_sequence&oldid=423354064>, 2 pages.
Wikipedia.org [online], "Polymerase chain reaction," 2011, retrieved from URL<https://web.archive.org/web/20110203140027/https:en.wikipedia.org/wiki/Polymerase>.

(56) References Cited

OTHER PUBLICATIONS

Wilcox et al., "Chronic pancreatitis pain pattern and severity are independent of abdominal imaging findings.", Clin Gastroenterol Hepatol 13(3):552-560; quiz e528-559,2015.
Woodbury et al., "Elevated HGF Levels in Sera from Breast Cancer Patients Detected Using a Protein Microarray ELISA", J. Proteome Res. 1: 233-237, 2002.
Wu et al., "Endometrial brush biopsy (Tao brush). Histologic diagnosis of 200 cases with complementary cytology: an accurate sampling technique for the detection of endometrial abnormalities.", American journal of clinical pathology 114, 412-418, 2000.
Wu et al., "Recurrent GNAS mutations define an unexpected pathway for pancreatic cyst development.", Sci Transl Afed 3, 92ra66, 2011.
Wu et al., "Whole-exome sequencing of neoplastic cysts of the pancreas reveals recurrent mutations in components of ubiquitin dependent pathways", PNAS 108, 21188-21193, 2011.
Wu, "Urothelial tumorigenesis: a tale of divergent pathways.", Nat Rev Cancer 5: 713-725, 2005.
Xia et al., "Lapatinib Antitumor Activity Is Not Dependent upon Phosphatase and Tensin Homologue Deleted on Chromosome 10 in ErbB2-Overexpressing Breast Cancers", Cancer Res. 67: 1170-1175, 2007.
Xie et al., "Age-related mutations associated with clonal hematopoietic expansion and malignancies.", Nat Med 20(12): 1472-1478, 2014.
Xie et al., "Lnc-PCDH9-13:1 Is a Hypersensitive and Specific Biomarker for Early Hepatocellular Carcinoma", EBiaMedicine, 33, 57-67, 2018.
Xu et al., "Recent advances of highly selective CDK4/6 inhibitors in breast cancer", J Hematol. Oncol. 10(1): 97, 2017.
Yachida et al., "Clinical significance of the genetic landscape of pancreatic cancer and implications for identification of potential long-term survivors.", Clin Cancer Res 18: 6339-6347, 2012.
Yachida et al., "Distant metastasis occurs late during the Jenetic evolution of pancreatic cancer.", Nature, 467: 1114-7, 2010.
Yafi et al., "Prospective analysis of sensitivity and specificity of urinary cytology and other urinary biomarkers for bladder cancer.", Urol Oncol 33 :66.e25-66.e3 1, 2015.
Yamada et al., "It is possible to diagnose malignancy from fluid in cystic ovarian tumors?", European journal of obstetrics, gynecology, and reproductive biology 171, 96-100, 2013.
Yang et al., "Unusually high incidence of upper urinary tract urothelial carcinoma in Taiwan,", Urology, 59( 5), 681-687, 2002.
Yee et al., "Personalized Therapy Tumor Antigen Discovery for Adoptive Cellular Therapy", Cancer J. 23(2): 144-148, 2016.
Young et al., "Clonal haematopoiesis harbouring AML-associated mutations is ubiquitous in healthy adults.", Nat Commun 7, 12484, 2016.
Young et al., Validation of Biomarkers for Early Detection of Pancreatic Cancer: Summary of the Alliance of Pancreatic Cancer Consortia for Biomarkers for Early Detection Workshop., Pancreas, 2018, 47(2):135-141.
Yousem et al., "Pulmonary Langerhans Cell Histiocytosis. Profiling of Multifocal Tumors Using Next-Generation Sequencing Identifies Concordant Occurrence of BRAF V600E Mutations", Chest 143: 1679-1684, 2013.
Yu et al., "LncRNA HCP5 promotes the development of cervical cancer by regulating MACC1 via suppression of microRNA-15a.", Eur. Rev. Med. Pharmacol. Sci., 22: 4812-4819, 2018.
Yu et al., "Long non-coding RNA CACNA1G-AS1 promotes cell migration, invasion and epithelial-mesenchymal transition by HNRNPA2B1 in non-small cell lung cancer", Eur. Rev. Med. Pharmacol. Sci., 22: 993-1002, 2018.
Yun et al., "Biomonitoring of aristolactam-DNA adducts in human tissues using ultra-performance liquid chromatography/ion-trap mass spectrometry.", Chem ResToxicol. 2012 25(5): 1119-31, 2012.
Zack et al., "Pan-cancer patterns of somatic copy No. alteration.", Nature genetics 45: 1134-1140, 2013.

Zaino et al. "Simultaneously Detected Endometrial and Ovarian Carcinomas—A Prospective Clinicopathologic Study of 74 Cases: A Gynecologic Oncology Group Study", Gynecologic oncology 83: 355-362, 2001.
Zamay et al., "Current and Prospective Protein Biomarkers of Lung Cancer", Cancers (Basel), 9(11): 155, 2017.
Zhai et al.," High-grade serous carcinomas arise in the mouse oviduct via defects linked to the human disease.", The Journal of pathology 243, 16-25, 2017.
Zhang "Study of Use of Liquid-based Cytologic Test in Cervical Cancer and Endometrial Carcinoma Screening," China Master Dissertations Full-text Database, No. 8. pp. 4-28, 2005(with English translation).
Zhang et al., "Analysis of the complex interaction of CDR1as-miRNA-protein and detection of its novel role in melanoma", Oncology Letters, 16: 1219-1225, 2018.
Zhang et al., "LncRNA DQ786243 expression as a biomarker for assessing prognosis in patients with gastric cancer," Eur, Rev. Med. Pharmacol Sci., 22: 2304-2309, 2018.
Zhang et al., "LneRNA H19 regulates the expression of its target gene HOXA10 in endometrial carcinoma through competing with miR-612.", Eur. Rev. Med. Pharmacol, Sci., 22: 4820-4827, 2018.
Zhang et al., "The cytomorphological features of low-grade urothelial neoplasms vary by specimen type.", Cancer Cytopathol 124: 552-564, 2016.
Zhao et al., "Histologic follow-up results in 662 patients with Pap test findings of atypical glandular cells: results from a large academic womens hospital laboratory employing sensitive screening methods.", Gynecologic oncology 114, 383-389, 2009.
Zhou et al., "Identifying markers for pancreatic cancer by gene expression analysis.", Cancer Epidemiol Biomarkers Prev 7(2): 109-112, 1998.
Zilbermann et al., "Genome-wide analysis of Dna methylation patterns" Development 134, 2007.
Zimmermann et al., "Digital PCR: a powerful new tool for noninvasive prenatal diagnosis?", Prenat Diagn 28: 1087-1093, 2008.
Zou et al., "More valuable than platinum: first-line penibrolizumab in advanced stage non-small-cell lung cancer.", Ann Oncol 28(4): 685-687, 2017.
Campbell et al., "Identification of somatically acquired rearrangements in cancer using genome-wide massively parallel paired-end sequencing," Nature Genetics, June, vol. 40, No. 6, pp. 722-729 (Year: 2008).
Gu et al., "Preparation of reduced representation bisulfite sequencing libraries for genome-scale DNA methylation profiling," Nature Protocols, Published on-line March, vol. 6, No. 4, pp. 468-481 (Year: 2011).
International Preliminary Report on Patentability in International Appln. No. PCT/US2017/028013, mailed on Oct. 25, 2018, 14 pages.
International Search Report and Written Opinion in International Appln. No. PCT/US2017/028013, mailed on Dec. 1, 2017, 20 pages.
Meyerson et al., "Advances in understanding cancer genomes through second-generation sequencing," Nature Reviews: Genetics, October, vol. 11, pp. 685-696. (Year: 2010).
Skerra, "Phosphorothioate primers improve the amplification of DNA sequences by DNA polymerases with proofreading activity," Nucleic Acids Res., Jul. 25, 1992, 20(14):3551-3554.
Rothberg et al., "The development and impact of 454 Sequencing," Nature Biotechnology, vol. 26, No. 10, pp. 1117-1124 (Year: 2008).
Zhao et al., "Massively parallel display of genomic DNA fragments by rolling-circle amplification and strand displacement amplification on chip," Talanta, vol. 82, pp. 477-482. (Year: 2010).
Lo et al., "Next-Generation Sequencing of Plasma/Serum DNA: An Emerging Research and Molecular Diagnostic Tool," Clinical Chemistry, vol. 55, pp. 607-608. (Year: 2009).

\* cited by examiner

SAFE SEQUENCING SYSTEM

CLAIM OF PRIORITY

This application is a continuation of U.S. patent application Ser. No. 17/837,591, filed on Jun. 10, 2022, which is a continuation of U.S. patent application Ser. No. 17/324,380, filed on May 19, 2021, now U.S. Pat. No. 11,453,913, which is a continuation of U.S. patent application Ser. No. 15/240,034, filed on Aug. 18, 2016, now U.S. Pat. No. 11,180,803, which is a divisional of U.S. patent application Ser. No. 15/090,773, filed on Apr. 5, 2016, which is a divisional application of Ser. No. 14/814,030 filed Jul. 30, 2015, now U.S. Pat. No. 9,487,829, which is a divisional of Ser. No. 14/111,715 filed Apr. 29, 2014, now U.S. Pat. No. 9,476,095, which is a 371 International Application of PCT/US2012/033207 filed Apr. 12, 2012, which claims priority to U.S. Provisional Application No. 61/484,482 filed May 10, 2011 and U.S. Provisional Application No. 61/476,150 filed on Apr. 15, 2011, the entire contents of each of which are hereby incorporated by reference.

GOVERNMENT SUPPORT CLAUSE

This invention was made with government support under grant number CA062924, CA057345, CA043460, HHSN261004433009C awarded by the National Institutes of Health. The government has certain rights in the invention.

SEQUENCE LISTING

This application contains a Sequence Listing that has been submitted electronically as an XML file named "44807-0017010_SL_ST26.XML." The XML file, created on Nov. 13, 2023, is 74,279 bytes in size. The material in the XML file is hereby incorporated by reference in its entirety.

TECHNICAL FIELD OF THE INVENTION

This invention is related to the area of nucleic acid sequencing. In particular, it relates to manipulative and analytic steps for analyzing and verifying the products of low frequency events.

BACKGROUND OF THE INVENTION

Genetic mutations underlie many aspects of life and death—through evolution and disease, respectively. Accordingly, their measurement is critical to several fields of research. Luria and Delbruck's classic fluctuation analysis is a prototypic example of the insights into biological processes that can be gained simply by counting the number of mutations in carefully controlled experiments (1). Counting de novo mutations in humans, not present in their parents, have similarly led to new insights into the rate at which our species can evolve (2, 3). Similarly, counting genetic or epigenetic changes in tumors can inform fundamental issues in cancer biology (4). Mutations lie at the core of current problems in managing patients with viral diseases such as AIDS and hepatitis by virtue of the drug-resistance they can cause (5, 6). Detection of such mutations, particularly at a stage prior to their becoming dominant in the population, will likely be essential to optimize therapy. Detection of donor DNA in the blood of organ transplant patients is an important indicator of graft rejection and detection of fetal DNA in maternal plasma can be used for prenatal diagnosis in a non-invasive fashion (7, 8). In neoplastic diseases, which are all driven by somatic mutations, the applications of rare mutant detection are manifold; they can be used to help identify residual disease at surgical margins or in lymph nodes, to follow the course of therapy when assessed in plasma, and perhaps to identify patients with early, surgically curable disease when evaluated in stool, sputum, plasma, and other bodily fluids (9-11).

These examples highlight the importance of identifying rare mutations for both basic and clinical research. Accordingly, innovative ways to assess them have been devised over the years. The first methods involved biologic assays based on prototrophy, resistance to viral infection or drugs, or biochemical assays (1, 12-18). Molecular cloning and sequencing provided a new dimension to the field, as it allowed the type of mutation, rather than simply its presence, to be identified (19-24). Some of the most powerful of these newer methods are based on Digital PCR, in which individual molecules are assessed one-by-one (25). Digital PCR is conceptually identical to the analysis of individual clones of bacteria, cells, or virus, but is performed entirely in vitro with defined, inanimate reagents. Several implementations of Digital PCR have been described, including the analysis of molecules arrayed in multi-well plates, in polonies, in microfluidic devices, and in water-in-oil emulsions (25-30). In each of these technologies, mutant templates are identified through their binding to oligonucleotides specific for the potentially mutant base.

Massively parallel sequencing represents a particularly powerful form of Digital PCR in that hundreds of millions of template molecules can be analyzed one-by-one. It has the advantage over conventional Digital PCR methods in that multiple bases can be queried sequentially and easily in an automated fashion. However, massively parallel sequencing cannot generally be used to detect rare variants because of the high error rate associated with the sequencing process. For example, with the commonly used Illumina sequencing instruments, this error rate varies from ~1% (31, 32) to ~0.05% (33, 34), depending on factors such as the read length (35), use of improved base calling algorithms (36-38) and the type of variants detected (39). Some of these errors presumably result from mutations introduced during template preparation, during the pre-amplification steps required for library preparation and during further solid-phase amplification on the instrument itself. Other errors are due to base mis-incorporation during sequencing and base-calling errors. Advances in base-calling can enhance confidence (e.g., (36-39)), but instrument-based errors are still limiting, particularly in clinical samples wherein the mutation prevalence can be 0.01% or less (11). In the work described below, we show how templates can be prepared and the sequencing data obtained from them can be more reliably interpreted, so that relatively rare mutations can be identified with commercially available instruments.

There is a continuing need in the art to improve the sensitivity and accuracy of sequence determinations for investigative, clinical, forensic, and genealogical purposes.

SUMMARY OF THE INVENTION

According to one aspect of the invention a method analyzes nucleic acid sequences. A unique identifier (UID) nucleic acid sequence is attached to a first end of each of a plurality of analyte nucleic acid fragments to form uniquely identified analyte nucleic acid fragments. Nucleotide sequence of a uniquely identified analyte nucleic acid fragment is redundantly determined, wherein determined nucleotide sequences which share a UID form a family of members. A nucleotide sequence is identified as accurately representing an analyte nucleic acid fragment when at least 1% of members of the family contain the sequence.

According to another aspect of the invention a method analyzes nucleic acid sequences. A unique identifier sequence (UID) is attached to a first end of each of a plurality of analyte DNA fragments using at least two cycles of amplification with first and second primers to form uniquely identified analyte DNA fragments. The UIDs are in excess of the analyte DNA fragments during amplification. The first primers comprise a first segment complementary to a desired amplicon; a second segment containing the UID; and a third segment containing a universal priming site for subsequent amplification. The second primers comprise a universal priming site for subsequent amplification. Each cycle of amplification attaches one universal priming site to a strand. The uniquely identified analyte DNA fragments are amplified to form a family of uniquely identified analyte DNA fragments from each uniquely identified analyte DNA fragment. Nucleotide sequences of a plurality of members of the family are determined.

Another aspect of the invention is a method to analyze DNA using endogenous unique identifier sequences (UIDs). Fragmented analyte DNA is obtained comprising fragments of 30 to 2000 bases, inclusive. Each end of a fragment forms an endogenous UID for the fragment. Adapter oligonucleotides are attached to ends of the fragments to form adapted fragments. Fragments representing one or more selected genes are optionally enriched by means of capturing a subset of the fragments using capture oligonucleotides complementary to selected genes in the analyte DNA or by amplifying fragments complementary to selected genes. The adapted fragments are amplified using primers complementary to the adapter oligonucleotides to form families of adapted fragments. Nucleotide sequence is determined of a plurality of members of a family. Nucleotide sequences of the plurality of members of the family are compared. A nucleotide sequence is identified as accurately representing an analyte DNA fragment when at least a 1% of members of the family contain the sequence.

Still another aspect of the invention is a composition comprising population of primer pairs, wherein each pair comprises a first and second primer for amplifying and identifying a gene or gene portion. The first primer comprises a first portion of 10-100 nucleotides complementary to the gene or gene portion and a second portion of 10 to 100 nucleotides comprising a site for hybridization to a third primer. The second primer comprises a first portion of 10-100 nucleotides complementary to the gene or gene portion and a second portion of 10 to 100 nucleotides comprising a site for hybridization to a fourth primer. Interposed between the first portion and the second portion of the second primer is a third portion consisting of 2 to 4000 nucleotides forming a unique identifier (UID). The unique identifiers in the population have at least 4 different sequences. The first and second primers are complementary to opposite strands of the gene or gene portion. A kit may comprise the population of primers and the third and fourth primers complementary to the second portions of each of the first and second primers.

These and other embodiments which will be apparent to those of skill in the art upon reading the specification provide the art with tools and methods for sensitively and accurately determining nucleic acid features or sequences.

DETAILED DESCRIPTION OF THE INVENTION

Figure 1:
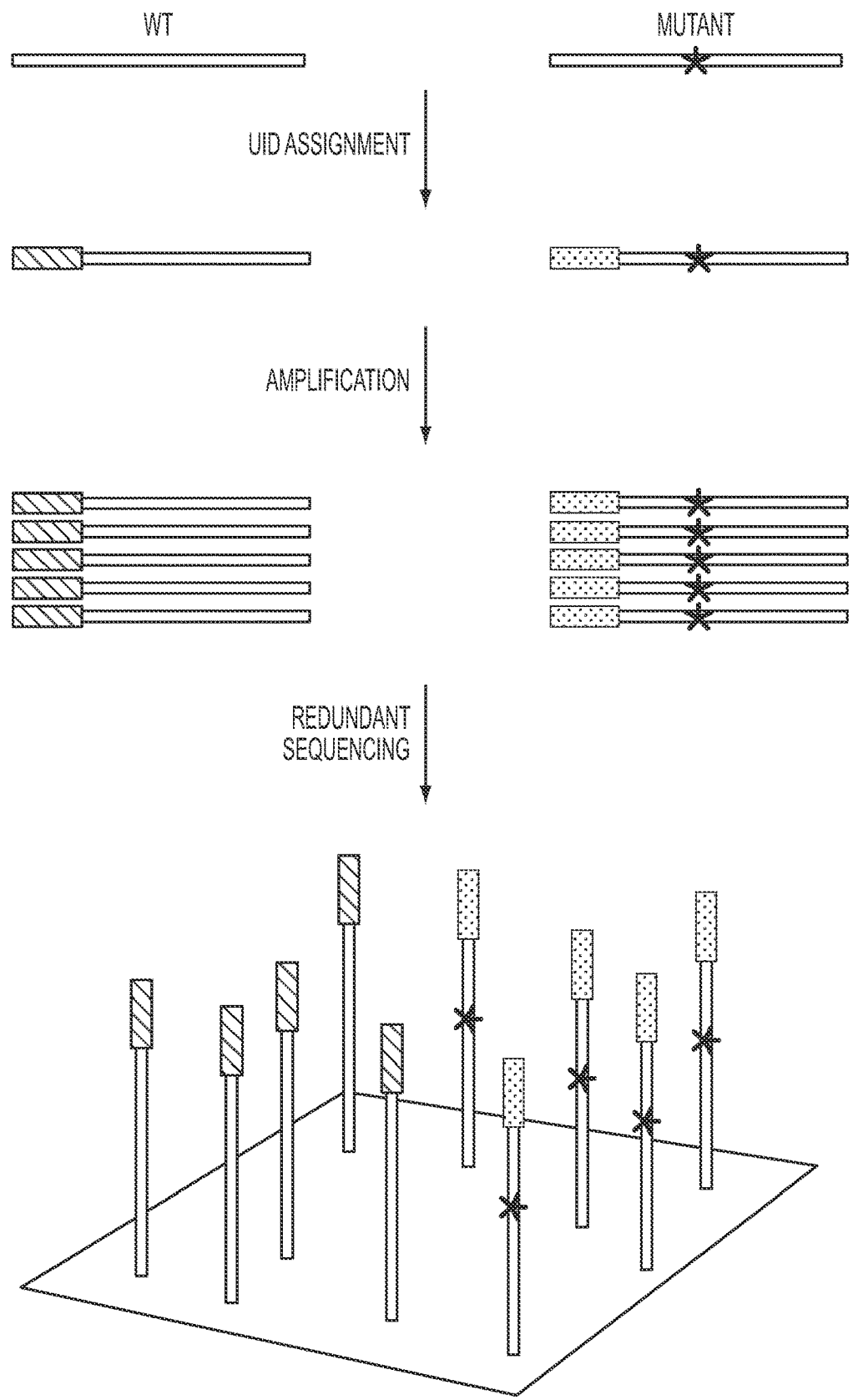
FIG. 1. Essential Elements of Safe-SeqS. In the first step, each fragment to be analyzed is assigned a unique identification (UID) sequence (metal hatch or stippled bars). In the second step, the uniquely tagged fragments are amplified, producing UID-families, each member of which has the same UID. A super-mutant is defined as a UID-family in which ≥95% of family members have the same mutation.

The inventors have developed an approach, called "Safe-SeqS" (from Safe-Sequencing System). In one embodiment it involves two basic steps (FIG. 1). The first is the assignment of a Unique Identifier (UID) to each nucleic acid template molecule to be analyzed. The second is the amplification of each uniquely tagged template, so that many daughter molecules with the identical sequence are generated (defined as a UID-family). If a mutation pre-existed in the template molecule used for amplification, that mutation should be present in a certain proportion, or even all, of daughter molecules containing that UID (barring any subsequent replication or sequencing errors). A UID-family in which every family member (or a certain predetermined proportion) has an identical mutation is called a "super-mutant." Mutations not occurring in the original templates, such as those occurring during the amplification steps or through errors in base-calling, should not give rise to super-mutants, i.e., will not be present at the pre-determined frequency in a UID family. In other embodiments, amplification is not necessary.

The approach can be employed for any purpose where a very high level of accuracy and sensitivity is required from sequence data. As shown below, the approach can be used to assess the fidelity of a polymerase, the accuracy of in vitro synthesized nucleic acid synthesis, and the prevalence of mutations in nuclear or mitochondrial nucleic acids of normal cells. The approach may be used to detect and/or quantify mosaicsm and somatic mutations. Fragments of nucleic acids may be obtained using a random fragment forming technique such as mechanical shearing, sonicating, or subjecting nucleic acids to other physical or chemical stresses. Fragments may not be strictly random, as some sites may be more susceptible to stresses than others. Endonucleases that randomly or specifically fragment may also be used to generate fragments. Size of fragments may vary, but desirably will be in ranges between 30 and 5,000 basepairs, between 100 and 2,000, between 150 and 1,000, or within ranges with different combinations of these endpoints. Nucleic acids may be, for example, RNA or DNA. Modified forms of RNA or DNA may also be used.

Attachment of an exogenous UID to an analyte nucleic acids fragment may be performed by any means known in the art, including enzymatic, chemical, or biologic. One means employs a polymerase chain reaction. Another means employs a ligase enzyme. The enzyme may be mammalian or bacterial, for example. Ends of fragments may be repaired prior to joining using other enzymes such as Klenow Fragment of T4 DNA Polymerase. Other enzymes which may be used for attaching are other polymerase enzymes. An UID may be added to one or both ends of the fragments. A UID may be contained within a nucleic acid molecule that contains other regions for other intended functionality. For example, a universal priming site may be added to permit later amplification. Another additional site may be a region of complementarity to a particular region or gene in the analyte nucleic acids. A UID may be from 2 to 4,000, from 100 to 1000, from 4 to 400, bases in length, for example.

UIDs may be made using random addition of nucleotides to form a short sequence to be used as an identifier. At each position of addition, a selection from one of four deoxyribonucleotides may be used. Alternatively a selection from one of three, two, or one deoxyribonucleotides may be used. Thus the UID may be fully random, somewhat random, or non-random in certain positions. Another manner of making UIDs utilizes pre-determined nucleotides assembled on a chip. In this manner of making, complexity is attained in a planned manner. It may be advantageous to attach a UID to each end of a fragment, increasing the complexity of the UID population on fragments.

A cycle of polymerase chain reaction for adding exogenous UID refers to the thermal denaturation of a double stranded molecule, the hybridization of a first primer to a resulting single strand, the extension of the primer to form a new second strand hybridized to the original single strand. A second cycle refers to the denaturation of the new second strand from the original single strand, the hybridization of a second primer to the new second strand, and the extension of the second primer to form a new third strand, hybridized to the new second strand. Multiple cycles may be required to increase efficiency, for example, when analyte is dilute or inhibitors are present.

In the case of endogenous UIDs, adapters can be added to the ends of fragments by ligation. Complexity of the analyte fragments can be decreased by a capture step, either on a solid phase or in liquid step. Typically the capture step will employ hybridization to probes representing a gene or set of genes of interest. If on a solid phase, non-binding fragments are separated from binding fragments. Suitable solid phases known in the art include filters, membranes, beads, columns, etc. If in a liquid phase, a capture reagent can be added which binds to the probes, for example through a biotin-avidin type interaction. After capture, desired fragments can be eluted for further processing. The order of adding adapters and capturing is not critical. Another means of reducing the complexity of the analyte fragments involves amplification of one or more specific genes or regions. One way to accomplish this is to use inverse PCR. Primers can be used which are gene-specific, thus enriching while forming libraries. Optionally, the gene-specific primers can contain grafting sequences for subsequent attachment to a massively parallel sequencing platform.

Because endogenous UIDs provide a limited number of unique possibilities, depending on the fragment size and sequencing read length, combinations of both endogenous and exogenous UIDs can be used. Introducing additional sequences when amplifying would increase the available UIDs and thereby increase sensitivity. For example, before amplification, the template can be split into 96 wells, and 96 different primers could be used during the amplification.

This would effectively increase the available UIDs 96-fold, because up to 96 templates with the same endogenous UID could be distinguished. This technique can also be used with exogenous UIDs, so that each well's primers adds a unique, well-specific sequence to the amplification products. This can improve the specificity of detection of rare templates.

Amplification of fragments containing a UID can be performed according to known techniques to generate families of fragments. Polymerase chain reaction can be used. Other amplification methods can also be used, as is convenient. Inverse PCR may be used, as can rolling circle amplification. Amplification of fragments typically is done using primers that are complementary to priming sites that are attached to the fragments at the same time as the UIDs. The priming sites are distal to the UIDs, so that amplification includes the UIDs. Amplification forms a family of fragments, each member of the family sharing the same UID. Because the diversity of UIDs is greatly in excess of the diversity of the fragments, each family should derive from a single fragment molecule in the analyte. Primers used for the amplification may be chemically modified to render them more resistant to exonucleases. One such modification is the use of phosphorothioate linkages between one or more 3' nucleotides. Another employs boranophosphates.

Family members are sequenced and compared to identify any divergencies within a family. Sequencing is preferably performed on a massively parallel sequencing platform, many of which are commercially available. If the sequencing platform requires a sequence for "grafting," i.e., attachment to the sequencing device, such a sequence can be added during addition of UIDs or adapters or separately. A grafting sequence may be part of a UID primer, a universal primer, a gene target-specific primer, the amplification primers used for making a family, or separate. Redundant sequencing refers to the sequencing of a plurality of members of a single family.

A threshold can be set for identifying a mutation in an analyte. If the "mutation" appears in all members of a family, then it derives from the analyte. If it appears in less than all members, then it may have been introduced during the analysis. Thresholds for calling a mutation may be set, for example, at 1%, 5%, 10%, 20%, 30%, 40%, 50%, 60%, 70%, 80%, 90%, 95%, 97%, 98%, or 100%. Thresholds will be set based on the number of members of a family that are sequenced and the particular purpose and situation.

In some embodiments, prior to amplification, the analyte DNA is treated with bisulfite to convert unmethylated cytosine bases to uracil. In some embodiments the number of families representing a first analyte DNA fragment is compared to number of families representing a second analyte DNA fragment to determine a relative concentration of a first analyte DNA fragment to a second analyte DNA fragment in the plurality of analyte DNA fragments.

Populations of primer pairs are used to attach exogenous UIDs. The first primer comprises a first portion of 10-100 nucleotides complementary to the gene or gene portion and a second portion of 10 to 100 nucleotides comprising a site for hybridization to a third primer. The second primer comprises a first portion of 10-100 nucleotides complementary to the gene or gene portion and a second portion of 10 to 100 nucleotides comprising a site for hybridization to a fourth primer. Interposed between the first portion and the second portion of the second primer is a third portion consisting of 2 to 4,000 nucleotides forming a unique identifier (UID). The unique identifiers in the population have at least 4, at least 16, at least 64, at least 256, at least 1,024, at least 4,096, at least 16,384, at least 65,536, at least 262,144, at least 1,048,576, at least 4,194,304, at least 16,777,216, or at least 67,108,864 different sequences. The first and second primers are complementary to opposite strands of the gene or gene portion. A kit can be made containing both the primers for attaching exogenous UIDs as well as amplification primers, i.e., the third and fourth primers complementary to the second portions of each of the first and second primers. The third and fourth primers can optionally contain additional grafting or indexing sequences. The UID may comprise randomly selected sequences, pre-defined nucleotide sequences, or both randomly selected sequences and pre-defined nucleotides. If both, these can be joined together in blocks or interspersed.

The methods of analysis can be used to quantitate as well as to determine a sequence. For example, the relative abundance of two analyte DNA fragments may be compared. The results described below in the examples demonstrate that the Safe-SeqS approach can substantially improve the accuracy of massively parallel sequencing (Tables 1 and 2). It can be implemented through either endogenous or exogenously introduced UIDs and can be applied to virtually any sample preparation workflow or sequencing platform. As demonstrated here, the approach can easily be used to identify rare mutants in a population of DNA templates, to measure polymerase error rates, and to judge the reliability of oligonucleotide syntheses. One of the advantages of the strategy is that it yields the number of templates analyzed as well as the fraction of templates containing variant bases. Previously described in vitro methods for the detection of small numbers of template molecules (e.g., (29, 50)) allow the fraction of mutant templates to be determined but cannot determine the number of mutant and normal templates in the original sample.

It is of interest to compare Safe-SeqS to other approaches for reducing errors in next-generation sequencing. As mentioned above, in the background of the invention, sophisticated algorithms to increase the accuracy of base-calling have been developed (e.g., (36-39)). These can certainly reduce false positive calls, but their sensitivity is still limited by artifactual mutations occurring during the PCR steps required for library preparation as well as by (a reduced number of) base-calling errors. For example, the algorithm employed in the current study used very stringent criteria for base-calling and was applied to short read-lengths, but was still unable to reduce the error rate to less than an average of $2.0 \times 10^{-4}$ errors/bp. This error frequency is at least as low as those reported with other algorithms. To improve sensitivity further, these base-calling improvements can be used together with Safe-SeqS. Travers et al. have described another powerful strategy for reducing errors (51). With this technology, both strands of each template molecule are sequenced redundantly after a number of preparative enzymatic steps. However, this approach can only be performed on a specific instrument. Moreover, for many clinical applications, there are relatively few template molecules in the initial sample and evaluation of nearly all of them is required to obtain the requisite sensitivity. The approach described here with exogenously introduced UIDs (FIG. 3) fulfills this requirement by coupling the UID assignment step with a subsequent amplification in which few molecules are lost. Our endogenous UID approaches (FIG. 2 and FIG. 5) and the one described by Travers et al. are not ideally suited for this purpose because of the inevitable losses of template molecules during the ligation and other preparative steps.

How do we know that the mutations identified by conventional analyses in the current study represent artifacts rather than true mutations in the original templates? Strong evidence supporting this is provided by the observation that the mutation prevalence in all but one experiment was similar—$2.0 \times 10^{-4}$ to $2.4 \times 10^{-4}$ mutations/bp (Tables 1 and 2). The exception was the experiment with oligonucleotides synthesized from phosphoramidites, in which the error of the synthetic process was apparently higher than the error rate of conventional Illumina analysis when used with stringent base-calling criteria. In contrast, the mutation prevalence of Safe-SeqS varied much more, from 0.0 to $1.4 \times 10^{-5}$ mutations/bp, depending on the template and experiment. Moreover, the mutation prevalence measured by Safe-SeqS in the most controlled experiment, in which polymerase fidelity was measured (Table 2A), was almost identical to that predicted from previous experiments in which polymerase fidelity was measured by biological assays. Our measurements of mutation prevalence in the DNA from normal cells are consistent with some previous experimental data. However, estimates of these prevalences vary widely and may depend on cell type and sequence analyzed (see SI text). We therefore cannot be certain that the few mutations revealed by Safe-SeqS represented errors occurring during the sequencing process rather than true mutations present in the original DNA templates. Potential sources of error in the Safe-SeqS process are described in the SI text.

Another potential application of Safe-SeqS is the minimization of PCR contamination, a serious problem for clinical laboratories. With endogenous or exogenous UID assignment, the UIDs of mutant templates can simply be compared to those identified in prior experiments; the probability that the same mutation from two independent samples would have the same UID in different experiments is negligible when mutations are infrequent. Additionally, with exogenous UIDs, a control experiment with the same template but without the UID assigning PCR cycles (FIG. 3) can ensure that no DNA contamination is present in that template preparation; no template should be amplified in the absence of UID assignment cycles and thus no PCR product of the proper size should be observed.

Like all techniques, Safe-SeqS has limitations. For example, we have demonstrated that the exogenous UIDs strategy can be used to analyze a single amplicon in depth. This technology may not be applicable to situations wherein multiple amplicons must be analyzed from a sample containing a limited number of templates. Multiplexing in the UID assignment cycles (FIG. 3) may provide a solution to this challenge. A second limitation is that the efficiency of amplification in the UID assignment cycles is critical for the success of the method. Clinical samples may contain inhibitors that reduce the efficiency of this step. This problem can presumably be overcome by performing more than two cycles in the UID assignment PCR step (FIG. 3), though this would complicate the determination of the number of templates analyzed. The specificity of Safe-SeqS is currently limited by the fidelity of the polymerase used in the UID assignment PCR step, i.e., $8.8 \times 10^{-7}$ mutations/bp in its current implementation with two cycles. Increasing the number of cycles in the UID assignment PCR step to five would decrease the overall specificity to $\sim 2 \times 10^{-6}$ mutations/bp. However, this specificity can be increased by requiring more than one super-mutant for mutation identification—the probability of introducing the same artifactual mutation twice or three times would be exceedingly low ($[2 \times 10^{-6}]^2$ or $[2 \times 10^{-6}]^3$, respectively). In sum, there are several simple ways to perform Safe-SeqS variations and analysis variations to realize the needs of specific experiments.

Luria and Delbruck, in their classic paper in 1943, wrote that their "prediction cannot be verified directly, because what we observe, when we count the number of resistant bacteria in a culture, is not the number of mutations which have occurred but the number of resistant bacteria which have arisen by multiplication of those which mutated, the amount of multiplication depending on how far back the mutation occurred." The Safe-SeqS procedure described here can verify such predictions because the number as well as the time of occurrence of each mutation can be estimated from the data, as noted in the experiments on polymerase fidelity. In addition to templates generated by polymerases in vitro, the same approach can be applied to DNA from bacteria, viruses, and mammalian cells. We therefore expect that this strategy will provide definitive answers to a variety of important biomedical questions.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

Example 1—Endogenous UIDs

Figure 2:
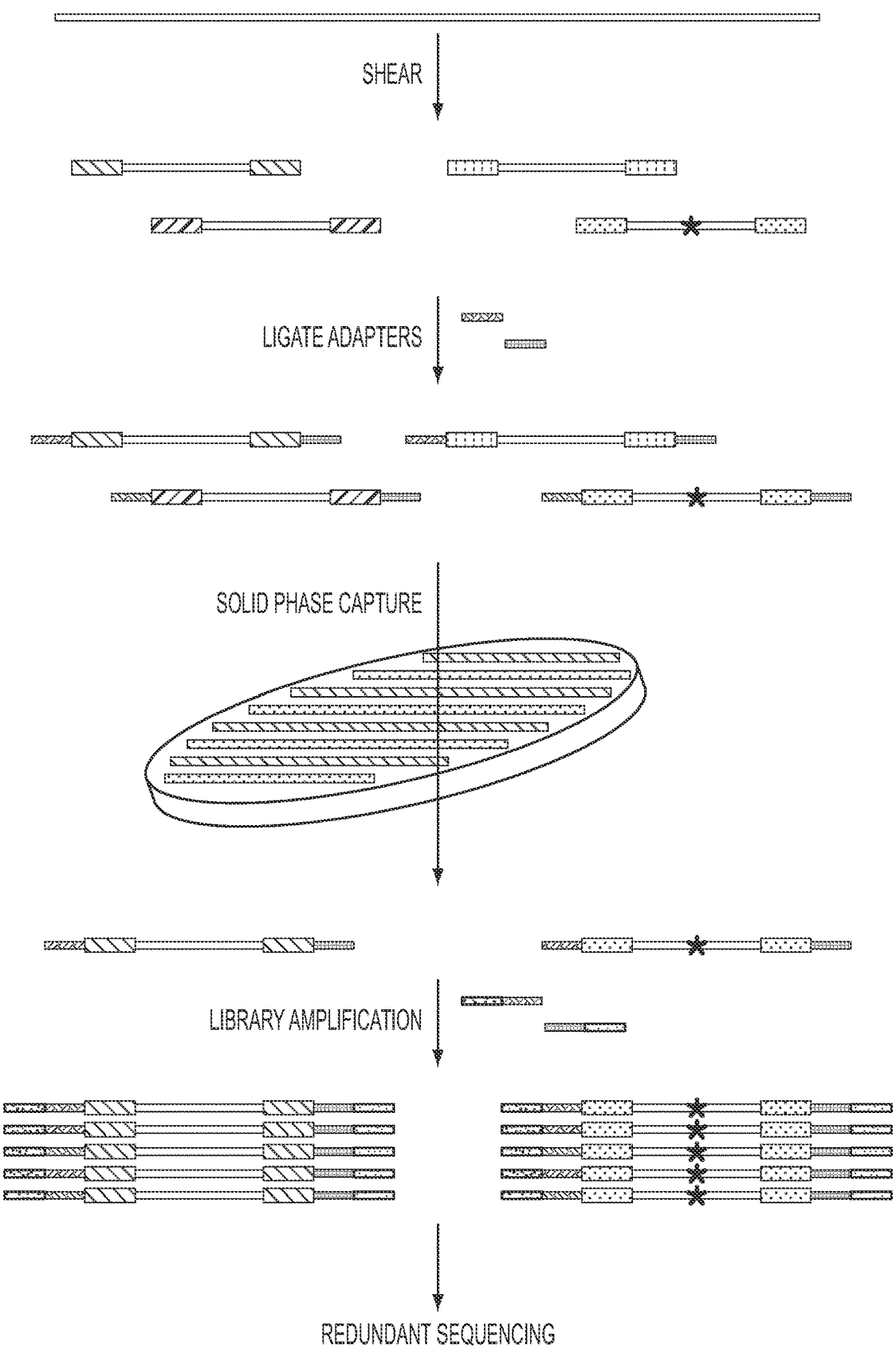
FIG. 2. Safe-SeqS with Endogenous UIDs Plus Capture. The sequences of the ends of each fragment produced by random shearing (variously shaded bars) serve as the unique identifiers (UIDs). These fragments are ligated to adapters (earth hatched and cross hatched bars) so they can subsequently be amplified by PCR. One uniquely identifiable fragment is produced from each strand of the double-stranded template; only one strand is shown. Fragments of interest are captured on a solid phase containing oligonucleotides complementary to the sequences of interest. Following PCR amplification to produce UID-families with primers containing 5' "grafting" sequences (adhesive filled and light stippled bars), sequencing is performed and super-mutants are defined as in FIG. 1.
Figure 5:
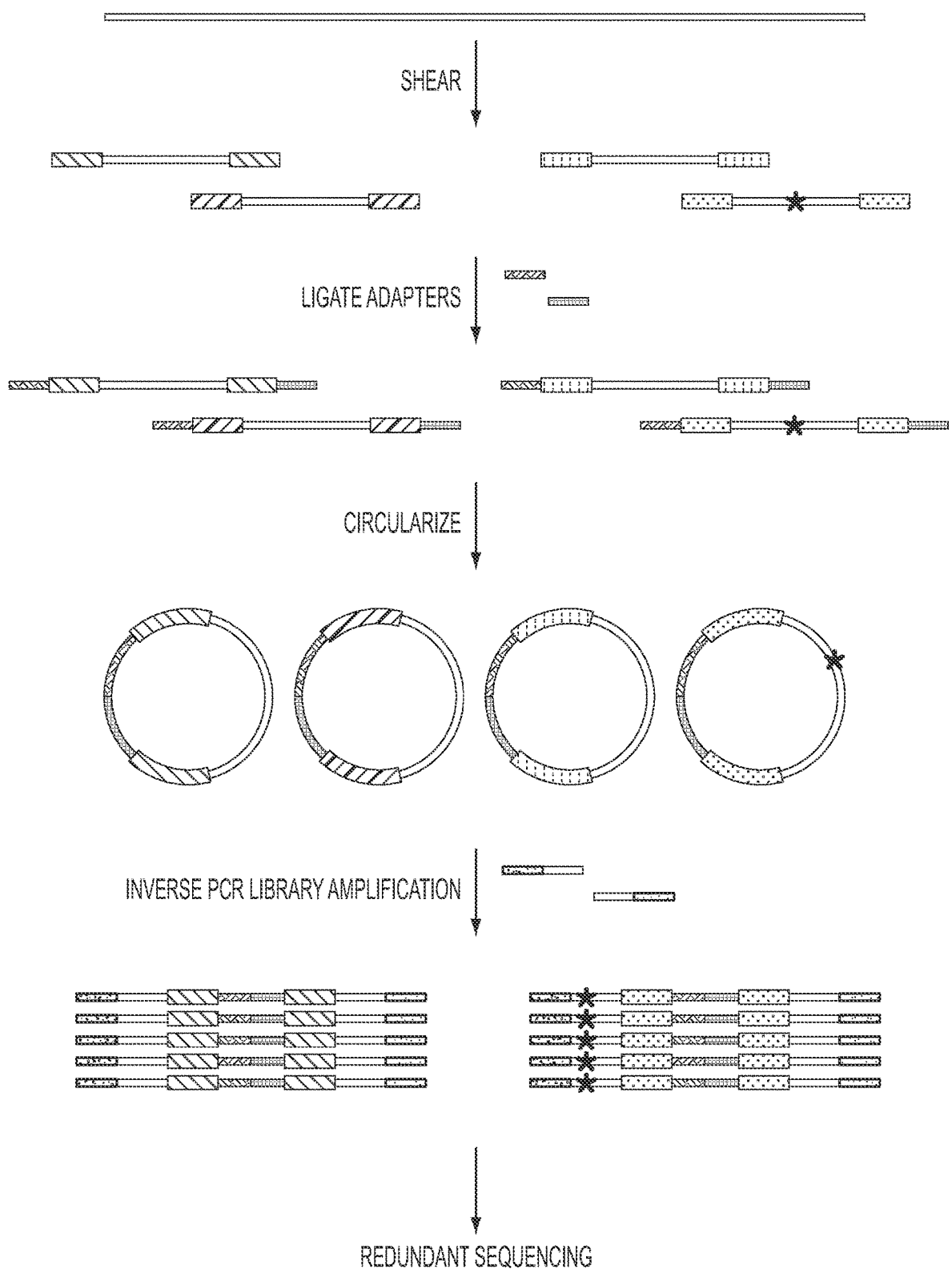
FIG. 5. Safe-SeqS with endogenous UIDs plus inverse PCR. The sequence of the ends of each fragment produced by random shearing serve as unique identifiers (UIDs; variously shaded bars). These fragments are ligated to adapters (earth hatched and cross hatched bars) as in a standard Illumina library preparation. One uniquely tagged fragment is produced from each strand of the double-stranded template; only one strand is shown. Following circularization with a ligase, inverse PCR is performed with gene-specific primers that also contain 5' "grafting" sequences (adhesive filled and lightly stippled bars). This PCR produces UID-families which are directly sequenced. Super-mutants are defined as in FIG. 1.

UIDs, sometimes called barcodes or indexes, can be assigned to nucleic acid fragments in many ways. These include the introduction of exogenous sequences through PCR (40, 41) or ligation (42, 43). Even more simply, randomly sheared genomic DNA inherently contains UIDs consisting of the sequences of the two ends of each sheared fragment (FIG. 2 and FIG. 5). Paired-end sequencing of these fragments yields UID-families that can be analyzed as described above. To employ such endogenous UIDs in Safe-SeqS, we used two separate approaches: one designed to evaluate many genes simultaneously and the other designed to evaluate a single gene fragment in depth (FIG. 2 and FIG. 5, respectively).

For the evaluation of multiple genes, we ligated standard Illumina sequencing adapters to the ends of sheared DNA fragments to produce a standard sequencing library, then captured genes of interest on a solid phase (44). In this experiment, a library made from the DNA of ~15,000 normal cells was used, and 2,594 bp from six genes were targeted for capture. After excluding known single nucleotide polymorphisms, 25,563 apparent mutations, corresponding to $2.4 \times 10^{-4}$ ±mutations/bp, were also identified (Table 1). Based on previous analyses of mutation rates in human cells, at least 90% of these apparent mutations were likely to represent mutations introduced during template and library preparation or base-calling errors. Note that the error rate determined here ($2.4 \times 10^{-4}$ mutations/bp) is considerably lower than usually reported in experiments using the Illumina instrument because we used very stringent criteria for base calling.

TABLE 1

Safe-SeqS with Endogenous UIDs

|  | Capture | Inverse PCR |
|---|---|---|
| Conventional Analysis |  |  |
| High quality bp | 106,958,863 | 1,041,346,645 |
| Mean high quality bp read depth | 38,620× | 2,085,600× |

TABLE 1-continued

Safe-SeqS with Endogenous UIDs

|  | Capture | Inverse PCR |
|---|---|---|
| Mutations identified | 25,563 | 234,352 |
| Mutations/bp | 2.4E−04 | 2.3E−04 |
| Safe-SeqS Analysis |  |  |
| High quality bp | 106,958,863 | 1,041,346,645 |
| Mean high quality bp read depth | 38,620× | 2,085,600× |
| UID-families | 69,505 | 1,057 |
| Average # of members/UID-family | 40 | 21,688 |
| Median # of members/UID-family | 19 | 4 |
| Super-mutants identified | 8 | 0 |
| Super-mutants/bp | 3.5E−06 | 0.0 |

With Safe-SeqS analysis of the same data, we determined that 69,505 original template molecules were assessed in this experiment (i.e., 69,505 UID-families, with an average of 40 members per family, were identified, Table 1). All of the polymorphic variants identified by conventional analysis were also identified by Safe-SeqS. However, only 8 super-mutants were observed among these families, corresponding to $3.5 \times 10^{-6}$ mutations/bp. Thus Safe-SeqS decreased the presumptive sequencing errors by at least 70-fold.

Safe-SeqS analysis can also determine which strand of a template is mutated, thus an additional criteria for calling mutations could require that the mutation appears in only one or in both strands of the originally double stranded template. Massively parallel sequencers are able to obtain sequence information from both ends of a template in two sequential reads. (This type of sequencing experiment is called a "paired end" run on the Illumina platform, but similar experiments can be done on other sequencing platforms where they may be called by another name.) The two strands of a double stranded template can be differentiated by the observed orientation of the sequences and the order in which they appear when sequence information is obtained from both ends. For example, a UID strand pair could consist of the following two groups of sequences when each end of a template is sequenced in sequential reads: 1) A sequence in the sense orientation that begins at position 100 of chromosome 2 in the first read followed by a sequence in the antisense orientation that begins at position 400 in the second read; and 2) A sequence in the antisense orientation that begins at position 400 of chromosome 2 in the first read followed by a sequence in the sense orientation that begins at position 100 of chromosome 2 in the second read. In the capture experiment described above, 42,222 of 69,505 UIDs (representing 21,111 original double stranded molecules) in the region of interest represented UID strand pairs. These 42,222 UIDs encompassed 1,417,838 bases in the region of interest. When allowing a mutation to only occur within UID strand pairs (whether in one or both strands), two super-mutants were observed, yielding a mutation rate of $1.4 \times 10^{-6}$ super-mutants/bp. When requiring that a mutation occur in only one strand of a UID strand pair, only one super-mutant was observed, yielding a mutation rate of $7.1 \times 10^{-7}$ super-mutants/bp. When requiring that a mutation occur in both strands of a UID strand pair, only one super-mutant was observed, yielding a mutation rate of $7.1 \times 10^{-7}$ super-mutants/bp. Thus, requiring that mutations occur in only one or in both strands of templates can further increase the specificity of Safe-SeqS.

A strategy employing endogenous UIDs was also used to reduce false positive mutations upon deep sequencing of a single region of interest. In this case, a library prepared as described above from ~1,750 normal cells was used as template for inverse PCR employing primers complementary to a gene of interest, so the PCR products could be directly used for sequencing (FIG. 5). With conventional analysis, an average of $2.3 \times 10^{-4}$ mutations/bp were observed, similar to that observed in the capture experiment (Table 1). Given that only 1,057 independent molecules from normal cells were assessed in this experiment, as determined through Safe-SeqS analysis, all mutations observed with conventional analysis likely represented false positives (Table 1). With Safe-SeqS analysis of the same data, no super-mutants were identified at any position.

Example 2—Exogenous UIDs

Though the results described above show that Safe-SeqS can increase the reliability of massively parallel sequencing, the number of different molecules that can be examined using endogenous UIDs is limited. For fragments sheared to an average size of 150 bp (range 125-175), 36 base paired-end sequencing can evaluate a maximum of ~7,200 different molecules containing a specific mutation (2 reads×2 orientations×36 bases/read×50 base variation on either end of the fragment). In practice, the actual number of UIDs is smaller because the shearing process is not entirely random.

Figure 3:
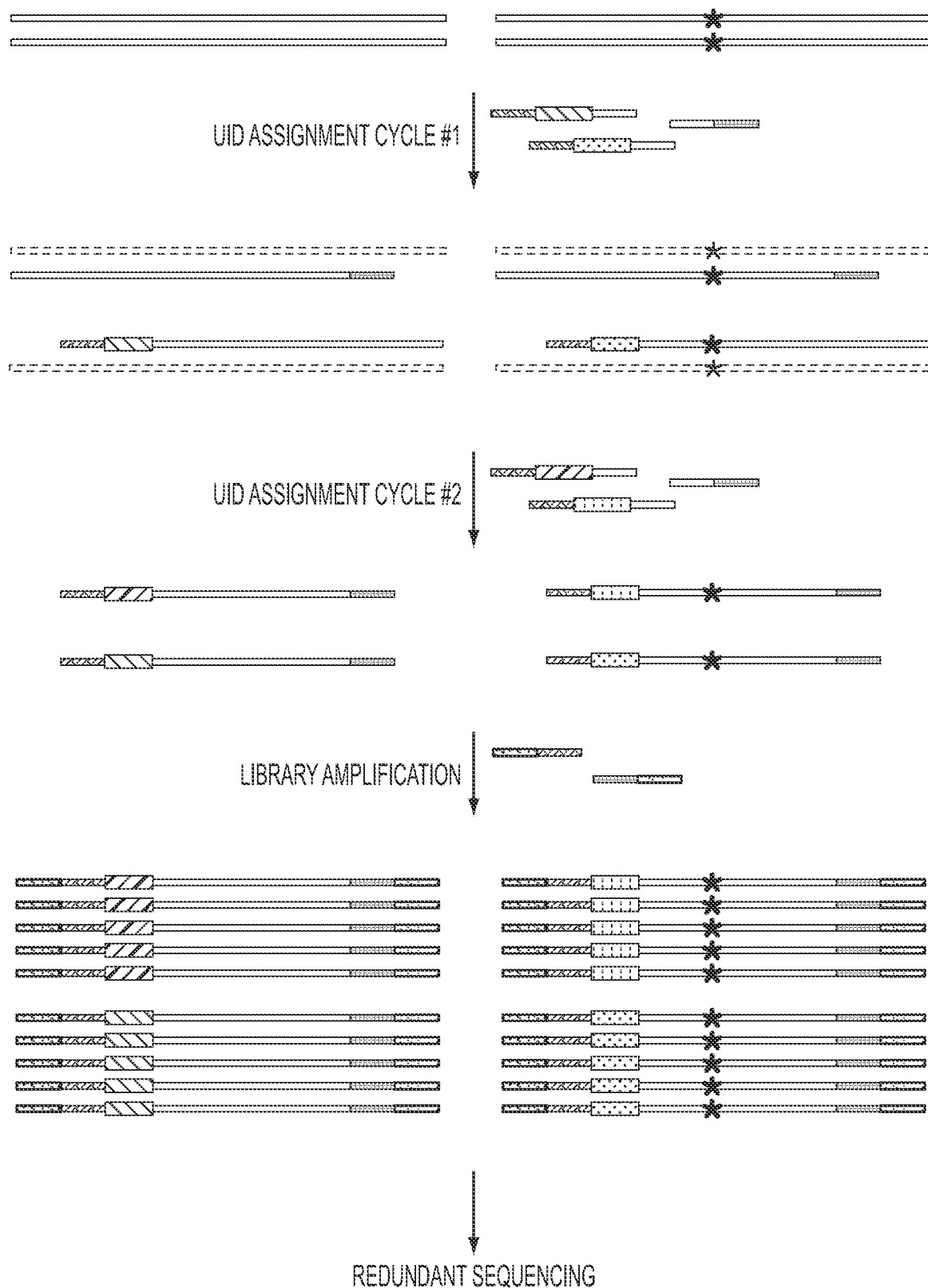
FIG. 3. Safe-SeqS with Exogenous UIDs. DNA (sheared or unsheared) is amplified with a set of gene-specific primers. One of the primers has a random DNA sequence (e.g., a set of 14 N's) that forms the unique identifier (UID; variously shaded bars), located 5' to its gene-specific sequence, and both have sequences that permit universal amplification in the next step (earth hatched and cross hatched bars). Two UID assignment cycles produce two fragments—each with a different UID—from each double—stranded template molecule, as shown. Subsequent PCR with universal primers, which also contain "grafting" sequences (adhesive filled and light stippled bars), produces UID-families which are directly sequenced. Super-mutants are defined as in the legend to FIG. 1.

To make more efficient use of the original templates, we developed a Safe-SeqS strategy that employed a minimum number of enzymatic steps. This strategy also permitted the use of degraded or damaged DNA, such as found in clinical specimens or after bisulfite-treatment for the examination of cytosine methylation (45). As depicted in FIG. 3, this strategy employs two sets of PCR primers. The first set is synthesized with standard phosphoramidite precursors and contained sequences complementary to the gene of interest on the 3' end and different tails at the 5' ends of both the forward and reverse primers. The different tails allowed universal amplification in the next step. Finally, there was a stretch of 12 to 14 random nucleotides between the tail and the sequence-specific nucleotides in the forward primer (40). The random nucleotides form the UIDs. An equivalent way to assign UIDs to fragments, not used in this study, would employ 10,000 forward primers and 10,000 reverse primers synthesized on a microarray. Each of these 20,000 primers would have gene-specific primers at their 3'-ends and one of 10,000 specific, predetermined, non-overlapping UID sequences at their 5'-ends, allowing for $10^8$ (i.e., $[10^4]^2$) possible UID combinations. In either case, two cycles of PCR are performed with the primers and a high-fidelity polymerase, producing a uniquely tagged, double-stranded DNA fragment from each of the two strands of each original template molecule (FIG. 3). The residual, unused UID assignment primers are removed by digestion with a single-strand specific exonuclease, without further purification, and two new primers are added. Alternatively or in addition to such digestion, one can use a silica column that selectively retains larger-sized fragments or one can use solid phase reversible immobilization (SPRI) beads under conditions that selectively retain larger fragments to eliminate smaller, non-specific, amplification artifacts. This purification may potentially help in reducing primer-dimer accumulation in later steps. The new primers, complementary to the tails introduced in the UID assignment cycles, contain grafting sequences at their 5' ends, permitting solid-phase amplification on the Illumina instrument, and phosphorothioate residues at their 3' ends to make them resistant to any remaining exonuclease. Following 25 additional cycles of PCR, the products are loaded on the Illumina instrument. As Example 3—Analysis of DNA Polymerase Fidelity Measurement of the error rates of DNA polymerases is essential for their characterization and dictates the situations in which these enzymes can be used. We chose to measure the error rate of Phusion polymerase, as this polymerase has one of the lowest reported error frequencies of any commercially available enzyme and therefore poses a particular challenge for an in vitro-based approach. We first amplified a single human DNA template molecule, comprising a segment of an arbitrarily chosen human gene, through 19 rounds of PCR. The PCR products from these amplifications, in their entirety, were used as templates for Safe-SeqS as described in FIG. 3. In seven independent experiments of this type, the number of UID-families identified by sequencing was 624,678±421,274, which is consistent with an amplification efficiency of 92±9.6% per round of PCR.

The error rate of Phusion polymerase, estimated through cloning of PCR products encoding β-galactosidase in plasmid vectors and transformation into bacteria, is reported by the manufacturer to be $4.4 \times 10^{-7}$ errors/bp/PCR cycle. Even with very high stringency base-calling, conventional analysis of the Illumina sequencing data revealed an apparent error rate of $9.1 \times 10^{-6}$ errors/bp/PCR cycle, more than an order of magnitude higher than the reported Phusion polymerase error rate (Table 2A). In contrast, Safe-SeqS of the same data revealed an error rate of $4.5 \times 10^{-7}$ errors/bp/PCR cycle, nearly identical to that measured for Phusion polymerase in biological assays (Table 2A). The vast majority (>99%) of these errors were single base substitutions (Table 3A), consistent with previous data on the mutation spectra created by other prokaryotic DNA polymerases (15, 46, 47).

TABLE 2A-2C

Safe-SeqS with Exogenous UIDs

|  | Mean | Standard Deviation |
| --- | --- | --- |
| 2A. Polymerase Fidelity Conventional analysis of 7 replicates | | |
| High quality bp | 996,855,791 | 64,030,757 |
| Total mutations identified | 198,638 | 22,515 |
| Mutations/bp | 2.0E−04 | 1.7E−05 |
| Calculated Phusion Error Rate (errors/bp/cycle) | 9.1E−06 | 7.7E−07 |
| Safe-SeqS analysis of 7 replicates | | |
| High quality bp | 996,855,791 | 64,030,757 |
| UID-families | 624,678 | 421,274 |
| Members/UID-family | 107 | 122 |
| Total super-mutants identified | 197 | 143 |
| Super-mutants/bp | 9.9E−06 | 2.3E−06 |
| Calculated Phusion Error Rate (errors/bp/cycle) | 4.5E−07 | 1.0E−07 |
| 2B. CTNNB1 mutations in DNA from normal human cells Conventional analysis of 3 individuals | | |
| High quality bp | 559,334,774 | 66,600,749 |
| Total mutations identified | 118,488 | 11,357 |
| Mutations/bp | 2.1E−04 | 1.6E−05 |
| Safe-SeqS analysis of 3 individuals | | |
| High quality bp | 559,334,774 | 66,600,749 |
| UID-families | 374,553 | 263,105 |
| Members/UID-family | 68 | 38 |
| Total super-mutants identified | 99 | 78 |
| Super-mutants/bp | 9.0E−06 | 3.1E−06 |
| 2C. Mitochondrial mutations in DNA from normal human cells Conventional analysis of 7 individuals | | |
| High quality bp | 147,673,456 | 54,308,546 |
| Total mutations identified | 30,599 | 12,970 |
| Mutations/bp | 2.1E−04 | 9.4E−05 |
| Safe-SeqS analysis of 7 individuals | | |
| High quality bp | 147,673,456 | 54,308,546 |
| UID-families | 515,600 | 89,985 |
| Members/UID-family | 15 | 6 |
| Total super-mutants identified | 135 | 61 |
| Super-mutants/bp | 1.4E−05 | 6.8E−06 |

TABLE 3A-C

Fraction of Single Base Substitutions, Insertions, and Deletions with Exogenous UIDs

|  | Mean | Standard Deviation |
| --- | --- | --- |
| 3A. Polymerase Fidelity Conventional analysis of 7 replicates | | |
| Total mutations identified | 198,638 | 22,515 |
| Fraction of mutations represented by single base substitutions | 99% | 0% |
| Fraction of mutations represented by deletions | 1% | 0% |
| Fraction of mutations represented by insertions | 0% | 0% |
| Safe-SeqS analysis of 7 replicates | | |
| Total super-mutants identified | 197 | 143 |
| Fraction of super-mutants represented by single base substitutions | 99% | 2% |
| Fraction of super-mutants represented by deletions | 1% | 2% |
| Fraction of super-mutants represented by insertions | 0% | 0% |
| 3B. CTNNB1 mutations in DNA from normal human cells Conventional analysis of 3 individuals | | |
| Total mutations identified | 118,488 | 11,357 |
| Fraction of mutations represented by single base substitutions | 97% | 0% |
| Fraction of mutations represented by deletions | 3% | 0% |
| Fraction of mutations represented by insertions | 0% | 0% |
| Safe-SeqS analysis of 3 individuals | | |
| Total super-mutants identified | 99 | 78 |
| Fraction of super-mutants represented by single base substitutions | 100% | 1% |
| Fraction of super-mutants represented by deletions | 0% | 1% |
| Fraction of super-mutants represented by insertions | 0% | 0% |
| 3C. Mitochondrial mutations in DNA from normal human cells Conventional analysis of 7 individuals | | |
| Total mutations identified | 30,599 | 12,970 |
| Fraction of mutations represented by single base substitutions | 98% | 1% |
| Fraction of mutations represented by deletions | 2% | 1% |
| Fraction of mutations represented by insertions | 0% | 0% |
| Safe-SeqS analysis of 7 individuals | | |
| Total super-mutants identified | 135 | 61 |
| Fraction of super-mutants represented by single base substitutions | 99% | 1% |
| Fraction of super-mutants represented by deletions | 1% | 1% |
| Fraction of super-mutants represented by insertions | 0% | 0% |

Safe-SeqS also allowed a determination of the total number of distinct mutational events and an estimation of PCR cycle in which the mutation occurred. There were 19 cycles of PCR performed in wells containing a single template molecule in these experiments. If a polymerase error occurred in cycle 19, there would be only one super-mutant produced (from the strand containing the mutation). If the error occurred in cycle 18 there should be two super-mutants (derived from the mutant strands produced in cycle 19), etc. Accordingly, the cycle in which the error occurred is related to the number of super-mutants containing that error. The data from seven independent experiments demonstrate a relatively consistent number of observed total polymerase errors ($2.2 \pm 1.1 \times 10^{-6}$ distinct mutations/bp), in good agreement with the expected number of observations from simulations ($1.5 \pm 0.21 \times 10^{-6}$ distinct mutations/bp). The data also show a highly variable timing of occurrence of polymerase errors among experiments (Table 4), as predicted from classic fluctuation analysis (1). This kind of information is difficult to derive using conventional analysis of the same next-generation sequencing data, in part because of the prohibitively high apparent mutation rate noted above.

TABLE 4A-4G

Observed and Expected Number of Errors Generated by Phusion Polymerase

|  | Observed | Expected (mean ± SD)* |
|---|---|---|
| 4A. Experiment 1 | | |
| Mutations represented by 1 super-mutant | 10 | 19 ± 3.7 |
| Mutations represented by 2 super-mutants | 8 | 5.8 ± 2.3 |
| Mutations represented by 3 super-mutants | 4 | 1.3 ± 1.1 |
| Mutations represented by 4 super-mutants | 4 | 1.8 ± 1.3 |
| Mutations represented by 5 super-mutants | 2 | 0.61 ± 0.75 |
| Mutations represented by 6 super-mutants | 2 | 0.22 ± 0.44 |
| Mutations represented by 7 super-mutants | 0 | 0.01 ± 0.10 |
| Mutations represented by 8 super-mutants | 0 | 0.87 ± 0.86 |
| Mutations represented by 9 super-mutants | 2 | 0.28 ± 0.51 |
| Mutations represented by 10 super-mutants | 0 | 0.14 ± 0.38 |
| Mutations represented by >10 super-mutants | 3 | 1.5 ± 2.7 |
| Distinct mutations | 35 | 32 ± 4.2 |
| 4B. Experiment 2 | | |
| Mutations represented by 1 super-mutant | 19 | 23 ± 4.1 |
| Mutations represented by 2 super-mutants | 5 | 9.5 ± 2.8 |
| Mutations represented by 3 super-mutants | 4 | 2.7 ± 1.6 |
| Mutations represented by 4 super-mutants | 7 | 2.7 ± 1.7 |
| Mutations represented by 5 super-mutants | 2 | 0.88 ± 0.94 |
| Mutations represented by 6 super-mutants | 1 | 0.40 ± 0.60 |
| Mutations represented by 7 super-mutants | 3 | 0.16 ± 0.42 |
| Mutations represented by 8 super-mutants | 1 | 0.99 ± 1.0 |
| Mutations represented by 9 super-mutants | 1 | 0.39 ± 0.68 |
| Mutations represented by 10 super-mutants | 0 | 0.17 ± 0.43 |
| Mutations represented by >10 super-mutants | 9 | 1.8 ± 3.4 |
| Distinct mutations | 52 | 43 ± 5.1 |
| 4C. Experiment 3 | | |
| Mutations represented by 1 super-mutant | 7 | 17 ± 3.4 |
| Mutations represented by 2 super-mutants | 9 | 5.4 ± 2.0 |
| Mutations represented by 3 super-mutants | 4 | 1.2 ± 1.1 |
| Mutations represented by 4 super-mutants | 4 | 1.7 ± 1.4 |
| Mutations represented by 5 super-mutants | 2 | 0.50 ± 0.70 |
| Mutations represented by 6 super-mutants | 0 | 0.17 ± 0.45 |
| Mutations represented by 7 super-mutants | 1 | 0.03 ± 0.17 |
| Mutations represented by 8 super-mutants | 0 | 0.59 ± 0.74 |
| Mutations represented by 9 super-mutants | 0 | 0.24 ± 0.50 |
| Mutations represented by 10 super-mutants | 1 | 0.07 ± 0.29 |
| Mutations represented by >10 super-mutants | 5 | 1.5 ± 2.6 |
| Distinct mutations | 33 | 28 ± 3.7 |
| 4D. Experiment 4 | | |
| Mutations represented by 1 super-mutant | 7 | 15 ± 3.7 |
| Mutations represented by 2 super-mutants | 8 | 4.1 ± 1.7 |
| Mutations represented by 3 super-mutants | 2 | 0.70 ± 0.74 |
| Mutations represented by 4 super-mutants | 1 | 1.5 ± 1.3 |
| Mutations represented by 5 super-mutants | 3 | 0.21 ± 0.52 |
| Mutations represented by 6 super-mutants | 2 | 0.08 ± 0.27 |
| Mutations represented by 7 super-mutants | 1 | 0.0 ± 0.0 |
| Mutations represented by 8 super-mutants | 2 | 0.65 ± 0.77 |
| Mutations represented by 9 super-mutants | 2 | 0.17 ± 0.43 |
| Mutations represented by 10 super-mutants | 0 | 0.05 ± 0.22 |
| Mutations represented by >10 super-mutants | 1 | 0.92 ± 2.1 |
| Distinct mutations | 29 | 23 ± 3.2 |
| 4E. Experiment 5 | | |
| Mutations represented by 1 super-mutant | 9 | 23 ± 4.1 |
| Mutations represented by 2 super-mutants | 6 | 9.5 ± 2.8 |
| Mutations represented by 3 super-mutants | 5 | 2.7 ± 1.6 |
| Mutations represented by 4 super-mutants | 3 | 2.7 ± 1.7 |
| Mutations represented by 5 super-mutants | 6 | 0.88 ± 0.94 |
| Mutations represented by 6 super-mutants | 2 | 0.40 ± 0.60 |
| Mutations represented by 7 super-mutants | 1 | 0.16 ± 0.42 |
| Mutations represented by 8 super-mutants | 2 | 0.99 ± 1.0 |
| Mutations represented by 9 super-mutants | 2 | 0.39 ± 0.68 |
| Mutations represented by 10 super-mutants | 3 | 0.17 ± 0.43 |
| Mutations represented by >10 super-mutants | 7 | 1.8 ± 3.4 |
| Distinct mutations | 46 | 43 ± 5.1 |
| 4F. Experiment 6 | | |
| Mutations represented by 1 super-mutant | 4 | 6.7 ± 2.8 |
| Mutations represented by 2 super-mutants | 7 | 1.5 ± 1.2 |
| Mutations represented by 3 super-mutants | 1 | 0.10 ± 0.33 |
| Mutations represented by 4 super-mutants | 2 | 0.60 ± 0.82 |
| Mutations represented by 5 super-mutants | 0 | 0.07 ± 0.26 |
| Mutations represented by 6 super-mutants | 0 | 0.01 ± 0.10 |
| Mutations represented by 7 super-mutants | 1 | 0.0 ± 0.0 |
| Mutations represented by 8 super-mutants | 1 | 0.39 ± 0.60 |
| Mutations represented by 9 super-mutants | 0 | 0.01 ± 0.10 |
| Mutations represented by 10 super-mutants | 0 | 0.0 ± 0.0 |
| Mutations represented by >10 super-mutants | 2 | 0.50 ± 1.1 |
| Distinct mutations | 18 | 9.9 ± 1.4 |
| 4G. Experiment 7 | | |
| Mutations represented by 1 super-mutant | 8 | 2.9 ± 1.6 |
| Mutations represented by 2 super-mutants | 2 | 0.61 ± 0.79 |
| Mutations represented by 3 super-mutants | 0 | 0.04 ± 0.24 |
| Mutations represented by 4 super-mutants | 0 | 0.41 ± 0.59 |
| Mutations represented by 5 super-mutants | 1 | 0.01 ± 0.10 |
| Mutations represented by 6 super-mutants | 0 | 0.0 ± 0.0 |
| Mutations represented by 7 super-mutants | 0 | 0.0 ± 0.0 |
| Mutations represented by 8 super-mutants | 0 | 0.14 ± 0.35 |
| Mutations represented by 9 super-mutants | 0 | 0.01 ± 0.10 |
| Mutations represented by 10 super-mutants | 0 | 0.0 ± 0.0 |
| Mutations represented by >10 super-mutants | 0 | 0.32 ± 0.93 |
| Distinct mutations | 11 | 4.5 ± 0.62 |

*See SI Text for details of the simulations

Example 4—Analysis of Oligonucleotide Composition

A small number of mistakes during the synthesis of oligonucleotides from phoshoramidite precursors are tolerable for most applications, such as routine PCR or cloning. However, for synthetic biology, wherein many oligonucleotides must be joined together, such mistakes present a major obstacle to success. Clever strategies for making the gene construction process more efficient have been devised (48, 49), but all such strategies would benefit from more accurate synthesis of the oligonucleotides themselves. Determining the number of errors in synthesized oligonucleotides is difficult because the fraction of oligonucleotides containing errors can be lower than the sensitivity of conventional next-generation sequencing analyses.

Figure 4A:
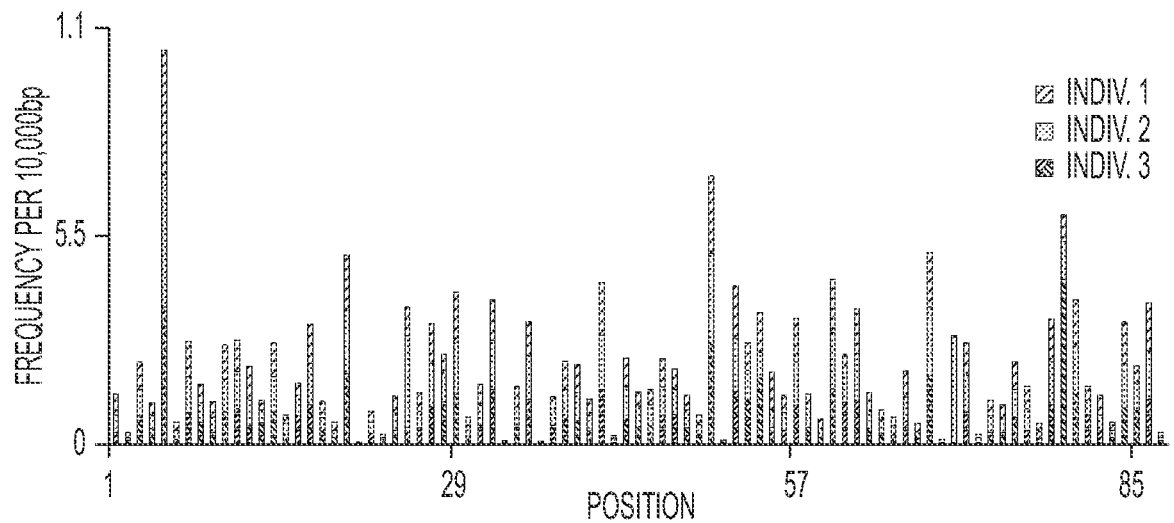
FIGS. 4A-4B. Single Base Substitutions Identified by Conventional and Safe-SeqS Analysis. The exogenous UID strategy depicted in FIG. 3 was used to produce PCR fragments from the CTNNB1 gene of three normal, unrelated individuals. Each position represents one of 87 possible single base substitutions (3 possible substitutions/base×29 bases analyzed). These fragments were sequenced on an Illumina GA IIx instrument and analyzed in the conventional manner (FIG. 4A) or with Safe-SeqS (FIG. 4B). Safe-SeqS results are displayed on the same scale as conventional analysis for direct comparison; the inset is a magnified view. Note that most of the variants identified by conventional analysis are likely to represent sequencing errors, as indicated by their high frequency relative to Safe-SeqS and their consistency among unrelated samples.
Figure 4B:
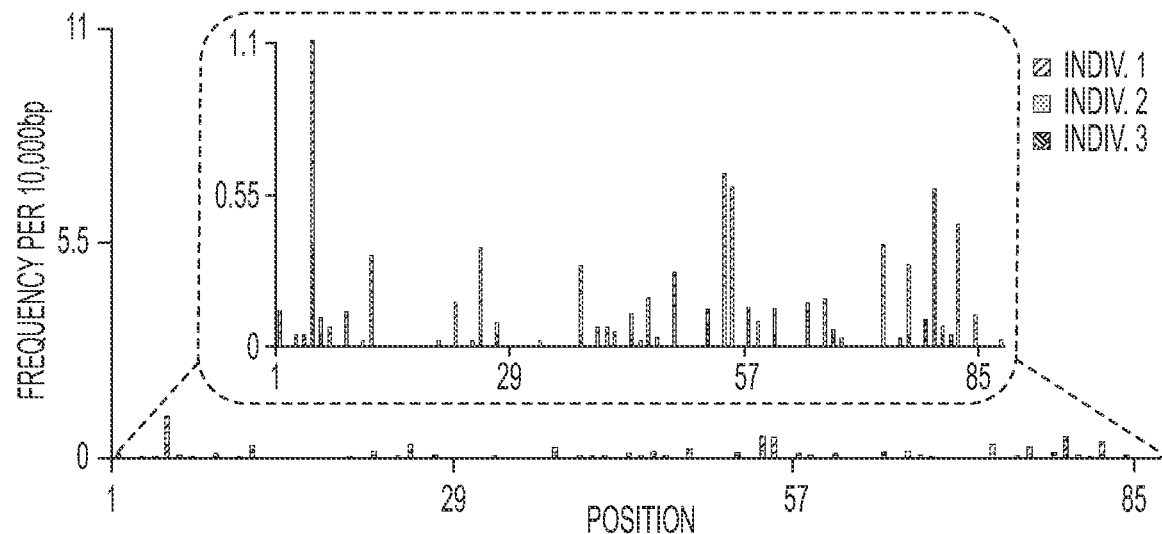
Figures 6A, 6B:
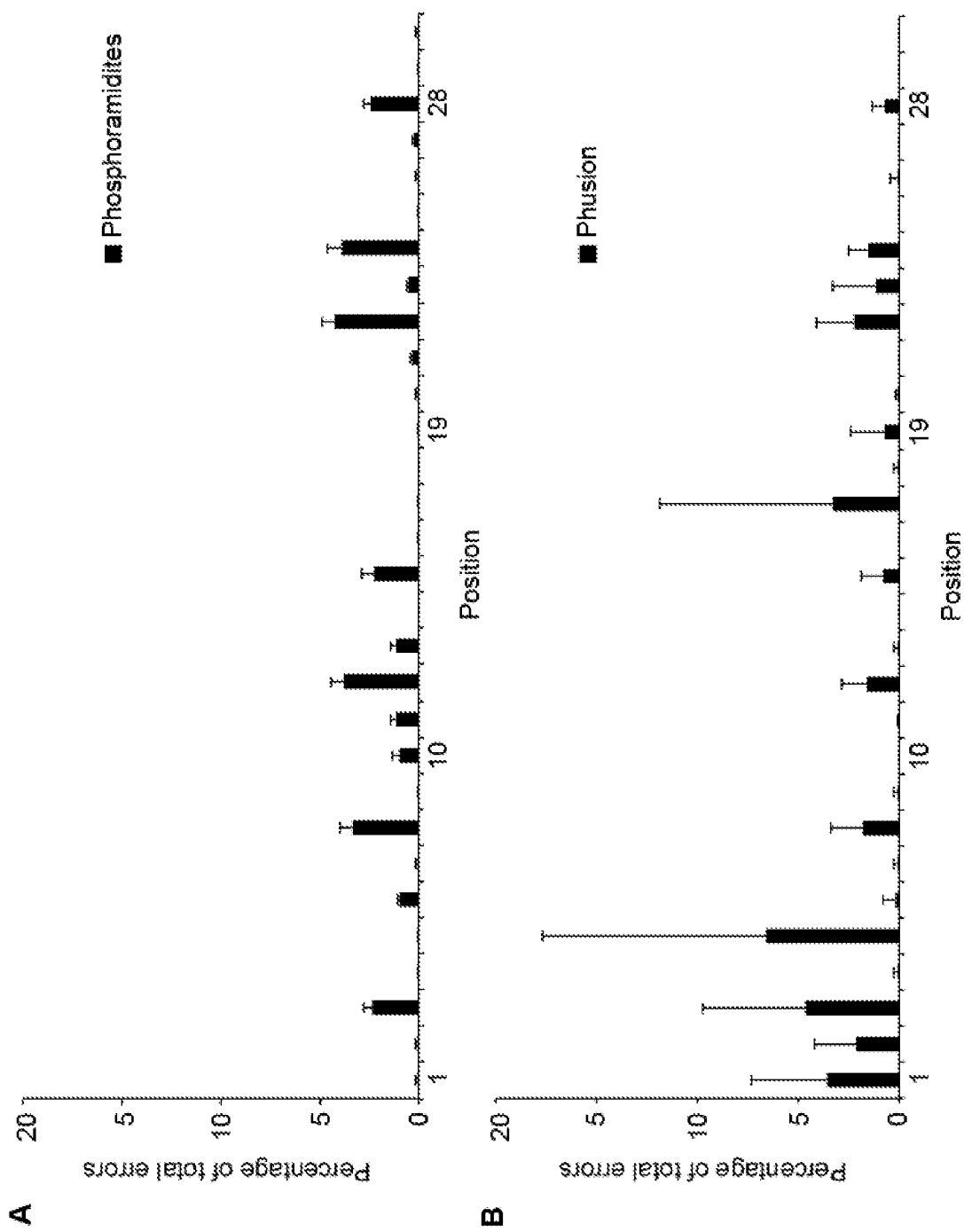
FIG. 6A-6B. Single base substitutions position vs. error frequency in oligonucleotides synthesized with phosphoramidites and Phusion. A representative portion of the same 31-base DNA fragment synthesized with phosphoramidites (FIG. 6A) or Phusion polymerase (FIG. 6B) was analyzed by Safe-SeqS. The means and standard deviations for seven independent experiments of each type are plotted. There was an average of 1,721±383 and 196±143 SBS super-mutants identified in the phosphoramidite-synthesized and Phusion-generated fragments, respectively. The y-axis indicates the fraction of the total errors at the indicated position. Note that the errors in the phosphoramidite-synthesized DNA fragment were consistent among the seven replicates, as would be expected if the errors were systematically introduced during the synthesis itself. In contrast, the errors in the Phusion-generated fragments appeared to be heterogeneous among samples, as expected from a stochastic process (Luria and Delbruck, *Genetics* 28: 491-511, 1943).
Figure 7:
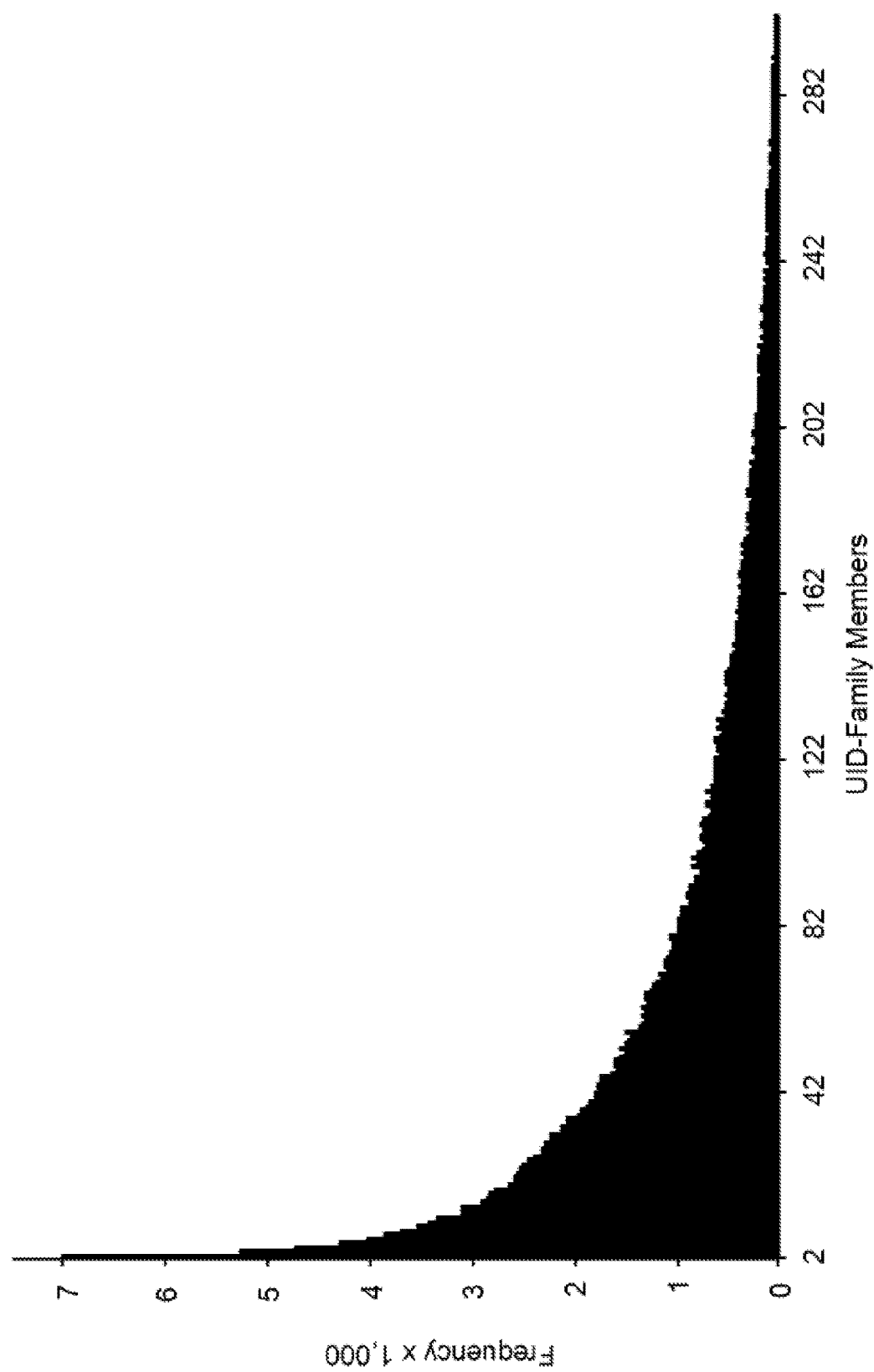
FIG. 7. UID-family member distribution. The exogenous UID strategy depicted in FIG. 3 was used to produce PCR fragments from a region of CTNNB1 from three normal, unrelated individuals (Table 2B); a representative example of the UID-families with ≤300 members (99% of total UID-families) generated from one individual is shown. The y-axis indicates the number of different UID-families that contained the number of family members shown on the x-axis.

To determine whether Safe-SeqS could be used for this determination, we used standard phosphoramidite chemistry to synthesize an oligonucleotide containing 31 bases that were designed to be identical to that analyzed in the polymerase fidelity experiment described above. In the synthetic oligonucleotide, the 31 bases were surrounded by sequences complementary to primers that could be used for the UID assignment steps of Safe-SeqS (FIG. 3). By performing Safe-SeqS on ~300,000 oligonucleotides, we found that there were $8.9 \pm 0.28 \times 10^{-4}$ super-mutants/bp and that these errors occurred throughout the oligonucleotides (FIG. 6A). The oligonucleotides contained a large number of insertion and deletion errors, representing $8.2 \pm 0.63\%$ and $25 \pm 1.5\%$ of the total super-mutants, respectively. Importantly, both the position and nature of the errors were highly reproducible among seven independent replicates of this experiment performed on the same batch of oligonucleotides (FIG. 6A). This nature and distribution of errors had little in common with that of the errors produced by Phusion polymerase (FIG. 6B and Table 5), which were distributed in the expected stochastic pattern among replicate experiments. The number of errors in the oligonucleotides synthesized with phosphoramidites was ~60 times higher than in the equivalent products synthesized by Phusion polymerase. These data, in toto, indicate that the vast majority of errors in the former were generated during their synthesis rather than during the Safe-SeqS procedure.

of the CTNNB1 gene from ~100,000 normal human cells from three unrelated individuals. Through comparison with the number of UID-families obtained in the Safe-SeqS experiments (Table 2B), we calculated that the majority ($78 \pm 9.8\%$) of the input fragments were converted into UID-families. There was an average of 68 members/UID-family, easily fulfilling the required redundancy for Safe-SeqS (FIG. 7). Conventional analysis of the Illumina sequencing data revealed an average of $118,488 \pm 11,357$ mutations among the ~560 Mb of sequence analyzed per sample, corresponding to an apparent mutation prevalence of $2.1 \pm 0.16 \times 10^{-4}$ mutations/bp (Table 2B). Only an average of $99 \pm 78$ super-mutants were observed in the Safe-SeqS analysis. The vast majority (>99%) of super-mutants were single base substitutions and the calculated mutation rate was $9.0 \pm 3.1 \times 10^{-6}$ mutations/bp (Table 3B). Safe-SeqS thereby reduced the apparent frequency of mutations in genomic DNA by at least 24-fold (FIG. 4).

One possible strategy to increase the specificity of Safe-SeqS is to perform the library amplification (and possibly the UID assignment cycles) in multiple wells. This can be accomplished in as few as 2 or as many as 384 wells using standard PCR plates, or scaled up to many more wells when using a microfluidic device (thousands to millions). When performed this way, indexing sequences can be introduced into the templates that are unique to the wells in which the template is amplified. Rare mutations, thus, should give rise to two super-mutants (i.e., one from each strand), both with the same well index sequence. When performing Safe-SeqS with exogenous UIDs on the CTNNB1 templates described

TABLE 5

Phosphoramidite- vs Phusion-Synthesized DNA: Transitions vs Transversions Comparison

|  | Exp. 1 | Exp. 2 | Exp. 3 | Exp. 4 | Exp. 5 | Exp. 6 | Exp. 7 | Average | Standard Deviation |
|---|---|---|---|---|---|---|---|---|---|
| Phosphoramidites |  |  |  |  |  |  |  |  |  |
| Transition super-mutants: | 496 | 509 | 471 | 396 | 323 | 273 | 470 | 420 | 92 |
| Transversion super-mutants: | 1494 | 1499 | 1521 | 1154 | 944 | 907 | 1626 | 1306 | 298 |
| p-value* | 3.4E-05 |  |  |  |  |  |  |  |  |
| Phusion |  |  |  |  |  |  |  |  |  |
| Transition super-mutants: | 63 | 275 | 127 | 5 | 87 | 182 | 103 | 120 | 87 |
| Transversion super-mutants: | 14 | 124 | 77 | 12 | 57 | 191 | 63 | 77 | 63 |
| p-value* | 0.08 |  |  |  |  |  |  |  |  |

*p-values were calculated using a two-tailed paired t-test

Does Safe-SeqS preserve the ratio of mutant:normal sequences in the original templates? To address this question, we synthesized two 31-base oligonucleotides of identical sequence with the exception of nt 15 (50:50 C/G instead of T) and mixed them at nominal mutant/normal fractions of 3.3% and 0.33%. Through Safe-SeqS analysis of the oligonucleotide mixtures, we found that the ratios were 2.8% and 0.27%, respectively. We conclude that the UID assignment and amplification procedures used in Safe-SeqS do not greatly alter the proportion of variant sequences and thereby provide a reliable estimate of that proportion when unknown. This conclusion is also supported by the reproducibility of variant fractions when analyzed in independent Safe-SeqS experiments (FIG. 6A).

Example 5—Analysis of DNA Sequences from Normal Human Cells

The exogenous UID strategy (FIG. 3) was then used to determine the prevalence of rare mutations in a small region above and diluted into 10 wells (each well yielding templates amplified with a different index sequence), the mutation rate was further reduced from $9.0 \pm 3.1 \times 10^{-6}$ to $3.7 \pm 1.2 \times 10^{-6}$ super-mutants/bp. Thus, analyzing templates in multiple compartments—in a manner that yields differentially encoded templates based on the compartment in which templates were amplified—may be an additional strategy to increase the specificity of Safe-SeqS.

Example 6—Analysis of DNA Sequences from Mitochondrial DNA

We applied the identical strategy to a short segment of mitochondrial DNA in ~1,000 cells from each of seven unrelated individuals. Conventional analysis of the Illumina sequencing libraries produced with the Safe-SeqS procedure (FIG. 3) revealed an average of $30,599 \pm 12,970$ mutations among the ~150 Mb of sequence analyzed per sample, corresponding to an apparent mutation prevalence of 2.1±0.94×10$^{-4}$ mutations/bp (Table 2C). Only 135±61 super-mutants were observed in the Safe-SeqS analysis. As with the CTNNB1 gene, the vast majority of mutations were single base substitutions, though occasional single base deletions were also observed (Table 3C). The calculated mutation rate in the analyzed segment of mtDNA was 1.4±0.68×10$^{-5}$ mutations/bp (Table 2C). Thus, Safe-SeqS thereby reduced the apparent frequency of mutations in genomic DNA by at least 15-fold.

Example 7—Materials and Methods

Endogenous UIDs. Genomic DNA from human pancreas or cultured lymphoblastoid cells was prepared using Qiagen kits. The pancreas DNA was used for the capture experiment and the lymphoblastoid cells were used for the inverse PCR experiment. DNA was quantified by optical absorbance and with qPCR. DNA was fragmented to an average size of ~200 bp by acoustic shearing (Covaris), then end-repaired, A-tailed, and ligated to Y-shaped adapters according to standard Illumina protocols. The ends of each template molecule provide endogenous UIDs corresponding to their chromosomal positions. After PCR-mediated amplification of the libraries with primer sequences within the adapters, DNA was captured (1) with a filter containing 2,594 nt corresponding to six cancer genes. After capture, 18 cycles of PCR were performed to ensure sufficient amounts of template for sequencing on an Illumina GA IIx instrument.

For the inverse PCR experiments (FIG. 5), we ligated custom adapters (IDT, Table 6) instead of standard Y-shaped Illumina adapters to sheared cellular DNA. These adapters retained the region complementary to the universal sequencing primer but lacked the grafting sequences required for hybridization to the Illumina GA IIx flow cell. The ligated DNA was diluted into 96 wells and the DNA in each column of 8 wells was amplified with a unique forward primer containing one of 12 index sequences at its 5' end plus a standard reverse primer (Table 6). Amplifications were performed using Phusion HotStart I (NEB) in 50 uL reactions containing 1× Phusion HF buffer, 0.5 mM dNTPs, 0.5 uM each forward and reverse primer (both 5'-phosphorylated), and 1 U of Phusion polymerase. The following cycling conditions were used: one cycle of 98° C. for 30 s; and 16 cycles of 98° C. for 10 s, 65° C. for 30 s, and 72° C. for 30 s. All 96 reactions were pooled and then purified using a Qiagen MinElute PCR Purification Kit (cat. no. 28004) and a QIAquick Gel Extraction kit (cat. no. 28704). To prepare the circular templates necessary for inverse PCR, DNA was diluted to ~1 ng/uL and ligated with T4 DNA Ligase (Enzymatics) for 30 min at room temperature in a 600 uL reaction containing 1× T4 DNA Ligation Buffer and 18,000 U of T4 DNA Ligase. The ligation reaction was purified using a Qiagen MinElute kit. Inverse PCR was performed using Phusion Hot Start I on 90 ng of circular template distributed in twelve 50 uL reactions, each containing 1× Phusion HF Buffer, 0.25 mM dNTPs, 0.5 uM each of KRAS forward and reverse primers (Table 6) and 1 U of Phusion polymerase. The KRAS-specific primers both contained grafting sequences for hybridization to the Illumina GA IIx flow cell (Table 6). The following cycling conditions were used: one cycle of 98° C. for 2 min; and 37 cycles of 98° C. for 10 s, 61° C. for 15 s, and 72° C. for 10 s. The final purification was performed with a NucleoSpin Extract II kit (Macherey-Nagel) and eluted in 20 uL NE Buffer. The resulting DNA fragments contained UIDs composed of three sequences: two endogenous ones, represented by the two ends of the original sheared fragments plus the exogenous sequence introduced during the indexing amplification. As 12 exogenous sequences were used, this increased the number of distinct UIDs by 12-fold over that obtained without exogenous UIDs. This number could easily be increased by using a greater number of distinct primers.

TABLE 6

Oligonucleotides Used

| Font Legend: | Symbol Legend: |
|---|---|
| REGION COMPLEMENTARY TO TEMPLATES | /5Phos/ = 5' Phosphate |
| TEMPLATE-SPECIFIC UID SEQUENCE | * = Phosphorothioate linkage |
| UNIVERSAL SEQUENCE | |
| EXPERIMENT-SPECIFIC INDEX SEQUENCE | |
| ILLUMINA GRAFTING PRIMERS (FOR | |
| HYBRIDIZATION TO FLOW CELL) | |

| | Sequence (SEQ ID NO: 1-81, respectively) |
|---|---|
| Endogenous UIDs | |
| Capture | |
| Adapter-strand 1 | /5Phos/GATCGGAAGAGCGGTTCAGCAGGAATGCCGAG |
| Adapter-strand 2 | ACACTCTTTCCCTACACGACGCTCTTCCGAT*C*T |
| Whole Genome Amplification-for | AATGATACGGCGACCACCGAGATCTACACACACTCTTTCCCTACACGACGCTCTTCCGAT*C*T |
| Whole Genome Amplification-rev | CAAGCAGAAGACGGCATACGAGATCTCGGCATTCCTGCTGAACCGCTCTTCCGAT*C*T |
| Post-Capture Amplification-for | AATGATACGGCGACCACCGAGATCTACACACACTCTTTCCCTACACGACGCTCTTCCGAT*C*T |
| Post-Capture Amplification-rev | CAAGCAGAAGACGGCATACGAGATCTCGGCATTCCTGCTGAACCGCTCTTCCGAT*C*T |
| Sequencing Primer, Read 1 (Illumina; SanDiego, CA) | ACACTCTTTCCCTACACGACGCTCTTCCGATCT |
| Sequencing Primer, Read 2 (Illumina; SanDiego, CA) | CTCGGCATTCCTGCTGAACCGCTCTTCCGATCT |

TABLE 6-continued

Oligonucleotides Used

Inverse PCR

| | |
|---|---|
| Adapter-strand 1 | /5Phos/GATCGGAAGAGCGGTTCAGCAGGAATGCCGAG |
| Adapter-strand 2 | ACACTCTTTCCCTACACGACGCTCTTCCGAT*C*T |
| Whole Genome Amplification-for-1 | CGTGATACACTCTTTCCCTACACGACGCTCTTCCGAT*C*T Whole |
| Genome Amplification-for-2 | ACATCGACACTCTTTCCCTACACGACGCTCTTCCGAT*C*T |
| Whole Genome Amplification-for-3 | GCCTAAACACTCTTTCCCTACACGACGCTCTTCCGAT*C*T |
| Whole Genome Amplification-for-4 | /TGGTCAACACTCTTTCCCTACACGACGCTCTTCCGAT*C*T |
| Whole Genome Amplification-for-5 | CACTGTACACTCTTTCCCTACACGACGCTCTTCCGAT*C*T |
| Whole Genome Amplification-for-6 | ATTGGCACACTCTTTCCCTACACGACGCTCTTCCGAT*C*T |
| Whole Genome Amplification-for-7 | GATCTGACACTCTTTCCCTACACGACGCTCTTCCGAT*C*T |
| Whole Genome Amplification-for-8 | TCAAGTACACTCTTTCCCTACACGACGCTCTTCCGAT*C*T Whole |
| Genome Amplification-for-9 | CTGATCACACTCTTTCCCTACACGACGCTCTTCCGAT*C*T |
| Whole Genome Amplification-for-10 | AAGCTAACACTCTTTCCCTACACGACGCTCTTCCGAT*C*T |
| Whole Genome Amplification-for-11 | GTAGCCACACTCTTTCCCTACACGACGCTCTTCCGAT*C*T |
| Whole Genome Amplification-for-12 | TACAAGACACTCTTTCCCTACACGACGCTCTTCCGAT*C*T |
| Whole Genome Amplification-rev | /5Phos/CTCGGCATTCCTGCTGAACCGCTCTTCCGAT*C*T |
| Inverse PCR-antisense | AATGATACGGCGACCACCGAGATCTACAC_CAGCAGGCCTTATAATAAAA ATAATGA_ |
| Inverse PCR-for | CAAGCAGAAGACGGCATACGAGATT_TGACTGAATATAAACTTGTGGTAGT TG_ |
| Sequencing Primer 1 (to read internal sequences) | ACACTCTTTCCCTACACGACGCTCTTCCGATCT |
| Sequencing Primer 2 (to read internal sequences) | CTCGGCATTCCTGCTGAACCGCTCTTCCGATCT |
| Index Primer 1 (to read experiment indexes) | CGGAAGAGCGTCGTGTAGGGAAAGAGTGT |
| Index Primer 2 (to read experiment indexes) | CGGAAGAGCGGTTCAGCAGGAATGCCGAG |

Exogenous UIDs

Polymerase Fidelity

| | |
|---|---|
| Digital PCR Amplification-for | _GGTTACAGGCTCATGATGTAACC_ |
| Digital PCR Amplification-rev | _GATACCAGCTTGGTAATGGCA_ |
| UID Assignment Amplification-for | CGACGTAAAACGACGGCCAGTNNNNNNNNNNNNNN_GGTTACAGGCTCATG ATGTAACC_ |
| UID Assignment Amplification-rev | CACACAGGAAACAGCTATGACC_ATGGATACCAGCTTGGTAATGGCA_ |
| Library Amplification-for-1 | AATGATACGGCGACCACCGAGATCTACACCGTGATCGACGTAAAACGAC GGCCA*G*T |
| Library Amplification-for-2 | AATGATACGGCGACCACCGAGATCTACACACATCGCGACGTAAAACGAC GGCCA*G*T |
| Library Amplification-for-3 | AATGATACGGCGACCACCGAGATCTACACGCCTAACGACGTAAAACGAC GGCCA*G*T |
| Library Amplification-for-4 | AATGATACGGCGACCACCGAGATCTACACTGGTCACGACGTAAAACGAC GGCA*G*T |
| Library Amplification-for-5 | AATGATACGGCGACCACCGAGATCTACACCACTGTCGACGTAAAACGAC GGCCA*G*T |
| Library Amplification-for-6 | AATGATACGGCGACCACCGAGATCTACACATTGGCCGACGTAAAACGAC GGCCA*G*T |
| Library Amplification-for-7 | AATGATACGGCGACCACCGAGATCTACACGATCTGCGACGTAAAACGAC GGCCA*G*T |
| Library Amplification-for-8 | AATGATACGGCGACCACCGAGATCTACACTCAAGTCGACGTAAAACGAC GGCCA*G*T |
| Library Amplification-for-9 | AATGATACGGCGACCACCGAGATCTACACCTGATCCGACGTAAAACGAC GGCCA*G*T |
| Library Amplification-for-10 | AATGATACGGCGACCACCGAGATCTACACAAGCTACGACGTAAAACGAC GGCCA*G*T |
| Library Amplification-rev | CAAGCAGAAGACGGCATACGAGATCACACAGGAAACAGCTATGACCA*T *G |
| Sequencing Primer (to read UID and internal sequences) | CGACGTAAAACGACGGCCAGT |
| Index Primer (to read experiment indexes) | ACTGGCCGTCGTTTTACGTCG |

_CTNNB1_ mutations in DNA from normal human cells

| | |
|---|---|
| UID Assignment Amplification-for | CGACGTAAAACGACGGCCAGTNNNNNNNNNNNNNNGCAGCAACAGTCTT ACCTGGACT |
| Library Amplification-for | AATGATACGGCGACCACCGAGATCTACACCGACGTAAAACGACGGCCA* G*T |
| Library Amplification-rev-1 | ATCACGCACACAGGAAACAGCTATGACCA*T*G |
| Library Amplification-rev-2 | CAAGCAGAAGACGGCATACGAGATCGATGTCACACAGGAAACAGCTATG ACCA*T*G |
| Library Amplification-rev-3 | CAAGCAGAAGACGGCATACGAGATTGACCACACACAGGAAACAGCTATG ACCA*T*G |
| Library Amplification-rev-4 | CAAGCAGAAGACGGCATACGAGATATGCCAATCACACAGGAAACAGCTATG ACCA*T*G |

TABLE 6-continued

Oligonucleotides Used

| | |
|---|---|
| Library Amplification-rev-5 | CAAGCAGAAGACGGCATACGAGATCAGATCCACACAGGAAACAGCTATG ACCA*T*G |
| Library Amplification-rev-6 | CAAGCAGAAGACGGCATACGAGATACTTGACACACAGGAAACAGCTATG ACCA*T*G |
| Library Amplification-rev-7 | CAAGCAGAAGACGGCATACGAGATGATCAGCACACAGGAAACAGCTATG ACCA*T*G |
| Library Amplification-rev-8 | CAAGCAGAAGACGGCATACGAGATTAGCTTCACACAGGAAACAGCTATG ACCA*T*G |
| Library Amplification-rev-9 | CAAGCAGAAGACGGCATACGAGATGGCTACCACACAGGAAACAGCTATG ACCA*T*G |
| Library Amplification-rev-10 | CAAGCAGAAGACGGCATACGACATCTTGTACACACAGGAAACAGCTATG ACCA*T*G |
| Sequencing Primer (to read UID and internal sequences) | CGACGTAAAACGACGGCCAGT |
| Index Primer (to read experiment indexes) | CATGGTCATAGCTGTTTCCTGTGTG |
| Mitochondrial mutations in DNA from normal human cells | |
| UID Assignment Amplification-for | CGACGTAAAACGACGGCCAGT*NNNNNNNNNNNNNNNN*TTACCGAGAAAGCT CACAAGAA |
| UID Assignment Amplification-rev | CACACAGGAAACAGCTATGACCATGATGCTAAGGCGAGGATGAAA |
| Library Amplification-for-1 | AATGATACGGCGACCACCGAGATCTACACACATCGCGACGTAAAACGAC GGCCA*G*T |
| Library Amplification-for-2 | AATGATACGGCGACCACCGAGATCTACACGCCTAACGACGTAAAACGAC GGCCA*G*T |
| Library Amplification-for-3 | AATGATACGGCGACCACCGAGATCTACACTGGTCACGACGTAAAACGAC GGCCA*G*T |
| Library Amplification-for-4 | AATGATACGGCGACCACCGAGATCTACACATTGGCCGACGTAAAACGAC GGCCA*G*T |
| Library Amplification-for-5 | AATGATACGGCGACCACCGAGATCTACACGATCTGCGACGTAAAACGAC GGCCA*G*T |
| Library Amplification-for-6 | AATGATACGGCGACCACCGAGATCTACACTCAAGTCGACGTAAAACGAC GGCCA*G*T |
| Library Amplification-for-7 | AATGATACGGCGACCACCGAGATCTACACCTGATCCGACGTAAAACGAC GGCCA*G*T |
| Library Amplification-rev | CAAGCAGAAGACGGCATACGAGATCACACAGGAAACAGCTATGACCA*T *G |
| Sequencing Primer 1 (to read UIDs) | CGACGTAAAACGACGGCCAGT |
| Sequencing Primer 2 (to read internal sequences) | CCTAATTCCCCCCATCCTTAC |
| Index Primer (to read experiment indexes) | ACTGGCCGTCGTTTTACGTCG |
| Analysis of Phosphoramidite Oligonucleotide Composition | |
| Synthesized template, wt | *GGTTACAGGCTCATGATGTAACCTCTGTGTCTTGGTGTAACTTTAAAAC ATATTTTTGCCATTACCAAGCTGGTATC* |
| Synthesized template, mut (S = 50/50 mix of C and G) | *GGTTACAGGCTCATGATGTAACCTCTGTGTCTTGGTGSAACTTTAAAAC ATATTTTTGCCATTACCAAGCTGGTATC* |
| UID Assignment Amplification-for | ACACTCTTTCCCTACACGACGCTC*NNNNNNNNNNNNNN*GGTGAGTCTGTGC AGGCAT |
| UID Assignment Amplification-rev | CTCGAGCACTGTCCTGACTGAGACGATACCAGCTTGGTAATGGCA |
| Library Amplification-for | AATGATACGGCGACCACCGAGATCTACACCGTGATACACTCTTTCCCTA CACGACGC*T*C |
| Library Amplification-rev | CAAGCAGAAGACGGCATACGAGATCTCGAGCACTGTCCTGACTGAG*A* C |
| Sequencing Primer (to read UID and internal sequences) | ACACTCTTTCCCTACACGACGCTC |

Exogenous UIDs. Genomic DNA from normal human colonic mucosae or blood lymphocytes was prepared using Qiagen kits. The DNA from colonic mucosae was used for the experiments on CTNNB1 and mitochondrial DNA, while the lymphocyte DNA was used for the experiments on CTNNB1 and on polymerase fidelity. DNA was quantified with Digital PCR (2) using primers that amplified single-copy genes from human cells (Analysis of Polymerase Fidelity and CTNNB1), qPCR (mitochondrial DNA), or by optical absorbance (oligonucleotides). Each strand of each template molecule was encoded with a 12 or 14 base UID using two cycles of amplicon-specific PCR, as described in the text and FIG. 3. The amplicon-specific primers both contained universal tag sequences at their 5' ends for a later amplification step. The UIDs constituted 12 or 14 random nucleotide sequences appended to the 5' end of the forward amplicon-specific primers (Table 6). These primers can generate 16.8 and 268 million distinct UIDs, respectively. It is important that the number of distinct UIDs greatly exceed the number of original template molecules to minimize the probability that two different original templates acquired the same UID. The UID assignment PCR cycles included Phusion Hot Start II (NEB) in a 45 uL reaction containing 1× Phusion HF buffer, 0.25 mM dNTPs, 0.5 uM each forward and reverse primers, and 2 U of Phusion polymerase. To keep the final template concentrations <1.5 ng/uL, multiple wells were used to create some libraries. The following cycling conditions were employed:

one incubation of 98° C. for 30 s (to activate the Phusion Hot Start II); and two cycles of 98° C. for 10 s, 61° C. for 120 s, and 72° C. for 10 s. To ensure complete removal of the first round primers, each well was digested with 60 U of a single strand DNA specific nuclease (Exonuclease-I; Enzymatics) at 37° C. for 1 hr. After a 5 min heat-inactivation at 98° C., primers complementary to the introduced universal tags (Table 6) were added to a final concentration of 0.5 uM each. These primers contained two terminal phosphorothioates to make them resistant to any residual Exonuclease-I activity. They also contained 5' grafting sequences necessary for hybridization to the Illumina GA IIx flow cell. Finally, they contained an index sequence between the grafting sequence and the universal tag sequence. This index sequence enables the PCR products from multiple different individuals to be simultaneously analyzed in the same flow cell compartment of the sequencer. The following cycling conditions were used for the subsequent 25 cycles of PCR: 98° C. for 10 s and 72° C. for 15 s. No intermediate purification steps were performed in an effort to reduce the losses of template molecules.

After the second round of amplification, wells were consolidated and purified using a Qiagen QIAquick PCR Purification Kit (cat. no. 28104) and eluted in 50 uL EB Buffer (Qiagen). Fragments of the expected size were purified after agarose (mtDNA libraries) or polyacrylamide (all other libraries) gel electrophoresis. For agarose gel purification, the eight 6-uL aliquots were loaded into wells of a 2% Size Select Gel (Invitrogen) and bands of the expected size were collected in EB Buffer as specified by the manufacturer. For polyacrylamide gel purification, ten 5-uL aliquots were loaded into wells of a 10% TBE Polyacrylamide Gel (Invitrogen). Gel slices containing the fragments of interest were excised, crushed, and eluted essentially as described (3).

Analysis of Phusion polymerase fidelity. Amplification of a fragment of human genomic DNA within the BMX (RefSeq Accession NM_203281.2) gene was first performed using the PCR conditions described above. The template was diluted so that an average of one template molecule was present in every 10 wells of a 96-well PCR plate. Fifty uL PCR reactions were then performed in 1×Phusion HF buffer, 0.25 mM dNTPs, 0.5 uM each forward and reverse primers (Table 6), and 2 U of Phusion polymerase. The cycling conditions were one cycle of 98° C. for 30 s; and 19 cycles of 98° C. for 10 s, 61° C. for 120 s, and 72° C. for 10 s. The primers were removed by digestion with 60 U of Exonuclease-I at 37° C. for 1 hr followed by a 5 min heat-inactivation at 98° C. No purification of the PCR product was performed, either before or after Exonuclease-I digestion. The entire contents of each well were then used as templates for the exogenous UIDs strategy described above.

Sequencing. Sequencing of all the libraries described above was performed using an Illumina GA IIx instrument as specified by the manufacturer. The total length of the reads used for each experiment varied from 36 to 73 bases. Base-calling and sequence alignment was performed with the Eland pipeline (Illumina). Only high quality reads meeting the following criteria were used for subsequent analysis: (i) the first 25 bases passed the standard Illumina chastity filter; (ii) every base in the read had a quality score $\geq 20$; and (iii) $\leq 3$ mismatches to expected sequences. For the exogenous UID libraries, we additionally required the UIDs to have a quality score $\geq 30$. We noticed a relatively high frequency of errors at the ends of the reads in the endogenous UID libraries prepared with the standard Illumina protocol, presumably introduced during shearing or end-repair, so the first and last three bases of these tags were excluded from analysis.

Safe-SeqS analysis. High quality reads were grouped into UID-families based on their endogenous or exogenous UIDs. Only UID-families with two or more members were considered. Such UID-families included the vast majority ($\geq 99\%$) of the sequencing reads. To ensure that the same data was used for both conventional and Safe-SeqS analysis, we also excluded UID-families containing only one member from conventional analysis. Furthermore, we only identified a base as "mutant" in conventional sequencing analysis if the same variant was identified in at least two members of at least one UID-family (i.e., two mutations) when comparing conventional analysis to that of Safe-SeqS with exogenous UIDs. For comparison with Safe-SeqS with endogenous UIDs, we required at least two members of each of two UID-families (i.e., four mutations) to identify a position as "mutant" in conventional analysis. With either endogenous or exogenous UIDs, a super-mutant was defined as a UID-family in which $\geq 95\%$ of members shared the identical mutation. Thus, UID-families with <20 members had to be 100% identical at the mutant position, while a 5% combined replication and sequencing error rate was permitted in UID-families with more members. To determine polymerase fidelity using Safe-SeqS, and to compare the results with previous analyses of Phusion polymerase fidelity, it was necessary to realize that the previous analyses would only detect mutations present in both strands of the PCR products (4). This would be equivalent to analyzing PCR products generated with one less cycle with Safe-SeqS, and the appropriate correction was made in Table 2A. Unless otherwise specified, all values listed in the text and Tables represent means and standard deviations.

Example 8—Error-Generating Processes

Apparent mutations, defined as any base call that varies from the expected base at a defined position, can result from a variety of processes:
1. Mutations present in the template DNA. For templates derived from normal human cells, these include mutations that were present in the zygote, occurred later during embryonic and adult development, or were present in a contaminant inadvertently introduced into the sample. These mutations are expected to be present in both strands of the relevant templates. If the mutation occurred only in the last cell-cycle of a cell whose DNA was used as template, the mutation would be present in only one strand of the template.
2. Chemically-modified bases present in the templates. It has been estimated that there are many thousands of oxidized bases present in every human cell (5). When such DNA is amplified by Phusion polymerase, an apparent mutation in one strand may result.
3. Errors introduced during the shearing process required to generate small fragments for sequencing. Acoustic shearing generates short-lived, high temperatures that can damage DNA.
4. Errors introduced during end-repair of the sheared fragments. The source of these errors can be polymerase infidelity or through incorporation of chemically-modified bases in the dNTPs used for polymerization.
5. Errors introduced by other enzymatic steps, particularly if the enzymes are impure and contaminated with nucleases, polymerases, or ligases.

6. Errors introduced during PCR amplification to prepare the libraries for capturing or for inverse PCR.
7. Errors during PCR after capturing or during inverse PCR amplification.
8. Errors introduced into the UID assignment cycles of Safe-SeqS (FIG. 3).
9. Errors introduced into the library amplification cycles of Safe-SeqS performed with exogenous UIDs. Note that if UID assignment primers from process #8 are not completely removed, they could potentially amplify DNA fragments containing errors introduced during these cycles, creating a new super-mutant.
10. Errors introduced into the first bridge-PCR cycle on the Illumina flow cell. If amplification is inefficient, an error introduced into the second bridge-PCR cycle could also result in a cluster containing a mutation in most of its component molecules.
11. Errors in base-calling.

Example 9—Achieving Accuracy with Safe-SeqS

With conventional sequencing-by-synthesis approaches, all the error-producing processes described above are relevant, resulting in a relatively high number of false-positive mutation calls (Tables 1 and 2). Safe-SeqS minimizes the number of false-positive mutation calls in several ways. Safe-SeqS with exogenous UIDs results in the fewest false-positive mutation calls because it requires the fewest enzymatic steps. With exogenous UIDs, error-generating processes #3 to #7 are completely eliminated because these steps aren't performed. Safe-SeqS with exogenous UIDs also drastically reduces errors resulting from error-generating processes #10 and #11 because of the way the data is analyzed.

After Safe-SeqS with exogenous UIDs, the only false-positive errors remaining should be those introduced during the UID assignment PCR cycles (error-generating process #8) or residual UID-containing primers during the library amplification cycles (error-generating process #9). The errors from error-generating process #8 can theoretically be eliminated by requiring at least two super-mutants to identify a position as "mutant." This requirement is reasonable because every pre-existing mutation in a double stranded DNA template should give rise to two super-mutants, one from each strand. Furthermore, this requirement would eliminate error-generating process #2 (damaged bases in the original templates) because such bases, when copied, should give rise to only one super-mutant. Finally, errors generated during the library amplification cycles (process #9) will not be amplified by residual UID-containing primers if those primers are completely removed, such as performed here with excess Exonuclease-I.

With endogenous UIDs, the mistakes introduced by processes #10 and #11 are drastically reduced because of the way in which the data is analyzed (as with exogenous UIDs). Errors introduced in processes #2 to #7 can be minimized by requiring that a mutation be observed in at least two UID-families, for the reasons stated in the paragraph above. With this requirement, few false-positive mutations, in theory, should be identified.

In practice, the situation is complicated by the fact that the various amplifications are not perfect, so every strand of every original template molecule is not recovered as a UID-family. This efficiency can vary from sample to sample, depending in part on the concentration of inhibitors present in clinical samples. Moreover, with exogenous UIDs, a polymerase error during the library amplification step can create a new UID-family that wasn't represented in the UID assignment step. If this error occurred in a mutant template, an additional, artificial super-mutant would be created.

These factors can be managed by incorporating various additional criteria into the analyses. For example, one might require UID-families to contain more than two, five or ten members. Another requirement could be that the exogenous UIDs of super-mutants not be related to any other UID in the library by a one-base difference. This would eliminate artificial super-mutants generated during the library amplification steps (noted in above paragraph). We routinely instituted this requirement in our Safe-SeqS analyses, but it made little difference (<1%) in the number of super-mutants identified. Specificity for mutations can be further increased by requiring more than one super-mutant to identify a position as "mutant," as described above for endogenous UIDs. When requiring multiple super-mutants, the specificity can be even further increased by requiring that each strand of the original double stranded template contain the mutation or, when libraries are amplified using multiple wells, that rare mutations share an introduced sequence that identifies the well in which the mutations (i.e., one from each strand) were amplified. Such decisions involve the usual trade-off between specificity and sensitivity. In our experiments with exogenous UIDs (Table 2), we required only one super-mutant to identify a position as "mutant" and included all UID-families with more than one member. As endogenous UIDs was associated with more error-generating processes than with exogenous UIDs, we required two super-mutants to identify a position as mutant in the experiments reported in Table 1 and also included all UID-families with more than one member.

Example 10—Mutation Prevalences in Normal Human Tissues

The experiments reported in Tables 1 and 2, in which >10,000 templates were assessed, show that mutations are present in the nuclear DNA of normal human cells at a frequency of $3.5 \times 10^{-6}$ to $9.0 \times 10^{-6}$ mutants/bp depending on the region analyzed. It is impossible to determine whether this low level represents genuine mutations present in the original templates or the sum of genuine mutations plus artifactual mutations from the error-generating processes described above. Mutation prevalences in human cells have not been widely investigated, in part because they are so infrequent. However, several clever techniques to identify rare mutants have been devised and can in principle be used for comparison. Unfortunately, estimates of human mutation prevalences vary widely, ranging from as many as $10^{-5}$ mutants/bp to as many as $10^{-8}$ mutants/bp (6-12). In several of these studies, the estimates are complicated by the lack of data on the nature of the actual mutations—they could in some cases be caused by losses of whole chromosomes, in others by missense mutations, and in others mainly by nonsense mutations or small insertions or deletions. Additionally, these studies used various sources of normal cells and examined different genes, making direct comparisons difficult. Estimates of the prevalences and rates of mitochondrial DNA mutations similarly vary (13-19). It will be of interest in future work to analyze the same DNA templates and genes with various technologies to determine the basis for these different estimates.

But let us assume that all of the mutations identified with Safe-SeqS represent genuine mutations present in the original DNA templates from normal cells. What does this tell us about the number of generations though which these cells have proceeded since the organism was conceived? There is a simple relationship between mutation rate and mutation prevalence: the mutation prevalence equals the product of the mutation rate and the number of generations that the cell has gone through since conception. The somatic mutation rate has been determined in previous studies to be ~$10^{-9}$ mutants/bp/generation, though this estimate also varies from study to study for reasons related to those mentioned above with respect to mutation prevalence. Combining this literature-derived estimate of mutation rate with our estimates of mutation prevalence suggests that the normal cells analyzed (lymphocytes, lymphoblastoid cell lines or colonic mucosae) had proceeded through 3,500 to 8,900 generations, representing cells dividing every 3 to 7 days for the individuals examined in this study (average age 65 years).

Example 11—Computer Simulation of Polymerase-Introduced Errors

The timing of mutations introduced by polymerases greatly alters the final number of mutations observed (20). For example, two mutations would differ in prevalence by ~64-fold if introduced 6 cycles apart ($2^6$). Because polymerases introduce mutations in a stochastic manner, a simple Monte Carlo method was employed for the simulations. In these simulations, we used the manufacturer's estimate of the Phusion polymerase error rate with an appropriate adjustment for ability of Safe-SeqS to detect mutations in only one strand (4). Note that errors introduced in cycle 19, as well as in the two UID assignment cycles, would result in changes in only one strand of the duplex—i.e., result in one super-mutant rather than two. In each experiment, we assumed that there was a constant efficiency of amplification given by the total number of templates obtained at the end of the experiment (i.e., if the number of UID-families was N, then we assumed that the number of templates increased by a factor of $N/2^{19}$ in each cycle). One-thousand simulations were performed for each of seven experiments, and the results reported in Table 4.

REFERENCES (FOR EXAMPLES 8-11 ONLY)

1. Herman D S, et al. (2009) Filter-based hybridization capture of subgenomes enables resequencing and copy-number detection. *Nat Methods* 6:507-510.
2. Vogelstein B & Kinzler K W (1999) Digital PCR. *Proc Natl Acad Sci USA* 96:9236-9241.
3. Chory J & Pollard J D, Jr. (2001) Separation of small DNA fragments by conventional gel electrophoresis. *Curr Protoc Mot Blot* Chapter 2:Unit2 7.
4. Barnes W M (1992) The fidelity of Taq polymerase catalyzing PCR is improved by an N-terminal deletion. *Gene* 112:29-35.
5. Collins A R (1999) Oxidative DNA damage, antioxidants, and cancer. *Bioessays* 21:238-246.
6. Morley A A, Cox S, & Holliday R (1982) Human lymphocytes resistant to 6-thioguanine increase with age. *Mech Ageing Dev* 19:21-26.
7. Trainor K J, et al. (1984) Mutation frequency in human lymphocytes increases with age. *Mech Ageing Dev* 27:83-86.
8. Grist S A, McCarron M, Kutlaca A, Turner D R, & Morley A A (1992) In vivo human somatic mutation: frequency and spectrum with age. *Mutat Res* 266:189-196.
9. Williams G T, Geraghty J M, Campbell F, Appleton M A, & Williams E D (1995) Normal colonic mucosa in hereditary non-polyposis colorectal cancer shows no generalised increase in somatic mutation. *Br J Cancer* 71:1077-1080.
10. Campbell F, Appleton M A, Shields C J, & Williams G T (1998) No difference in stem cell somatic mutation between the background mucosa of right- and left-sided sporadic colorectal carcinomas. *J Pathol* 186:31-35.
11. Araten D J, Nafa K, Pakdeesuwan K, & Luzzatto L (1999) Clonal populations of hematopoietic cells with paroxysmal nocturnal hemoglobinuria genotype and phenotype are present in normal individuals. *Proc Natl Acad Sci USA* 96:5209-5214.
12. Araten D J, et al. (2005) A quantitative measurement of the human somatic mutation rate. *Cancer Res* 65:8111-8117.
13. Monnat R J, Jr. & Loeb L A (1985) Nucleotide sequence preservation of human mitochondrial DNA. *Proc Natl Acad Sci USA* 82:2895-2899.
14. Bodenteich A, Mitchell L G, & Merril C R (1991) A lifetime of retinal light exposure does not appear to increase mitochondrial mutations. *Gene* 108:305-309.
15. Howell N, Kubacka I, & Mackey D A (1996) How rapidly does the human mitochondrial genome evolve? *Am J Hum Genet* 59:501-509.
16. Khrapko K, et al. (1997) Mitochondrial mutational spectra in human cells and tissues. *Proc Natl Acad Sci USA* 94:13798-13803.
17. Heyer E, et al. (2001) Phylogenetic and familial estimates of mitochondrial substitution rates: study of control region mutations in deep-rooting pedigrees. *Am J Hum Genet* 69:1113-1126.
18. Howell N, et al. (2003) The pedigree rate of sequence divergence in the human mitochondrial genome: there is a difference between phylogenetic and pedigree rates. *Am J Hum Genet* 72:659-670.
19. Taylor R W, et al. (2003) Mitochondrial DNA mutations in human colonic crypt stem cells. *J Clin Invest* 112:1351-1360.
20. Luria S E & Delbruck M (1943) Mutations of Bacteria from Virus Sensitivity to Virus Resistance. *Genetics* 28:491-511.

REFERENCES (FOR ALL EXCEPT EXAMPLES 8-11)

The disclosure of each reference cited is expressly incorporated herein.

1. Luria S E & Delbruck M (1943) Mutations of Bacteria from Virus Sensitivity to Virus Resistance. *Genetics* 28:491-511.
2. Roach J C, et al. (2010) Analysis of genetic inheritance in a family quartet by whole-genome sequencing. *Science* 328:636-639.
3. Durbin R M, et al. (2010) A map of human genome variation from population-scale sequencing. *Nature* 467:1061-1073.
4. Shibata D (2011) Mutation and epigenetic molecular clocks in cancer. *Carcinogenesis* 32:123-128.
5. McMahon M A, et al. (2007) The HBV drug entecavir—effects on HIV-1 replication and resistance. *N Engl J Med* 356:2614-2621.
6. Eastman P S, et al. (1998) Maternal viral genotypic zidovudine resistance and infrequent failure of zidovudine therapy to prevent perinatal transmission of human immunodeficiency virus type 1 in pediatric AIDS Clinical Trials Group Protocol 076. *J Infect Dis* 177:557-564.

7. Chiu R W, et al. (2008) Noninvasive prenatal diagnosis of fetal chromosomal aneuploidy by massively parallel genomic sequencing of DNA in maternal plasma. *Proc Natl Acad Sci USA* 105:20458-20463.
8. Fan H C, Blumenfeld Y J, Chitkara U, Hudgins L, & Quake S R (2008) Noninvasive diagnosis of fetal aneuploidy by shotgun sequencing DNA from maternal blood. *Proc Natl Acad Sci USA* 105:16266-16271.
9. Hogue M O, et al. (2003) High-throughput molecular analysis of urine sediment for the detection of bladder cancer by high-density single-nucleotide polymorphism array. *Cancer Res* 63:5723-5726.
10. Thunnissen F B (2003) Sputum examination for early detection of lung cancer. *J Clin Pathol* 56:805-810.
11. Diehl F, et al. (2008) Analysis of mutations in DNA isolated from plasma and stool of colorectal cancer patients. *Gastroenterology* 135:489-498.
12. Barnes W M (1992) The fidelity of Taq polymerase catalyzing PCR is improved by an N-terminal deletion. *Gene* 112:29-35.
13. Araten D J, et al. (2005) A quantitative measurement of the human somatic mutation rate. *Cancer Res* 65:8111-8117.
14. Campbell F, Appleton M A, Shields C J, & Williams G T (1998) No difference in stem cell somatic mutation between the background mucosa of right- and left-sided sporadic colorectal carcinomas. *J Pathol* 186:31-35.
15. Tindall K R & Kunkel T A (1988) Fidelity of DNA synthesis by the *Thermus aquaticus* DNA polymerase. *Biochemistry* 27:6008-6013.
16. Kunkel T A (1985) The mutational specificity of DNA polymerase-beta during in vitro DNA synthesis. Production of frameshift, base substitution, and deletion mutations. *J Biol Chem* 260:5787-5796.
17. van Dongen J J & Wolvers-Tettero I L (1991) Analysis of immunoglobulin and T cell receptor genes. Part II: Possibilities and limitations in the diagnosis and management of lymphoproliferative diseases and related disorders. *Clin Chim Acta* 198:93-174.
18. Grist S A, McCarron M, Kutlaca A, Turner D R, & Morley A A (1992) In vivo human somatic mutation: frequency and spectrum with age. *Mutat Res* 266:189-196.
19. Liu Q & Sommer S S (2004) Detection of extremely rare alleles by bidirectional pyrophosphorolysis-activated polymerization allele-specific amplification (Bi-PAP-A): measurement of mutation load in mammalian tissues. *Biotechniques* 36:156-166.
20. Monnat R J, Jr. & Loeb L A (1985) Nucleotide sequence preservation of human mitochondrial DNA. *Proc Natl Acad Sci USA* 82:2895-2899.
21. Shi C, et al. (2004) LigAmp for sensitive detection of single-nucleotide differences. *Nat Methods* 1:141-147.
22. Keohavong P & Thilly W G (1989) Fidelity of DNA polymerases in DNA amplification. *Proc Natl Acad Sci USA* 86:9253-9257.
23. Sidransky D, et al. (1991) Identification of p53 gene mutations in bladder cancers and urine samples. *Science* 252:706-709.
24. Bielas J H & Loeb L A (2005) Quantification of random genomic mutations. *Nat Methods* 2:285-290.
25. Vogelstein B & Kinzler K W (1999) Digital PCR. *Proc Natl Acad Sci USA* 96:9236-9241.
26. Mitra R D, et al. (2003) Digital genotyping and haplotyping with polymerase colonies. *Proc Natl Acad Sci USA* 100:5926-5931.
27. Chetverina H V, Samatov T R, Ugarov V I, & Chetverin A B (2002) Molecular colony diagnostics: detection and quantitation of viral nucleic acids by in-gel PCR. *Biotechniques* 33:150-152, 154, 156.
28. Zimmermann B G, et al. (2008) Digital PCR: a powerful new tool for noninvasive prenatal diagnosis? *Prenat Diagn* 28:1087-1093.
29. Dressman D, Yan H, Traverso G, Kinzler K W, & Vogelstein B (2003) Transforming single DNA molecules into fluorescent magnetic particles for detection and enumeration of genetic variations. *Proc Natl Acad Sci USA* 100:8817-8822.
30. Ottesen E A, Hong J W, Quake S R, & Leadbetter J R (2006) Microfluidic digital PCR enables multigene analysis of individual environmental bacteria. *Science* 314:1464-1467.
31. Quail M A, et al. (2008) A large genome center's improvements to the Illumina sequencing system. *Nat Methods* 5:1005-1010.
32. Nazarian R, et al. (2010) Melanomas acquire resistance to B-RAF (V600E) inhibition by RTK or N-RAS upregulation. *Nature* 468:973-977.
33. He Y, et al. (2010) Heteroplasmic mitochondrial DNA mutations in normal and tumour cells. *Nature* 464:610-614.
34. Gore A, et al. (2011) Somatic coding mutations in human induced pluripotent stem cells. *Nature* 471:63-67.
35. Dohm J C, Lottaz C, Borodina T, & Himmelbauer H (2008) Substantial biases in ultra-short read data sets from high-throughput DNA sequencing. *Nucleic Acids Res* 36:e105.
36. Erlich Y, Mitra P P, delaBastide M, McCombie W R, & Hannon G J (2008) Alta-Cyclic: a self-optimizing base caller for next-generation sequencing. *Nat Methods* 5:679-682.
37. Rougemont J, et al. (2008) Probabilistic base calling of Solexa sequencing data. *BMC Bioinformatics* 9:431.
38. Druley T E, et al. (2009) Quantification of rare allelic variants from pooled genomic DNA. *Nat Methods* 6:263-265.
39. Vallania F L, et al. (2010) High-throughput discovery of rare insertions and deletions in large cohorts. *Genome Res* 20:1711-1718.
40. McCloskey M L, Stoger R, Hansen R S, & Laird C D (2007) Encoding PCR products with batch-stamps and barcodes. *Biochem Genet* 45:761-767.
41. Parameswaran P, et al. (2007) A pyrosequencing-tailored nucleotide barcode design unveils opportunities for large-scale sample multiplexing. *Nucleic Acids Res* 35:e130.
42. Craig D W, et al. (2008) Identification of genetic variants using bar-coded multiplexed sequencing. *Nat Methods* 5:887-893.
43. Miner B E, Stoger R J, Burden A F, Laird C D, & Hansen R S (2004) Molecular barcodes detect redundancy and contamination in hairpin-bisulfite PCR. *Nucleic Acids Res* 32:e135.
44. Herman D S, et al. (2009) Filter-based hybridization capture of subgenomes enables resequencing and copy-number detection. *Nat Methods* 6:507-510.
45. Jones P A & Baylin S B (2007) The epigenomics of cancer. *Cell* 128:683-692.

46. de Boer J G & Ripley L S (1988) An in vitro assay for frameshift mutations: hotspots for deletions of 1 bp by Klenow-fragment polymerase share a consensus DNA sequence. *Genetics* 118:181-191.
47. Eckert K A & Kunkel T A (1990) High fidelity DNA synthesis by the *Thermus aquaticus* DNA polymerase. *Nucleic Acids Res* 18:3739-3744.
48. Kosuri S, et al. (2010) Scalable gene synthesis by selective amplification of DNA pools from high-fidelity microchips. *Nat Biotechnol* 28:1295-1299.
49. Matzas M, et al. (2010) High-fidelity gene synthesis by retrieval of sequence-verified DNA identified using high-throughput pyrosequencing. *Nat Biotechnol* 28:1291-1294.
50. Li J, et al. (2008) Replacing PCR with COLD-PCR enriches variant DNA sequences and redefines the sensitivity of genetic testing. *Nat Med* 14:579-584.
51. Eid J, et al. (2009) Real-time DNA sequencing from single polymerase molecules. *Science* 323:133-138.

We claim:

1. A method of determining that both strands of an initial UID strand pair double-stranded template molecule are mutated comprising:
   a) providing an initial UID strand pair double-stranded template molecule comprising a first nucleic acid strand and a second nucleic acid strand, and
   wherein said initial UID strand pair double-stranded template molecule comprises a first UID at one end, and a second UID at the other end,
   b) subjecting said initial UID strand pair double-stranded template molecule or amplicons thereof to paired-end run sequencing on a massively parallel sequencer to generate first paired-end reads and second paired-end reads;
   c) differentiating which strand of said initial UID strand pair double-stranded template molecule is represented by said first and second paired-end reads based on the observed orientation and order of said first and second UIDs in said first and second paired-end reads when sequence information is obtained from said paired-end run sequencing;
   d) grouping said first and second paired-end reads to yield a first UID family and a second UID family, wherein said first UID family comprises said first paired-end reads and said second UID family comprises said second paired-end reads;
   e) comparing nucleotide sequences between members of said first UID family, and comparing nucleotide sequences between members of said second UID family, and identifying a first nucleotide sequence as accurately representing said first nucleic acid strand, and identifying a second nucleotide sequence as accurately representing said second nucleic acid strand of said initial UID strand pair double-stranded template molecule when at least 50% of members of said first UID family, and said second UID family, contain said first nucleotide sequence and said second nucleotide sequence respectively; and
   f) determining that both strands of said initial UID strand pair double-stranded template molecule are mutated by detecting a difference in said first and second nucleotide sequences at the same position with respect to a reference.

2. The method of claim 1, wherein said first and second UIDs comprise endogenous UIDs.

3. The method of claim 1, wherein said first and second UIDs comprise exogenous UIDs.

4. The method of claim 3, wherein said first and second UIDs were attached to an initial double-stranded template molecule by ligation to form said initial UID strand pair double-stranded template molecule.

5. The method of claim 3, wherein said first and second UIDs were attached to an initial double-stranded template molecule by PCR to form said initial UID strand pair double-stranded template molecule.

6. The method of claim 3, wherein said first and second UIDs are each 4 to 400 bases in length.

7. The method of claim 1, wherein said at least 50% is at least 70%.

8. The method of claim 1, wherein said position that is mutated comprises a mutation selected from: a single base substitution, an insertion, or a deletion.

* * * * *

UNITED STATES PATENT AND TRADEMARK OFFICE
CERTIFICATE OF CORRECTION

| | | |
|---|---|---|
| PATENT NO. | : 12,252,743 B2 | Page 1 of 1 |
| APPLICATION NO. | : 18/507776 | |
| DATED | : March 18, 2025 | |
| INVENTOR(S) | : Vogelstein et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 3 days.

Signed and Sealed this
Ninth Day of September, 2025

Coke Morgan Stewart
*Acting Director of the United States Patent and Trademark Office*

```
                             SEQUENCE LISTING

Sequence total quantity: 81
SEQ ID NO: 1             moltype = DNA  length = 32
FEATURE                  Location/Qualifiers
source                   1..32
                         mol_type = other DNA
                         organism = synthetic construct
SEQUENCE: 1
gatcggaaga gcggttcagc aggaatgccg ag                                 32

SEQ ID NO: 2             moltype = DNA  length = 33
FEATURE                  Location/Qualifiers
source                   1..33
                         mol_type = other DNA
                         organism = synthetic construct
SEQUENCE: 2
acactctttc cctacacgac gctcttccga tct                                33

SEQ ID NO: 3             moltype = DNA  length = 62
FEATURE                  Location/Qualifiers
source                   1..62
                         mol_type = other DNA
                         organism = synthetic construct
SEQUENCE: 3
aatgatacgg cgaccaccga gatctacaca cactctttcc ctacacgacg ctcttccgat   60
ct                                                                  62

SEQ ID NO: 4             moltype = DNA  length = 57
FEATURE                  Location/Qualifiers
source                   1..57
                         mol_type = other DNA
                         organism = synthetic construct
SEQUENCE: 4
caagcagaag acggcatacg agatctcggc attcctgctg aaccgctctt ccgatct      57

SEQ ID NO: 5             moltype = DNA  length = 62
FEATURE                  Location/Qualifiers
source                   1..62
                         mol_type = other DNA
                         organism = synthetic construct
SEQUENCE: 5
aatgatacgg cgaccaccga gatctacaca cactctttcc ctacacgacg ctcttccgat   60
ct                                                                  62

SEQ ID NO: 6             moltype = DNA  length = 57
FEATURE                  Location/Qualifiers
source                   1..57
                         mol_type = other DNA
                         organism = synthetic construct
SEQUENCE: 6
caagcagaag acggcatacg agatctcggc attcctgctg aaccgctctt ccgatct      57

SEQ ID NO: 7             moltype = DNA  length = 33
FEATURE                  Location/Qualifiers
source                   1..33
                         mol_type = other DNA
                         organism = synthetic construct
SEQUENCE: 7
acactctttc cctacacgac gctcttccga tct                                33

SEQ ID NO: 8             moltype = DNA  length = 33
FEATURE                  Location/Qualifiers
source                   1..33
                         mol_type = other DNA
                         organism = synthetic construct
```

```
SEQUENCE: 8
ctcggcattc ctgctgaacc gctcttccga tct                               33

SEQ ID NO: 9               moltype = DNA   length = 32
FEATURE                    Location/Qualifiers
source                     1..32
                           mol_type = other DNA
                           organism = synthetic construct
SEQUENCE: 9
gatcggaaga gcggttcagc aggaatgccg ag                                32

SEQ ID NO: 10              moltype = DNA   length = 33
FEATURE                    Location/Qualifiers
source                     1..33
                           mol_type = other DNA
                           organism = synthetic construct
SEQUENCE: 10
acactctttc cctacacgac gctcttccga tct                               33

SEQ ID NO: 11              moltype = DNA   length = 39
FEATURE                    Location/Qualifiers
source                     1..39
                           mol_type = other DNA
                           organism = synthetic construct
SEQUENCE: 11
cgtgatacac tctttcccta cacgacgctc ttccgatct                         39

SEQ ID NO: 12              moltype = DNA   length = 39
FEATURE                    Location/Qualifiers
source                     1..39
                           mol_type = other DNA
                           organism = synthetic construct
SEQUENCE: 12
acatcgacac tctttcccta cacgacgctc ttccgatct                         39

SEQ ID NO: 13              moltype = DNA   length = 39
FEATURE                    Location/Qualifiers
source                     1..39
                           mol_type = other DNA
                           organism = synthetic construct
SEQUENCE: 13
gcctaaacac tctttcccta cacgacgctc ttccgatct                         39

SEQ ID NO: 14              moltype = DNA   length = 39
FEATURE                    Location/Qualifiers
source                     1..39
                           mol_type = other DNA
                           organism = synthetic construct
SEQUENCE: 14
tggtcaacac tctttcccta cacgacgctc ttccgatct                         39

SEQ ID NO: 15              moltype = DNA   length = 39
FEATURE                    Location/Qualifiers
source                     1..39
                           mol_type = other DNA
                           organism = synthetic construct
SEQUENCE: 15
cactgtacac tctttcccta cacgacgctc ttccgatct                         39

SEQ ID NO: 16              moltype = DNA   length = 39
FEATURE                    Location/Qualifiers
source                     1..39
                           mol_type = other DNA
                           organism = synthetic construct
SEQUENCE: 16
attggcacac tctttcccta cacgacgctc ttccgatct                         39

SEQ ID NO: 17              moltype = DNA   length = 39
FEATURE                    Location/Qualifiers
source                     1..39
                           mol_type = other DNA
                           organism = synthetic construct
SEQUENCE: 17
gatctgacac tctttcccta cacgacgctc ttccgatct                         39

SEQ ID NO: 18              moltype = DNA   length = 39
FEATURE                    Location/Qualifiers
source                     1..39
                           mol_type = other DNA
```

```
                            organism = synthetic construct
SEQUENCE: 18
tcaagtacac tctttcccta cacgacgctc ttccgatct                          39

SEQ ID NO: 19           moltype = DNA  length = 39
FEATURE                 Location/Qualifiers
source                  1..39
                        mol_type = other DNA
                        organism = synthetic construct
SEQUENCE: 19
ctgatcacac tctttcccta cacgacgctc ttccgatct                          39

SEQ ID NO: 20           moltype = DNA  length = 39
FEATURE                 Location/Qualifiers
source                  1..39
                        mol_type = other DNA
                        organism = synthetic construct
SEQUENCE: 20
aagctaacac tctttcccta cacgacgctc ttccgatct                          39

SEQ ID NO: 21           moltype = DNA  length = 39
FEATURE                 Location/Qualifiers
source                  1..39
                        mol_type = other DNA
                        organism = synthetic construct
SEQUENCE: 21
gtagccacac tctttcccta cacgacgctc ttccgatct                          39

SEQ ID NO: 22           moltype = DNA  length = 39
FEATURE                 Location/Qualifiers
source                  1..39
                        mol_type = other DNA
                        organism = synthetic construct
SEQUENCE: 22
tacaagacac tctttcccta cacgacgctc ttccgatct                          39

SEQ ID NO: 23           moltype = DNA  length = 33
FEATURE                 Location/Qualifiers
source                  1..33
                        mol_type = other DNA
                        organism = synthetic construct
SEQUENCE: 23
ctcggcattc ctgctgaacc gctcttccga tct                                33

SEQ ID NO: 24           moltype = DNA  length = 56
FEATURE                 Location/Qualifiers
source                  1..56
                        mol_type = other DNA
                        organism = synthetic construct
SEQUENCE: 24
aatgatacgg cgaccaccga gatctacacc agcaggcctt ataataaaaa taatga       56

SEQ ID NO: 25           moltype = DNA  length = 51
FEATURE                 Location/Qualifiers
source                  1..51
                        mol_type = other DNA
                        organism = synthetic construct
SEQUENCE: 25
caagcagaag acggcatacg agattgactg aatataaact tgtggtagtt g            51

SEQ ID NO: 26           moltype = DNA  length = 33
FEATURE                 Location/Qualifiers
source                  1..33
                        mol_type = other DNA
                        organism = synthetic construct
SEQUENCE: 26
acactctttc cctacacgac gctcttccga tct                                33

SEQ ID NO: 27           moltype = DNA  length = 33
FEATURE                 Location/Qualifiers
source                  1..33
                        mol_type = other DNA
                        organism = synthetic construct
SEQUENCE: 27
ctcggcattc ctgctgaacc gctcttccga tct                                33

SEQ ID NO: 28           moltype = DNA  length = 29
FEATURE                 Location/Qualifiers
source                  1..29
```

```
                        mol_type = other DNA
                        organism = synthetic construct
SEQUENCE: 28
cggaagagcg tcgtgtaggg aaagagtgt                                       29

SEQ ID NO: 29           moltype = DNA   length = 29
FEATURE                 Location/Qualifiers
source                  1..29
                        mol_type = other DNA
                        organism = synthetic construct
SEQUENCE: 29
cggaagagcg gttcagcagg aatgccgag                                       29

SEQ ID NO: 30           moltype = DNA   length = 23
FEATURE                 Location/Qualifiers
source                  1..23
                        mol_type = other DNA
                        organism = synthetic construct
SEQUENCE: 30
ggttacaggc tcatgatgta acc                                             23

SEQ ID NO: 31           moltype = DNA   length = 21
FEATURE                 Location/Qualifiers
source                  1..21
                        mol_type = other DNA
                        organism = synthetic construct
SEQUENCE: 31
gataccagct tggtaatggc a                                               21

SEQ ID NO: 32           moltype = DNA   length = 56
FEATURE                 Location/Qualifiers
source                  1..56
                        mol_type = other DNA
                        organism = synthetic construct
SEQUENCE: 32
cgacgtaaaa cgacggccag tnnnnnnnnn nnnggttaca ggctcatgat gtaacc         56

SEQ ID NO: 33           moltype = DNA   length = 46
FEATURE                 Location/Qualifiers
source                  1..46
                        mol_type = other DNA
                        organism = synthetic construct
SEQUENCE: 33
cacacaggaa acagctatga ccatggatac cagcttggta atggca                    46

SEQ ID NO: 34           moltype = DNA   length = 56
FEATURE                 Location/Qualifiers
source                  1..56
                        mol_type = other DNA
                        organism = synthetic construct
SEQUENCE: 34
aatgatacgg cgaccaccga gatctacacc gtgatcgacg taaaacgacg gccagt         56

SEQ ID NO: 35           moltype = DNA   length = 56
FEATURE                 Location/Qualifiers
source                  1..56
                        mol_type = other DNA
                        organism = synthetic construct
SEQUENCE: 35
aatgatacgg cgaccaccga gatctacaca catcgcgacg taaaacgacg gccagt         56

SEQ ID NO: 36           moltype = DNA   length = 56
FEATURE                 Location/Qualifiers
source                  1..56
                        mol_type = other DNA
                        organism = synthetic construct
SEQUENCE: 36
aatgatacgg cgaccaccga gatctacacg cctaacgacg taaaacgacg gccagt         56

SEQ ID NO: 37           moltype = DNA   length = 56
FEATURE                 Location/Qualifiers
source                  1..56
                        mol_type = other DNA
                        organism = synthetic construct
SEQUENCE: 37
aatgatacgg cgaccaccga gatctacact ggtcacgacg taaaacgacg gccagt         56

SEQ ID NO: 38           moltype = DNA   length = 56
FEATURE                 Location/Qualifiers
```

```
                            -continued source                  1..56
                        mol_type = other DNA
                        organism = synthetic construct
SEQUENCE: 38
aatgatacgg cgaccaccga gatctacacc actgtcgacg taaaacgacg gccagt          56

SEQ ID NO: 39           moltype = DNA   length = 56
FEATURE                 Location/Qualifiers
source                  1..56
                        mol_type = other DNA
                        organism = synthetic construct
SEQUENCE: 39
aatgatacgg cgaccaccga gatctacaca ttggccgacg taaaacgacg gccagt          56

SEQ ID NO: 40           moltype = DNA   length = 56
FEATURE                 Location/Qualifiers
source                  1..56
                        mol_type = other DNA
                        organism = synthetic construct
SEQUENCE: 40
aatgatacgg cgaccaccga gatctacacg atctgcgacg taaaacgacg gccagt          56

SEQ ID NO: 41           moltype = DNA   length = 56
FEATURE                 Location/Qualifiers
source                  1..56
                        mol_type = other DNA
                        organism = synthetic construct
SEQUENCE: 41
aatgatacgg cgaccaccga gatctacact caagtcgacg taaaacgacg gccagt          56

SEQ ID NO: 42           moltype = DNA   length = 56
FEATURE                 Location/Qualifiers
source                  1..56
                        mol_type = other DNA
                        organism = synthetic construct
SEQUENCE: 42
aatgatacgg cgaccaccga gatctacacc tgatccgacg taaaacgacg gccagt          56

SEQ ID NO: 43           moltype = DNA   length = 56
FEATURE                 Location/Qualifiers
source                  1..56
                        mol_type = other DNA
                        organism = synthetic construct
SEQUENCE: 43
aatgatacgg cgaccaccga gatctacaca agctacgacg taaaacgacg gccagt          56

SEQ ID NO: 44           moltype = DNA   length = 49
FEATURE                 Location/Qualifiers
source                  1..49
                        mol_type = other DNA
                        organism = synthetic construct
SEQUENCE: 44
caagcagaag acggcatacg agatcacaca ggaaacagct atgaccatg                  49

SEQ ID NO: 45           moltype = DNA   length = 21
FEATURE                 Location/Qualifiers
source                  1..21
                        mol_type = other DNA
                        organism = synthetic construct
SEQUENCE: 45
cgacgtaaaa cgacggccag t                                                21

SEQ ID NO: 46           moltype = DNA   length = 21
FEATURE                 Location/Qualifiers
source                  1..21
                        mol_type = other DNA
                        organism = synthetic construct
SEQUENCE: 46
actggccgtc gttttacgtc g                                                21

SEQ ID NO: 47           moltype = DNA   length = 58
FEATURE                 Location/Qualifiers
source                  1..58
                        mol_type = other DNA
                        organism = synthetic construct
SEQUENCE: 47
cgacgtaaaa cgacggccag tnnnnnnnnn nnnnngcagc aacagtctta cctggact        58

SEQ ID NO: 48           moltype = DNA   length = 48
```

```
FEATURE                 Location/Qualifiers
source                  1..48
                        mol_type = other DNA
                        organism = synthetic construct
SEQUENCE: 48
cacacaggaa acagctatga ccatgtccac atcctcttcc tcaggatt              48

SEQ ID NO: 49           moltype = DNA   length = 50
FEATURE                 Location/Qualifiers
source                  1..50
                        mol_type = other DNA
                        organism = synthetic construct
SEQUENCE: 49
aatgatacgg cgaccaccga gatctacacc gacgtaaaac gacggccagt            50

SEQ ID NO: 50           moltype = DNA   length = 55
FEATURE                 Location/Qualifiers
source                  1..55
                        mol_type = other DNA
                        organism = synthetic construct
SEQUENCE: 50
caagcagaag acggcatacg agatatcacg cacacaggaa acagctatga ccatg      55

SEQ ID NO: 51           moltype = DNA   length = 55
FEATURE                 Location/Qualifiers
source                  1..55
                        mol_type = other DNA
                        organism = synthetic construct
SEQUENCE: 51
caagcagaag acggcatacg agatcgatgt cacacaggaa acagctatga ccatg      55

SEQ ID NO: 52           moltype = DNA   length = 55
FEATURE                 Location/Qualifiers
source                  1..55
                        mol_type = other DNA
                        organism = synthetic construct
SEQUENCE: 52
caagcagaag acggcatacg agattgacca cacacaggaa acagctatga ccatg      55

SEQ ID NO: 53           moltype = DNA   length = 55
FEATURE                 Location/Qualifiers
source                  1..55
                        mol_type = other DNA
                        organism = synthetic construct
SEQUENCE: 53
caagcagaag acggcatacg agatgccaat cacacaggaa acagctatga ccatg      55

SEQ ID NO: 54           moltype = DNA   length = 55
FEATURE                 Location/Qualifiers
source                  1..55
                        mol_type = other DNA
                        organism = synthetic construct
SEQUENCE: 54
caagcagaag acggcatacg agatcagatc cacacaggaa acagctatga ccatg      55

SEQ ID NO: 55           moltype = DNA   length = 55
FEATURE                 Location/Qualifiers
source                  1..55
                        mol_type = other DNA
                        organism = synthetic construct
SEQUENCE: 55
caagcagaag acggcatacg agatacttga cacacaggaa acagctatga ccatg      55

SEQ ID NO: 56           moltype = DNA   length = 55
FEATURE                 Location/Qualifiers
source                  1..55
                        mol_type = other DNA
                        organism = synthetic construct
SEQUENCE: 56
caagcagaag acggcatacg agatgatcag cacacaggaa acagctatga ccatg      55

SEQ ID NO: 57           moltype = DNA   length = 55
FEATURE                 Location/Qualifiers
source                  1..55
                        mol_type = other DNA
                        organism = synthetic construct
SEQUENCE: 57
caagcagaag acggcatacg agattagctt cacacaggaa acagctatga ccatg      55
```

```
SEQ ID NO: 58              moltype = DNA  length = 55
FEATURE                    Location/Qualifiers
source                     1..55
                           mol_type = other DNA
                           organism = synthetic construct
SEQUENCE: 58
caagcagaag acggcatacg agatggctac cacacaggaa acagctatga ccatg       55

SEQ ID NO: 59              moltype = DNA  length = 55
FEATURE                    Location/Qualifiers
source                     1..55
                           mol_type = other DNA
                           organism = synthetic construct
SEQUENCE: 59
caagcagaag acggcatacg agatcttgta cacacaggaa acagctatga ccatg       55

SEQ ID NO: 60              moltype = DNA  length = 21
FEATURE                    Location/Qualifiers
source                     1..21
                           mol_type = other DNA
                           organism = synthetic construct
SEQUENCE: 60
cgacgtaaaa cgacggccag t                                            21

SEQ ID NO: 61              moltype = DNA  length = 25
FEATURE                    Location/Qualifiers
source                     1..25
                           mol_type = other DNA
                           organism = synthetic construct
SEQUENCE: 61
catggtcata gctgtttcct gtgtg                                        25

SEQ ID NO: 62              moltype = DNA  length = 57
FEATURE                    Location/Qualifiers
source                     1..57
                           mol_type = other DNA
                           organism = synthetic construct
SEQUENCE: 62
cgacgtaaaa cgacggccag tnnnnnnnnn nnnnnttacc gagaaagctc acaagaa     57

SEQ ID NO: 63              moltype = DNA  length = 45
FEATURE                    Location/Qualifiers
source                     1..45
                           mol_type = other DNA
                           organism = synthetic construct
SEQUENCE: 63
cacacaggaa acagctatga ccatgatgct aaggcgagga tgaaa                  45

SEQ ID NO: 64              moltype = DNA  length = 56
FEATURE                    Location/Qualifiers
source                     1..56
                           mol_type = other DNA
                           organism = synthetic construct
SEQUENCE: 64
aatgatacgg cgaccaccga gatctacaca catcgcgacg taaaacgacg gccagt      56

SEQ ID NO: 65              moltype = DNA  length = 56
FEATURE                    Location/Qualifiers
source                     1..56
                           mol_type = other DNA
                           organism = synthetic construct
SEQUENCE: 65
aatgatacgg cgaccaccga gatctacacg cctaacgacg taaaacgacg gccagt      56

SEQ ID NO: 66              moltype = DNA  length = 56
FEATURE                    Location/Qualifiers
source                     1..56
                           mol_type = other DNA
                           organism = synthetic construct
SEQUENCE: 66
aatgatacgg cgaccaccga gatctacact ggtcacgacg taaaacgacg gccagt      56

SEQ ID NO: 67              moltype = DNA  length = 56
FEATURE                    Location/Qualifiers
source                     1..56
                           mol_type = other DNA
                           organism = synthetic construct
SEQUENCE: 67
aatgatacgg cgaccaccga gatctacaca ttggccgacg taaaacgacg gccagt      56
```

```
SEQ ID NO: 68          moltype = DNA   length = 56
FEATURE                Location/Qualifiers
source                 1..56
                       mol_type = other DNA
                       organism = synthetic construct
SEQUENCE: 68
aatgatacgg cgaccaccga gatctacacg atctgcgacg taaaacgacg gccagt          56

SEQ ID NO: 69          moltype = DNA   length = 56
FEATURE                Location/Qualifiers
source                 1..56
                       mol_type = other DNA
                       organism = synthetic construct
SEQUENCE: 69
aatgatacgg cgaccaccga gatctacact caagtcgacg taaaacgacg gccagt          56

SEQ ID NO: 70          moltype = DNA   length = 56
FEATURE                Location/Qualifiers
source                 1..56
                       mol_type = other DNA
                       organism = synthetic construct
SEQUENCE: 70
aatgatacgg cgaccaccga gatctacacc tgatccgacg taaaacgacg gccagt          56

SEQ ID NO: 71          moltype = DNA   length = 49
FEATURE                Location/Qualifiers
source                 1..49
                       mol_type = other DNA
                       organism = synthetic construct
SEQUENCE: 71
caagcagaag acggcatacg agatcacaca ggaaacagct atgaccatg                  49

SEQ ID NO: 72          moltype = DNA   length = 21
FEATURE                Location/Qualifiers
source                 1..21
                       mol_type = other DNA
                       organism = synthetic construct
SEQUENCE: 72
cgacgtaaaa cgacggccag t                                                21

SEQ ID NO: 73          moltype = DNA   length = 21
FEATURE                Location/Qualifiers
source                 1..21
                       mol_type = other DNA
                       organism = synthetic construct
SEQUENCE: 73
cctaattccc cccatcctta c                                                21

SEQ ID NO: 74          moltype = DNA   length = 21
FEATURE                Location/Qualifiers
source                 1..21
                       mol_type = other DNA
                       organism = synthetic construct
SEQUENCE: 74
actggccgtc gttttacgtc g                                                21

SEQ ID NO: 75          moltype = DNA   length = 77
FEATURE                Location/Qualifiers
source                 1..77
                       mol_type = other DNA
                       organism = synthetic construct
SEQUENCE: 75
ggttacaggc tcatgatgta acctctgtgt cttggtgtaa cttttaaaaca tattttttgcc    60
attaccaagc tggtatc                                                     77

SEQ ID NO: 76          moltype = DNA   length = 77
FEATURE                Location/Qualifiers
source                 1..77
                       mol_type = other DNA
                       organism = synthetic construct
SEQUENCE: 76
ggttacaggc tcatgatgta acctctgtgt cttggtgsaa cttttaaaaca tattttttgcc    60
attaccaagc tggtatc                                                     77

SEQ ID NO: 77          moltype = DNA   length = 55
FEATURE                Location/Qualifiers
source                 1..55
                       mol_type = other DNA
```

```
                          organism = synthetic construct
SEQUENCE: 77
acactctttc cctacacgac gctcnnnnnn nnnnnnggtg agtctgtgca ggcat        55

SEQ ID NO: 78           moltype = DNA  length = 45
FEATURE                 Location/Qualifiers
source                  1..45
                        mol_type = other DNA
                        organism = synthetic construct
SEQUENCE: 78
ctcgagcact gtcctgactg agacgatacc agcttggtaa tggca                  45

SEQ ID NO: 79           moltype = DNA  length = 59
FEATURE                 Location/Qualifiers
source                  1..59
                        mol_type = other DNA
                        organism = synthetic construct
SEQUENCE: 79
aatgatacgg cgaccaccga gatctacacc gtgatacact ctttccctac acgacgctc   59

SEQ ID NO: 80           moltype = DNA  length = 48
FEATURE                 Location/Qualifiers
source                  1..48
                        mol_type = other DNA
                        organism = synthetic construct
SEQUENCE: 80
caagcagaag acggcatacg agatctcgag cactgtcctg actgagac               48

SEQ ID NO: 81           moltype = DNA  length = 24
FEATURE                 Location/Qualifiers
source                  1..24
                        mol_type = other DNA
                        organism = synthetic construct
SEQUENCE: 81
acactctttc cctacacgac gctc                                         24
```